(12) United States Patent
Mayou et al.

(10) Patent No.: US 10,349,871 B2
(45) Date of Patent: Jul. 16, 2019

(54) SYSTEMS AND METHODS FOR DETECTING GLUCOSE LEVEL DATA PATTERNS

(75) Inventors: Phil Mayou, San Diego, CA (US);
Hari Hampapuram, San Diego, CA (US); David Price, Carlsbad, CA (US); Keri Weindel, Concord, CA (US); Kostyantyn Snisarenko, San Diego, CA (US); Michael Robert Mensinger, San Diego, CA (US); Leif N. Bowman, Livermore, CA (US); Robert J. Boock, Carlsbad, CA (US); Apurv Ullas Kamath, San Diego, CA (US); Eli Reihman, San Diego, CA (US); Peter C. Simpson, Encinitas, CA (US)

(73) Assignee: DexCom, Inc., San Diego, CA (US)

( * ) Notice: Subject to any disclaimer, the term of this patent is extended or adjusted under 35 U.S.C. 154(b) by 794 days.

(21) Appl. No.: 13/566,678

(22) Filed: Aug. 3, 2012

(65) Prior Publication Data
US 2013/0035575 A1    Feb. 7, 2013

Related U.S. Application Data

(60) Provisional application No. 61/515,786, filed on Aug. 5, 2011, provisional application No. 61/660,650, filed on Jun. 15, 2012.

(51) Int. Cl.
*G01N 33/48* (2006.01)
*A61B 5/145* (2006.01)
(Continued)

(52) U.S. Cl.
CPC ......... *A61B 5/14532* (2013.01); *G16H 15/00* (2018.01); *G16H 50/20* (2018.01); *G16H 50/70* (2018.01); *Y02A 90/26* (2018.01)

(58) Field of Classification Search
None
See application file for complete search history.

(56) References Cited

U.S. PATENT DOCUMENTS

| | | | |
|---|---|---|---|
| 5,507,288 A | 4/1996 | Bocker et al. | |
| 7,025,425 B2 * | 4/2006 | Kovatchev | G06F 19/3418 600/309 |

(Continued)

FOREIGN PATENT DOCUMENTS

| | | | | |
|---|---|---|---|---|
| WO | WO 2010/075350 | * | 7/2010 | G06F 19/00 |

OTHER PUBLICATIONS

Kovatchev et al., Diabetes Care 29(11):2433-2438 (Nov. 2006): Evaluation of a New Measure of Blood Glucose Variability in Diabetes.

(Continued)

*Primary Examiner* — Larry D Riggs, II
(74) *Attorney, Agent, or Firm* — Knobbe Martens Olson & Bear, LLP

(57) ABSTRACT

Systems and methods for detecting and reporting patterns in analyte concentration data are provided. According to some implementations, an implantable device for continuous measurement of an analyte concentration is disclosed. The implantable device includes a sensor configured to generate a signal indicative of a concentration of an analyte in a host, a memory configured to store data corresponding at least one of the generated signal and user information, a processor configured to receive data from at least one of the memory and the sensor, wherein the processor is configured to generate pattern data based on the received information, and an output module configured to output the generated pattern data. The pattern data can be based on detecting frequency and severity of analyte data in clinically risky ranges.

21 Claims, 16 Drawing Sheets

(51) Int. Cl.
  *G16H 50/70* (2018.01)
  *G16H 50/20* (2018.01)
  *G16H 15/00* (2018.01)

(56) References Cited

U.S. PATENT DOCUMENTS

| | | | | |
|---|---|---|---|---|
| 9,107,623 | B2* | 8/2015 | Brauker | A61B 5/1468 |
| 2003/0216628 | A1* | 11/2003 | Bortz et al. | 600/365 |
| 2007/0016381 | A1* | 1/2007 | Kamath | A61B 5/14532 702/19 |
| 2007/0253021 | A1 | 11/2007 | Mehta et al. | |
| 2008/0220403 | A1 | 9/2008 | Marling et al. | |
| 2010/0160740 | A1 | 6/2010 | Cohen | |
| 2011/0004085 | A1* | 1/2011 | Mensinger | A61B 5/0031 600/365 |
| 2013/0332181 | A1 | 12/2013 | Schmidt et al. | |
| 2013/0332182 | A1 | 12/2013 | Schmidt et al. | |

OTHER PUBLICATIONS

Kovatchev et al., Diabetes Technology & Therapeutics 4(3):295-303 (2002): Methods for Quantifying Self-Monitoring Blood Glucose Profiles Exemplified by an Examination of Blood Glucose Patterns in Patients with Type 1 and Type 2 Diabetes.

Kovatchev et al., Diabetes Technology & Therapeutics 5(5):817-828 (2003): Algorithmic Evaluation of Metabolic Control and Risk of Sever Hypoglycemia in Type 1 and Type 2 Diab Diabetes Using Self-Monitoring Blood Glucose Data.

McCall et al., Diabetes Technology & Therapeutics 8(6):644-653 (2006): A Novel Analytical Method for Assessing Glucose Variability: Using CGMS in Type 1 Diabetes Mellitus.

McCall et al., J.Diabetes Science & Technology 3(1):3-11 (Jan. 2009): The Median is Not the Only Message: A Clinicians Perspective on Mathematical Analysis of Glycemic Varia Variability and Modeling in Diabetes Mellitus.

Monnier et al., Diabetes Technology & Therapeutics 13(8):813-818 (2011): The Contribution of Glucose Variability to Asymptomatic Hypoglycemia in Persons with Type 2 Diabetes.

One Touch Verio Pro Blood Glucose Monitoring System Owners Booklet, pp. 71-76 (2010).

Rawlings et al., Diabetes Technology & Therapeutics 13(12):1241-1248 (2011): Translating Glucose Variability Metrics into the Clinica via Continuous Glucose Monitoring: A Graphical User Interface for Diabetes Evaluation (CGM-Guide).

Rodbard, Diabetes Technology & Therapeutics 11(9):551-565 (2009): New and Improved Methods to Characterize Glycemic Variability Using Continuous Glucose Monitoring.

Rodbard, Diabetes Technology & Therapeutics 11(Suppl. 1):S-55 to S67 (2009): Interpretation of Continuous Glucose Monitoring Data: Glycemic Variability and Quality of Glycemic Control.

Rodbard, Diabetes Technology & Therapeutics 13(11):1-4 (2011): Glycemic Variability: Measurement and Utility in Clinical Medicine and Research—One Viewpoint.

* cited by examiner

SYSTEMS AND METHODS FOR DETECTING GLUCOSE LEVEL DATA PATTERNS

CROSS-REFERENCE TO RELATED APPLICATIONS

This application claims the benefit of U.S. Provisional Appl. No. 61/515,786, filed Aug. 5, 2011, and U.S. Provisional Appl. No. 61/660,650, filed Jun. 15, 2012, the disclosure of which is hereby expressly incorporated by reference in its entirety and is hereby expressly made a portion of this application.

FIELD OF THE INVENTION

The embodiments relate generally to systems and methods for analyzing and detecting patterns in data received from an analyte sensor, such as a glucose sensor.

BACKGROUND OF THE INVENTION

Diabetes mellitus is a disorder in which the pancreas cannot create sufficient insulin (Type I or insulin dependent) and/or in which insulin is not effective (Type 2 or non-insulin dependent). In the diabetic state, the victim suffers from high blood sugar, which causes an array of physiological derangements (kidney failure, skin ulcers, or bleeding into the vitreous of the eye) associated with the deterioration of small blood vessels. A hypoglycemic reaction (low blood sugar) may be induced by an inadvertent overdose of insulin, or after a normal dose of insulin or glucose-lowering agent accompanied by extraordinary exercise or insufficient food intake.

Conventionally, a diabetic person carries a self-monitoring blood glucose (SMBG) monitor, which typically requires uncomfortable finger pricking methods. Due to the lack of comfort and convenience, a diabetic will normally only measure his or her glucose level two to four times per day. Unfortunately, these time intervals are spread so far apart that the diabetic will likely find out too late, sometimes incurring dangerous side effects, of a hyperglycemic or hypoglycemic condition. In fact, it is not only unlikely that a diabetic will take a timely SMBG value, but additionally the diabetic will not know if his blood glucose value is going up (higher) or down (lower) based on conventional methods.

Consequently, a variety of non-invasive, transdermal (e.g., transcutaneous) and/or implantable electrochemical sensors are being developed for continuously detecting and/or quantifying blood glucose values. These devices generally transmit raw or minimally processed data for subsequent analysis by the device or at a remote device, which can include a display.

Conventional processing of the raw data by a device are generally directed towards displaying information to the users regarding their recent glucose trend and helping them take short term actions, which in turn helps them stay in the target range and improves the average glucose over a period of time. Patients may also review data downloads either on their own or with their health care physician to decide on longer term behavioral changes.

However, some issues with conventional tools for analyzing data exist. Among these issues are the amount of time required to analyze the data and the lack of user participation in downloading or analyzing the data. For example, reviewing the downloads using trend graphs is time consuming and requires some amount of expertise to detect problem areas. Additionally, many users do not consider reviewing downloads, or even initiating downloads from the receivers, and are often unaware of some issues that may exist. Finally, conventional techniques may provide excessive alerts to the user, including alerts in response to measurements that do not pose a risk to the user. As a result, the user may ignore some important alerts which are provided by the conventional systems to their detriment.

SUMMARY OF THE INVENTION

Details of one or more implementations of the subject matter described in this specification are set forth in the accompanying drawings and the description below. Other features, aspects, and advantages will become apparent from the description, the drawings, and the claims. Note that the relative dimensions of the following figures may not be drawn to scale.

Accordingly, in a first aspect, an analyte concentration monitoring system is provided, comprising: a display screen; one or more processors; an input module configured to receive sensor data from an analyte sensor configured to generate sensor data points indicative of a measured an analyte concentration; memory; and one or more programs, wherein the one or more programs are stored in the memory and are configured to be executed by the one or more processors, the one or more programs including: instructions to apply a weighted value to each sensor data point falling within a timeframe of sensor data, the weighted value depending upon a concentration value of the sensor data; instructions to aggregate the weighted sensor data according to time of day; and instructions to display the aggregated, weighted sensor data on a chart.

In an embodiment of the first aspect or in combination with any other one or more embodiments of the first aspect, aggregating the sensor data according to time of day includes aggregating each sensor data point that falls within the same five minute interval of a day.

In an embodiment of the first aspect or in combination with any other one or more embodiments of the first aspect, the system further comprises instructions to highlight significant time ranges of the displayed sensor data, wherein significant time ranges of displayed data are determined based on exceeding thresholds for both frequency and severity.

In an embodiment of the first aspect or in combination with any other one or more embodiments of the first aspect, the determination of significant time ranges has an increased sensitivity during a predefined nighttime range of time, wherein increased sensitivity corresponds to lower frequency and severity thresholds.

In an embodiment of the first aspect or in combination with any other one or more embodiments of the first aspect, displaying the aggregated, weighted data includes displaying a high pattern chart and a low pattern chart, wherein sensor data associated with the high pattern chart are weighted differently than sensor data displayed in the low pattern chart.

In an embodiment of the first aspect or in combination with any other one or more embodiments of the first aspect, the chart includes an x-axis indicative of the timeframe and a y-axis indicative of a magnitude, wherein the y-axis scale is a predetermined percentage that less than a 100% of the maximum possible sum of weighted values.

In an embodiment of the first aspect or in combination with any other one or more embodiments of the first aspect, the system further comprises instructions to display a pattern summary table on the display, the pattern summary table indicating a total number of significant pattern matches and a description of one or more of the most significant matches, wherein the pattern matches are grouped into a plurality of categories corresponding to time of day and glucose level, wherein the most significant pattern match falling within in each of the four groups can is determined by based on a total sum of all contributed values within the pattern match interval.

In an embodiment of the first aspect or in combination with any other one or more embodiments of the first aspect, the system further comprises a user interface incorporating the display screen, wherein the user interface includes a timeframe selection control that allows a user to select of modify the timeframe.

In an embodiment of the first aspect or in combination with any other one or more embodiments of the first aspect, the timeframe selection control includes a user selectable drop down menu configured to allow a user to select or modify a number of days of the timeframe.

In an embodiment of the first aspect or in combination with any other one or more embodiments of the first aspect, the timeframe selection control includes a slider bar that a user can drag horizontally to modify the start and end dates of the timeframe.

In an embodiment of the first aspect or in combination with any other one or more embodiments of the first aspect, the chart is automatically updated based on modification of the timeframe using the timeframe selection control.

In a second aspect, a computer-implemented method is provided for identifying patterns in continuous analyte data, the method comprising: obtaining analyte data points from computer memory falling within a designated date range; applying one of more filters to the analyte data to generate contributor data points; weighting each the contributor data point based on the contributor data point's analyte value; assigning each weighted contributor data point to a matching epoch; identifying if an epoch is a match based on whether the contributor or contributors assigned to the epoch meet at least one pattern threshold; determining one or more patterns by scanning the epochs for flags; and outputting information representative of the determined one or more patterns.

In an embodiment of the second aspect or in combination with any other one or more embodiments of the second aspect, the designated date range is at least three days.

In an embodiment of the second aspect or in combination with any other one or more embodiments of the second aspect, the one or more filters comprises filters selected from the group consisting of: (i) an analyte value filter that filters out analyte data points that have an analyte concentration value falling outside of a predetermined analyte level or range of analyte values; (ii) a time range filter that filters out analyte data points measurements that falls outside of a time of day range; (iii) a day of the week filter that filters out analyte data points measured one or more predetermined days of the week; and (iv) an event filter that filters out data points that do not fall within a predetermined amount of time from an occurrence of an event.

In an embodiment of the second aspect or in combination with any other one or more embodiments of the second aspect, the event is an event selected from the group consisting of exercise, a meal, sleep and administration of a medication.

In an embodiment of the second aspect or in combination with any other one or more embodiments of the second aspect, the method further comprises receiving user input indicative of the event using a user interface.

In an embodiment of the second aspect or in combination with any other one or more embodiments of the second aspect, weighting each contributor data point is based on a predetermined weight assignment map or mathematical assignment function.

In an embodiment of the second aspect or in combination with any other one or more embodiments of the second aspect, weighting each contributor comprises assigning a weighted value to each contributor, wherein the assigned weighted value is smaller if the analyte value is less clinically significant than if the analyte value is more clinically significant.

In an embodiment of the second aspect or in combination with any other one or more embodiments of the second aspect, the assignment of weighted values is non-linear based on the analyte value.

In an embodiment of the second aspect or in combination with any other one or more embodiments of the second aspect, each epoch spans a determined time of day and wherein each contributor is added to the epoch that spans the corresponding time of day.

In an embodiment of the second aspect or in combination with any other one or more embodiments of the second aspect, the pattern thresholds comprise thresholds selected from the group consisting of: a threshold minimum number of contributors in an epoch; a threshold average weighted value of the contributors in an epoch; a threshold medium weighted value of the contributors in the epoch; a threshold sum of the weighted values of the contributors in the epoch; a threshold average difference of the weighted values of the contributors in the epoch; a threshold standard deviation value of the weighted values of the contributors in the epoch; and a threshold correlation value.

In an embodiment of the second aspect or in combination with any other one or more embodiments of the second aspect, at least one of the one or more pattern thresholds is defined in terms of a percentage.

In an embodiment of the second aspect or in combination with any other one or more embodiments of the second aspect, an epoch is flagged when at least some of the one or more thresholds are satisfied.

In an embodiment of the second aspect or in combination with any other one or more embodiments of the second aspect, determining the one or more patterns comprises determining a start and an end of the pattern.

In an embodiment of the second aspect or in combination with any other one or more embodiments of the second aspect, determining the start and the end of the pattern identifying a predetermined minimum number of contiguous matching epochs or a predetermined ratio of contiguous matching to non-matching epochs.

In an embodiment of the second aspect or in combination with any other one or more embodiments of the second aspect, the start of the pattern is determined based on identifying a first threshold number of contiguous matching epochs and the end of the pattern is determined based on identifying a second threshold number non-matching epochs.

In an embodiment of the second aspect or in combination with any other one or more embodiments of the second aspect, the outputted information comprises the start time and the end time.

In an embodiment of the second aspect or in combination with any other one or more embodiments of the second aspect, determining the one or more patterns is based on the frequency of matching epochs and the weighted values of the matching epochs.

In an embodiment of the second aspect or in combination with any other one or more embodiments of the second aspect, wherein the outputted information comprises a triggering alert notifying a user of the one or more detected patterns.

In an embodiment of the second aspect or in combination with any other one or more embodiments of the second aspect, the outputted information is processed further to form or modify a medication administration routine.

In a third aspect, an analyte concentration pattern detection system is provided which is configured to perform the method of the second aspect or any one or more of its associated embodiments, the system comprising a continuous analyte sensor to generate the analyte concentration data points, computer memory to store the generated analyte data points, a processor module configured to perform the applying, the weighting, the assigning, the identifying, and the determining.

In an embodiment of the third aspect, the system further comprises instructions stored in the memory, wherein the instructions, when executed by the processor module, cause the processor module to perform the applying, the weighting, the assigning, the identifying, and the determining.

In a fourth aspect, an analyte monitoring system is provided which is configured to measure an analyte concentration of a host, the system comprising: a sensor configured to generate sensor data indicative of a concentration of an analyte in a host over time; a memory configured to store the sensor data; a processor configured to receive the sensor data from at least one of the memory and detecting a pattern in the data, the detecting comprising identifying a plurality of events based on the sensor data, associating at least some of the plurality of events based on a criterion to from a set of events, and qualifying the set of events as the detected pattern; and an output module configured to output information representative of the detected pattern.

In an embodiment of the fourth aspect or in combination with any other one or more embodiments of the fourth aspect, the criterion is a timeframe.

In an embodiment of the fourth aspect or in combination with any other one or more embodiments of the fourth aspect, qualifying the set of events as a pattern comprises determining a priority score associated with the set.

In an embodiment of the fourth aspect or in combination with any other one or more embodiments of the fourth aspect, the set qualifies as a pattern if the priority score exceeds a threshold.

In an embodiment of the fourth aspect or in combination with any other one or more embodiments of the fourth aspect, the associating includes forming a plurality of sets, and wherein the set qualifies as a pattern if the priority score of the set is greater than a predetermined number of priority scores associated with the plurality of sets.

In an embodiment of the fourth aspect or in combination with any other one or more embodiments of the fourth aspect, the qualifying further comprises scoring each event in a set based on one or more scoring criteria, wherein the priority score is a summation of the scores associated with the events in the set.

In an embodiment of the fourth aspect or in combination with any other one or more embodiments of the fourth aspect, the scoring criteria comprising a time of day associated with the event, wherein events associated with certain predefined times of day are scored higher than events associated with other times of day.

In an embodiment of the fourth aspect or in combination with any other one or more embodiments of the fourth aspect, identifying the plurality of events comprises calculating an average distance for a segment of time of the sensor data that exceeds a first predetermined threshold analyte level.

In an embodiment of the fourth aspect or in combination with any other one or more embodiments of the fourth aspect, identifying the plurality of events further comprises comparing a total amount of time the segment exceeds a second predetermined threshold analyte level to a threshold amount of time.

In an embodiment of the fourth aspect or in combination with any other one or more embodiments of the fourth aspect, the first predetermined threshold analyte level and the second predetermined threshold analyte level are the same.

In an embodiment of the fourth aspect or in combination with any other one or more embodiments of the fourth aspect, the outputting comprises displaying the information representative of the detected pattern on a user interface, wherein the displaying comprises one or more of displaying a line graph depicting the detected pattern, highlighting a chart corresponding to the detected pattern and providing a timeframe in a textual format of a timeframe associated with the detected pattern.

In an embodiment of the fourth aspect or in combination with any other one or more embodiments of the fourth aspect, the system further comprises instructions stored in computer memory, wherein the instructions, when executed by the processor, cause the processor to perform the detecting and outputting.

In a fifth aspect, a method is provided for identifying patterns based on monitored analyte concentration sensor data, the method comprising: receiving data from at least one input, the data including measurements of an analyte concentration and time of day information associated with the measurement; analyzing the received data to identify a plurality of clinically significant events; determining patterns in the analyzed data, the determining comprising grouping the events based on time of day information into a plurality of event sets; and displaying information based on one or more of the determined patterns.

In an embodiment of the fifth aspect or in combination with any other one or more embodiments of the fifth aspect, the measurements are generated using a continuous analyte sensor.

In an embodiment of the fifth aspect or in combination with any other one or more embodiments of the fifth aspect, the method further comprises receiving user input indicating a timeframe and selecting the measurements that fall within the timeframe for the analyzing.

In an embodiment of the fifth aspect or in combination with any other one or more embodiments of the fifth aspect, the analyzing comprises detecting a plurality of episodes, wherein each of the plurality of episodes is detected by scanning the measurements using predefined criteria to determine a start and end of each episode.

In an embodiment of the fifth aspect or in combination with any other one or more embodiments of the fifth aspect, analyzing further comprises qualifying an episode as an event by filtering the episodes based on one or more episode characteristics.

In an embodiment of the fifth aspect or in combination with any other one or more embodiments of the fifth aspect, the characteristics comprise one or more of an average distance below a predetermined analyte level and a total time below a predetermined analyte level.

In an embodiment of the fifth aspect or in combination with any other one or more embodiments of the fifth aspect, grouping the events comprises calculating times between the events and grouping the events into sets based on the times.

In an embodiment of the fifth aspect or in combination with any other one or more embodiments of the fifth aspect, calculating the times between the events comprises calculating a time between the end of a first event and the end of a second event.

In an embodiment of the fifth aspect or in combination with any other one or more embodiments of the fifth aspect, calculating the times between the events comprises calculating a time between a nadir point of a first event and a nadir point of a second event.

In an embodiment of the fifth aspect or in combination with any other one or more embodiments of the fifth aspect, the determining further comprises selecting one or more sets as patterns, the selecting comprising filtering the plurality of sets based on a priority score of each group.

In an embodiment of the fifth aspect or in combination with any other one or more embodiments of the fifth aspect, the filtering filters out sets that have a priority score less than a threshold amount.

In an embodiment of the fifth aspect or in combination with any other one or more embodiments of the fifth aspect, the filtering filters out sets that have a priority score that is lower than the priority score of a predetermined number of other sets of the plurality of sets.

In an embodiment of the fifth aspect or in combination with any other one or more embodiments of the fifth aspect, the measurements are glucose concentration measurements and the events are hypoglycemic events.

In an embodiment of the fifth aspect or in combination with any other one or more embodiments of the fifth aspect, the displaying comprises displaying a timeframe corresponding to the at least one or more detected patterns.

In an embodiment of the fifth aspect or in combination with any other one or more embodiments of the fifth aspect, the method is performed automatically upon the expiration of a predetermined amount of time.

In an embodiment of the fifth aspect or in combination with any other one or more embodiments of the fifth aspect, the method is performed responsive to user input indicative of a request to initiate pattern detection.

In a sixth aspect, an analyte concentration pattern detection system is provided which is configured to perform the method according to the fifth aspect or any one or more of its associated embodiments, the system comprising a continuous analyte sensor to generate the analyte concentration measurements, computer memory to store the generated analyte concentration measurements, a processor module configured to perform the analyzing and determining, and a user interface configured to perform the displaying.

In an embodiment of the sixth aspect, the system further comprises instructions stored in the memory, wherein the instructions, when executed by the processor module, cause the processor module to perform the analyzing and determining.

In a seventh aspect, a method is provided for alerting a user based on measurements of an analyte concentration, the method comprising: receiving data from at least one input, the data including measurements of an analyte concentration and time of day information; analyzing the received data; detecting a hypoglycemic event based on the data exceeding at least one predetermined threshold; and displaying a trend graph of glucose measurements over time on a user interface, wherein the trend graph includes an indication of a hypoglycemic reoccurrence risk associated with a predetermined amount of time following the detected hypoglycemic event.

In an embodiment of the seventh aspect or in combination with any other one or more embodiments of the seventh aspect, detecting the hypoglycemia event comprises determining an average distance and a time a segment of time the measured analyte concentration is below a predetermined analyte concentration level.

In an embodiment of the seventh aspect or in combination with any other one or more embodiments of the seventh aspect, the method of Claim C1 is performed only when a user-selectable setting is turned on.

In an embodiment of the seventh aspect or in combination with any other one or more embodiments of the seventh aspect, the predetermined amount of time is 48 hours.

In an embodiment of the seventh aspect or in combination with any other one or more embodiments of the seventh aspect, the method further comprises triggering an audible or visual alert using the user interface responsive to detecting the hypoglycemic event and detecting that a current rate of change of the analyte concentration exceeds a predetermined threshold.

In an embodiment of the seventh aspect or in combination with any other one or more embodiments of the seventh aspect, the method further comprises triggering an audible or visual alert using the user interface responsive to detecting the hypoglycemic event and detecting that the current analyte concentration is below a predetermined threshold.

In an eighth aspect, an analyte concentration pattern detection system is provided which is configured to perform the method according to the seventh aspect or any one or more of its associated embodiments, the system comprising a continuous analyte sensor to generate the analyte concentration measurements, computer memory to store the generated analyte concentration measurements, a processor module configured to perform the detecting, and a user interface configured to perform the displaying.

In an embodiment of the eighth aspect, the system further comprises instructions stored in the memory, wherein the instructions, when executed by the processor module, cause the processor module to perform the detecting.

DETAILED DESCRIPTION OF THE EMBODIMENTS

Figure 1:
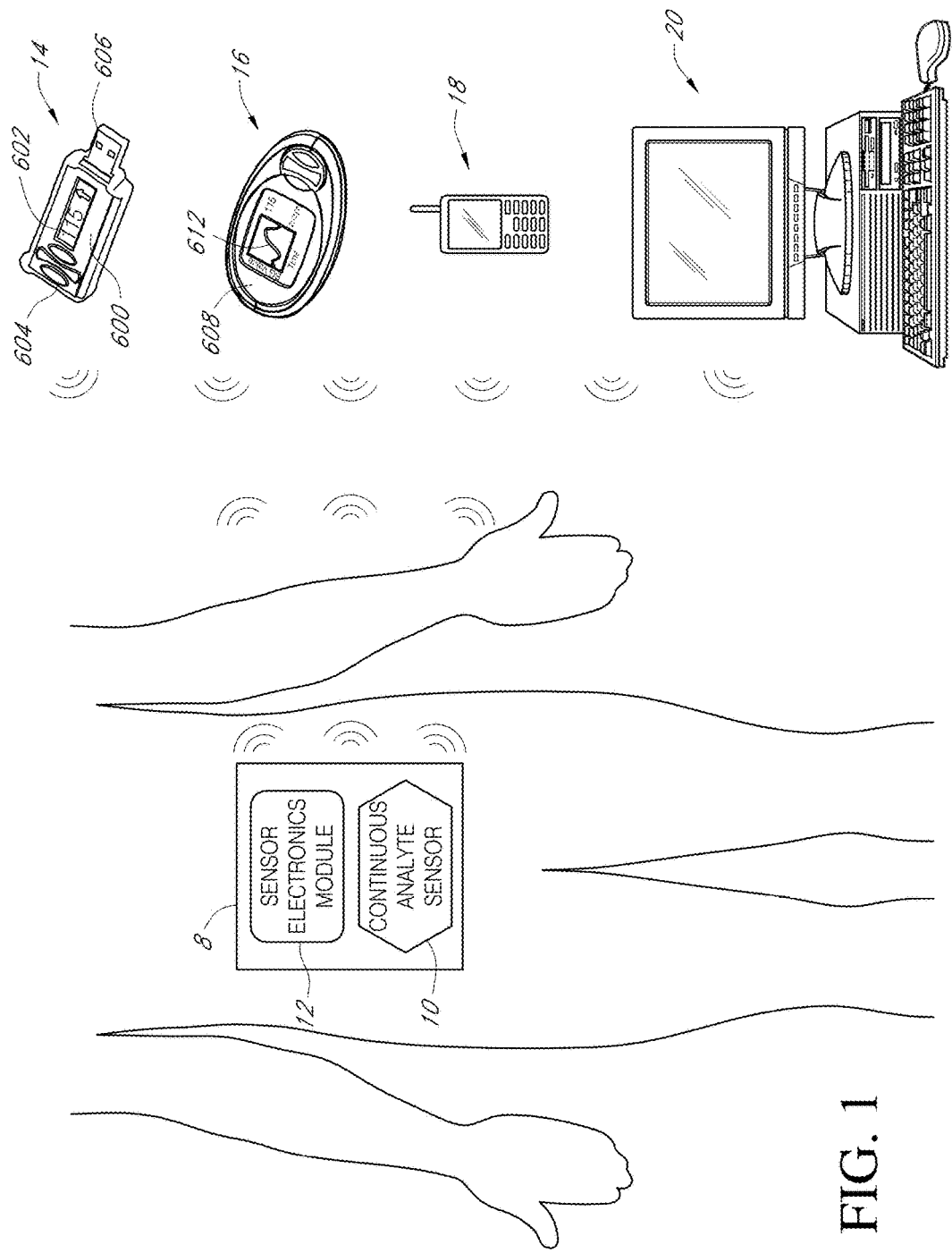
FIG. 1 is a diagram illustrating one embodiment of a continuous analyte sensor system including a sensor electronics module.

The following description and examples illustrate some exemplary embodiments of the disclosed invention in detail. Those of skill in the art will recognize that there are numerous variations and modifications of this invention that are encompassed by its scope. Accordingly, the description of a certain exemplary embodiment should not be deemed to limit the scope of the present invention.

Definitions

In order to facilitate an understanding of the systems and methods discussed herein, a number of terms are defined below. The terms defined below, as well as other terms used herein, should be construed to include the provided definitions, the ordinary and customary meaning of the terms, and any other implied meaning for the respective terms. Thus, the definitions below do not limit the meaning of these terms, but only provide exemplary definitions.

The term "analyte" as used herein is a broad term and is to be given its ordinary and customary meaning to a person of ordinary skill in the art (and is not to be limited to a special or customized meaning), and furthermore refers without limitation to a substance or chemical constituent in a biological fluid (for example, blood, interstitial fluid, cerebral spinal fluid, lymph fluid or urine) that can be analyzed. Analytes can include naturally occurring substances, artificial substances, metabolites, and/or reaction products. In some embodiments, the analyte for measurement by the sensor heads, devices, and methods is analyte. However, other analytes are contemplated as well, including but not limited to acarboxyprothrombin; acylcarnitine; adenine phosphoribosyl transferase; adenosine deaminase; albumin; alpha-fetoprotein; amino acid profiles (arginine (Krebs cycle), histidine/urocanic acid, homocysteine, phenylalanine/tyrosine, tryptophan); andrenostenedione; antipyrine; arabinitol enantiomers; arginase; benzoylecgonine (cocaine); biotinidase; biopterin; c-reactive protein; carnitine; carnosinase; CD4; ceruloplasmin; chenodeoxycholic acid; chloroquine; cholesterol; cholinesterase; conjugated 1-β hydroxy-cholic acid; cortisol; creatine kinase; creatine kinase MM isoenzyme; cyclosporin A; d-penicillamine; de-ethylchloroquine; dehydroepiandrosterone sulfate; DNA (acetylator polymorphism, alcohol dehydrogenase, alpha 1-antitrypsin, cystic fibrosis, Duchenne/Becker muscular dystrophy, analyte-6-phosphate dehydrogenase, hemoglobin A, hemoglobin S, hemoglobin C, hemoglobin D, hemoglobin E, hemoglobin F, D-Punjab, beta-thalassemia, hepatitis B virus, HCMV, HIV-1, HTLV-1, Leber hereditary optic neuropathy, MCAD, RNA, PKU, *Plasmodium vivax*, sexual differentiation, 21-deoxycortisol); desbutylhalofantrine; dihydropteridine reductase; diptheria/tetanus antitoxin; erythrocyte arginase; erythrocyte protoporphyrin; esterase D; fatty acids/acylglycines; free β-human chorionic gonadotropin; free erythrocyte porphyrin; free thyroxine (FT4); free tri-iodothyronine (FT3); fumarylacetoacetase; galactose/gal-1-phosphate; galactose-1-phosphate uridyltransferase; gentamicin; analyte-6-phosphate dehydrogenase; glutathione; glutathione perioxidase; glycocholic acid; glycosylated hemoglobin; halofantrine; hemoglobin variants; hexosaminidase A; human erythrocyte carbonic anhydrase I; 17-alpha-hydroxyprogesterone; hypoxanthine phosphoribosyl transferase; immunoreactive trypsin; lactate; lead; lipoproteins ((a), B/A-1, β); lysozyme; mefloquine; netilmicin; phenobarbitone; phenytoin; phytanic/pristanic acid; progesterone; prolactin; prolidase; purine nucleoside phosphorylase; quinine; reverse tri-iodothyronine (rT3); selenium; serum pancreatic lipase; sissomicin; somatomedin C; specific antibodies (adenovirus, anti-nuclear antibody, anti-zeta antibody, arbovirus, Aujeszky's disease virus, dengue virus, *Dracunculus medinensis*, *Echinococcus granulosus*, *Entamoeba histolytica*, enterovirus, *Giardia duodenalisa*, *Helicobacter pylori*, hepatitis B virus, herpes virus, HIV-1, IgE (atopic disease), influenza virus, *Leishmania donovani*, *leptospira*, measles/mumps/rubella, *Mycobacterium leprae*, *Mycoplasma pneumoniae*, Myoglobin, *Onchocerca volvulus*, parainfluenza virus, *Plasmodium falciparum*, poliovirus, *Pseudomonas aeruginosa*, respiratory syncytial virus, rickettsia (scrub typhus), *Schistosoma mansoni*, *Toxoplasma gondii*, *Trepenoma pallidium*, *Trypanosoma cruzi/rangeli*, vesicular stomatis virus, *Wuchereria bancrofti*, yellow fever virus); specific antigens (hepatitis B virus, HIV-1); succinylacetone; sulfadoxine; theophylline; thyrotropin (TSH); thyroxine (T4); thyroxine-binding globulin; trace elements; transferring; UDP-galactose-4-epimerase; urea; uroporphyrinogen I synthase; vitamin A; white blood cells; and zinc protoporphyrin. Salts, sugar, protein, fat, vitamins, and hormones naturally occurring in blood or interstitial fluids can also constitute analytes in certain embodiments. The analyte can be naturally present in the biological fluid, for example, a metabolic product, a hormone, an antigen, an antibody, and the like. Alternatively, the analyte can be introduced into the body, for example, a contrast agent for imaging, a radioisotope, a chemical agent, a fluorocarbon-based synthetic blood, or a drug or pharmaceutical composition, including but not limited to insulin; ethanol; cannabis (marijuana, tetrahydrocannabinol, hashish); inhalants (nitrous oxide, amyl nitrite, butyl nitrite, chlorohydrocarbons, hydrocarbons); cocaine (crack cocaine); stimulants (amphetamines, methamphetamines, Ritalin, Cylert, Preludin, Didrex, PreState, Voranil, Sandrex, Plegine); depressants (barbiturates, methaqualone, tranquilizers such as Valium, Librium, Miltown, Serax, Equanil, Tranxene); hallucinogens (phencyclidine, lysergic acid, mescaline, peyote, psilocybin); narcotics (heroin, codeine, morphine, opium, meperidine, Percocet, Percodan, Tussionex, Fentanyl, Darvon, Talwin, Lomotil); designer drugs (analogs of fentanyl, meperidine, amphetamines, methamphetamines, and phencyclidine, for example, Ecstasy); anabolic steroids; and nicotine. The metabolic products of drugs and pharmaceutical compositions are also contemplated analytes. Analytes such as neurochemicals and other chemicals generated within the body can also be analyzed, such as, for example, ascorbic acid, uric acid, dopamine, noradrenaline, 3-methoxytyramine (3MT), 3,4-Dihydroxyphenylacetic acid (DOPAC), Homovanillic acid (HVA), 5-Hydroxytryptamine (5HT), and 5-Hydroxyindoleacetic acid (FHIAA).

The term "A/D Converter" as used herein is a broad term and is to be given its ordinary and customary meaning to a person of ordinary skill in the art (and is not to be limited to a special or customized meaning), and furthermore refers without limitation to hardware and/or software that converts analog electrical signals into corresponding digital signals.

The terms "processor module," "microprocessor" and "processor" as used herein are broad terms and are to be given their ordinary and customary meaning to a person of ordinary skill in the art (and are not to be limited to a special or customized meaning), and furthermore refer without limitation to a computer system, state machine, and the like that performs arithmetic and logic operations using logic circuitry that responds to and processes the basic instructions that drive a computer.

The terms "sensor data", as used herein is a broad term and is to be given its ordinary and customary meaning to a person of ordinary skill in the art (and are not to be limited to a special or customized meaning), and furthermore refers without limitation to any data associated with a sensor, such as a continuous analyte sensor. Sensor data includes a raw data stream, or simply data stream, of analog or digital signal directly related to a measured analyte from an analyte sensor (or other signal received from another sensor), as well as calibrated and/or filtered raw data. In one example, the sensor data comprises digital data in "counts" converted by an A/D converter from an analog signal (e.g., voltage or amps) and includes one or more data points representative of a glucose concentration. Thus, the terms "sensor data point" and "data point" refer generally to a digital representation of sensor data at a particular time. The term broadly encompasses a plurality of time spaced data points from a sensor, such as a from a substantially continuous glucose sensor, which comprises individual measurements taken at time intervals ranging from fractions of a second up to, e.g., 1, 2, or 5 minutes or longer. In another example, the sensor data includes an integrated digital value representative of one or more data points averaged over a time period. Sensor data may include calibrated data, smoothed data, filtered data, transformed data, and/or any other data associated with a sensor.

The term "calibration" as used herein is a broad term and is to be given its ordinary and customary meaning to a person of ordinary skill in the art (and is not to be limited to a special or customized meaning), and furthermore refers without limitation to a process of determining a relationship between a raw data stream and corresponding reference data, which can be used to convert raw data into calibrated data (defined below). In some embodiments, such as continuous analyte sensors, for example, calibration can be updated or recalibrated over time as changes in the relationship between the raw data and reference data occur, for example, due to changes in sensitivity, baseline, transport, metabolism, and the like.

The terms "calibrated data" and "calibrated data stream" as used herein are broad terms and are to be given their ordinary and customary meaning to a person of ordinary skill in the art (and are not to be limited to a special or customized meaning), and furthermore refer without limitation to data that has been transformed from its raw state to another state using a function, for example a conversion function, to provide a meaningful value to a user.

The terms "smoothed data" and "filtered data" as used herein are broad terms and are to be given their ordinary and customary meaning to a person of ordinary skill in the art (and are not to be limited to a special or customized meaning), and furthermore refer without limitation to data that has been modified to make it smoother and more continuous and/or to remove or diminish outlying points, for example, by performing a moving average of the raw data stream. Examples of data filters include FIR (finite impulse response), IIR (infinite impulse response), moving average filters, and the like.

The terms "smoothing" and "filtering" as used herein are broad terms and are to be given their ordinary and customary meaning to a person of ordinary skill in the art (and are not to be limited to a special or customized meaning), and furthermore refer without limitation to a mathematical computation that attenuates or normalizes components of a signal, such as reducing noise errors in a raw data stream. In some embodiments, smoothing refers to modification of a data stream to make it smoother and more continuous or to remove or diminish outlying data points, for example, by performing a moving average of the raw data stream.

The term "noise signal" as used herein is a broad term and is to be given its ordinary and customary meaning to a person of ordinary skill in the art (and is not to be limited to a special or customized meaning), and furthermore refers without limitation to a signal associated with noise on the data stream (e.g., non-analyte related signal). The noise signal can be determined by filtering and/or averaging, for example. In some embodiments, the noise signal is a signal residual, delta residual (difference of residual), absolute delta residual, and/or the like, which are described in more detail elsewhere herein.

The term "algorithm" as used herein is a broad term and is to be given its ordinary and customary meaning to a person of ordinary skill in the art (and is not to be limited to a special or customized meaning), and furthermore refers without limitation to a computational process (associated with computer programming or other written instructions) involved in transforming information from one state to another.

The term "matched data pairs" as used herein is a broad term and is to be given its ordinary and customary meaning to a person of ordinary skill in the art (and is not to be limited to a special or customized meaning), and furthermore refers without limitation to reference data (for example, one or more reference analyte data points) matched with substantially time corresponding sensor data (for example, one or more sensor data points).

The term "counts" as used herein is a broad term and is to be given its ordinary and customary meaning to a person of ordinary skill in the art (and is not to be limited to a special or customized meaning), and furthermore refers without limitation to a unit of measurement of a digital signal. In one example, a raw data stream measured in counts is directly related to a voltage (e.g., converted by an A/D converter), which is directly related to current from the working electrode. In another example, counter electrode voltage measured in counts is directly related to a voltage.

The term "sensor" as used herein is a broad term and is to be given its ordinary and customary meaning to a person of ordinary skill in the art (and is not to be limited to a special or customized meaning), and furthermore refers without limitation to any device (or portion of a device) that measures a physical quantity and converts it into a signal that can be processed by analog and/or digital circuitry. Thus, the output of a sensor may be an analog and/or digital signal. Examples of sensors include analyte sensors, glucose sensors, temperature sensors, altitude sensors, accelerometers, and heart rate sensors.

The terms "glucose sensor" as used herein is a broad term and is to be given its ordinary and customary meaning to a person of ordinary skill in the art (and are not to be limited to a special or customized meaning), and furthermore refer without limitation to any sensor by which glucose can be quantified (e.g., enzymatic or non-enzymatic). For example, some embodiments of a glucose sensor may utilize a membrane that contains glucose oxidase that catalyzes the conversion of oxygen and glucose to hydrogen peroxide and gluconate, as illustrated by the following chemical reaction:

$$Glucose + O_2 \rightarrow Gluconate + H_2O_2$$

Because for each glucose molecule metabolized, there is a proportional change in the co-reactant $O_2$ and the product $H_2O_2$, one can use an electrode to monitor the current change in either the co-reactant or the product to determine glucose concentration.

The terms "coupled", "operably connected" and "operably linked" as used herein are broad terms and are to be given their ordinary and customary meaning to a person of ordinary skill in the art (and are not to be limited to a special or customized meaning), and furthermore refer without limitation to one or more components being linked to another component(s), either directly or indirectly, in a manner that allows transmission of signals between the components. For example, modules of a computing device that communicate via a common data bus are coupled to one another. As another example, one or more electrodes of a glucose sensor can be used to detect the amount of glucose in a sample and convert that information into a signal, e.g., an electrical or electromagnetic signal; the signal can then be transmitted to an electronic circuit. In this case, the electrode is "operably linked" to the electronic circuitry, even though the analog signal from the electrode is transmitted and/or transformed by analog and/or digital circuitry before reaching the electronic circuit. These terms are broad enough to include wireless connectivity.

The term "physically connected" as used herein is a broad term and is to be given its ordinary and customary meaning to a person of ordinary skill in the art (and are not to be limited to a special or customized meaning), and furthermore refers without limitation to one or more components that are connected to another component(s) through direct contact and/or a wired connection, including connecting via one or more intermediate physically connecting component (s). For example, a glucose sensor may be physically connected to a sensor electronics module, and thus the processor module located therein, either directly or via one or more electrical connections.

The term "substantially" as used herein is a broad term and is to be given its ordinary and customary meaning to a person of ordinary skill in the art (and is not to be limited to a special or customized meaning), and furthermore refers without limitation to being largely but not necessarily wholly that which is specified.

The term "host" as used herein is a broad term and is to be given its ordinary and customary meaning to a person of ordinary skill in the art (and is not to be limited to a special or customized meaning), and furthermore refers without limitation to mammal, such as a human implanted with a device.

The term "continuous analyte sensor" as used herein is a broad term and is to be given its ordinary and customary meaning to a person of ordinary skill in the art (and is not to be limited to a special or customized meaning), and furthermore refers without limitation to a device, or portion of a device, that continuously or continually measures a concentration of an analyte, for example, at time intervals ranging from fractions of a second up to, for example, 1, 2, or 5 minutes, or longer. In one exemplary embodiment, a glucose sensor comprises a continuous analyte sensor, such as is described in U.S. Pat. No. 7,310,544, which is incorporated herein by reference in its entirety.

The term "continuous analyte sensing" as used herein is a broad term and is to be given its ordinary and customary meaning to a person of ordinary skill in the art (and is not to be limited to a special or customized meaning), and furthermore refers without limitation to the period in which monitoring of an analyte is continuously or continually performed, for example, at time intervals ranging from fractions of a second up to, for example, 1, 2, or 5 minutes, or longer. In one embodiment, a glucose sensor performs continuous analyte sensing in order to monitor a glucose level in a corresponding host.

The terms "reference analyte monitor," "reference analyte meter," and "reference analyte sensor" as used herein are broad terms and are to be given their ordinary and customary meaning to a person of ordinary skill in the art (and are not to be limited to a special or customized meaning), and furthermore refer without limitation to a device that measures a concentration of an analyte and can be used as a reference for a continuous analyte sensor, for example a self-monitoring blood glucose meter (SMBG) can be used as a reference for a continuous glucose sensor for comparison, calibration, and the like.

The term "clinical acceptability", as used herein, is a broad term and is to be given its ordinary and customary meaning to a person of ordinary skill in the art (and is not to be limited to a special or customized meaning), and refers without limitation to determination of the risk of inaccuracies to a patient. Clinical acceptability may consider a deviation between time corresponding glucose measurements (e.g., data from a glucose sensor and data from a reference glucose monitor) and the risk (e.g., to the decision making of a diabetic patient) associated with that deviation based on the glucose value indicated by the sensor and/or reference data. One example of clinical acceptability may be 85% of a given set of measured analyte values within the "A" and "B" region of a standard Clarke Error Grid when the sensor measurements are compared to a standard reference measurement.

The term "quality of calibration" as used herein, is a broad term and is to be given its ordinary and customary meaning to a person of ordinary skill in the art (and is not to be limited to a special or customized meaning), and refers without limitation to the statistical association of matched data pairs in the calibration set used to create the conversion function. For example, an R-value may be calculated for a calibration set to determine its statistical data association, wherein an R-value greater than 0.79 determines a statistically acceptable calibration quality, while an R-value less than 0.79 determines statistically unacceptable calibration quality.

The term "sensor session" as used herein, is a broad term and is to be given its ordinary and customary meaning to a person of ordinary skill in the art (and is not to be limited to a special or customized meaning), and refers without limitation to a period of time a sensor is in use, such as but not limited to a period of time starting at the time the sensor is implanted (e.g., by the host) to removal of the sensor (e.g., removal of the sensor from the host's body and/or removal of the sensor electronics module from the sensor housing).

The terms "noise," "noise event(s)," "noise episode(s)," "signal artifact(s)," "signal artifact event(s)," and "signal artifact episode(s)" as used herein are broad terms and are to be given their ordinary and customary meaning to a person of ordinary skill in the art (and are not to be limited to a special or customized meaning), and furthermore refer without limitation to signal noise that is substantially non-glucose related, such as interfering species, macro- or micro-motion, ischemia, pH changes, temperature changes, pressure, stress, or even unknown sources of mechanical, electrical and/or biochemical noise for example.

The term "measured analyte values" as used herein is a broad term and is to be given its ordinary and customary meaning to a person of ordinary skill in the art (and is not to be limited to a special or customized meaning), and furthermore refers without limitation to an analyte value or set of analyte values for a time period for which analyte data has been measured by an analyte sensor. The term is broad enough to include sensor data from the analyte sensor before or after data processing in the sensor and/or receiver (for example, data smoothing, calibration, and the like).

The term "estimated analyte values" as used herein is a broad term and is to be given its ordinary and customary meaning to a person of ordinary skill in the art (and is not to be limited to a special or customized meaning), and furthermore refers without limitation to an analyte value or set of analyte values, which have been algorithmically extrapolated from measured analyte values. In some embodiments, estimated analyte values are estimated for a time period during which no data exists. However, estimated analyte values can also be estimated during a time period for which measured data exists, but is to be replaced by algorithmically extrapolated (e.g. processed or filtered) data due to noise or a time lag in the measured data, for example.

The term "calibration information" as used herein is a broad term and is to be given its ordinary and customary meaning to a person of ordinary skill in the art (and is not to be limited to a special or customized meaning), and furthermore refers without limitation to any information useful in calibration of a sensor. Calibration information may include reference data received from a reference analyte monitor, including one or more reference data points, one or more matched data pairs formed by matching reference data (e.g., one or more reference glucose data points) with substantially time corresponding sensor data (e.g., one or more continuous sensor data points), a calibration set formed from a set of one or more matched data pairs, a calibration line drawn from the calibration set, in vitro parameters (e.g., sensor sensitivity), and/or a manufacturing code, for example.

The term "alarm" as used herein is a broad term, and is to be given its ordinary and customary meaning to a person of ordinary skill in the art (and is not to be limited to a special or customized meaning), and furthermore refers without limitation to an alert or signal, such as an audible, visual, or tactile signal, triggered in response to one or more alarm conditions. In one embodiment, hyperglycemic and hypoglycemic alarms are triggered when present or predicted clinical danger is assessed based on continuous analyte data.

The term "transformed sensor data" as used herein is a broad term, and is to be given its ordinary and customary meaning to a person of ordinary skill in the art (and is not to be limited to a special or customized meaning), and furthermore refers without limitation to any data that is derived, either fully or in part, from raw sensor data from one or more sensors. For example, raw sensor data over a time period (e.g., 5 minutes) may be processed in order to generated transformed sensor data including one or more trend indicators (e.g., a 5 minute trend). Other examples of transformed data include filtered sensor data (e.g., one or more filtered analyte concentration values), calibrated sensor data (e.g., one or more calibrated analyte concentration values), rate of change information, trend information, rate of acceleration information, sensor diagnostic information, location information, alarm/alert information, calibration information, and/or the like.

The term "sensor information" as used herein is a broad term, and is to be given its ordinary and customary meaning to a person of ordinary skill in the art (and is not to be limited to a special or customized meaning), and furthermore refers without limitation to information associated with measurement, signal processing (including calibration), alarms, data transmission, and/or display associated with a sensor, such as a continuous analyte sensor. The term is broad enough to include raw sensor data (one or more raw analyte concentration values), as well as transformed sensor data. In some embodiments, sensor information includes displayable sensor information.

The term "displayable sensor information" as used herein is a broad term, and is to be given its ordinary and customary meaning to a person of ordinary skill in the art (and is not to be limited to a special or customized meaning), and furthermore refers without limitation to information that is transmitted for display on one or more display devices. As is discussed elsewhere herein, the content of displayable sensor information that is transmitted to a particular display device may be customized for the particular display device. Additionally, formatting of displayable sensor information may be customized for respective display devices. Displayable sensor information may include any sensor data, including raw sensor data, transformed sensor data, and/or any information associated with measurement, signal processing (including calibration), and/or alerts associated with one or more sensors.

The term "data package" as used herein is a broad term, and is to be given its ordinary and customary meaning to a person of ordinary skill in the art (and is not to be limited to a special or customized meaning), and furthermore refers without limitation to a combination of data that is transmitted to one or more display devices, such as in response to triggering of an alert. A data package may include displayable sensor information (e.g., that has been selected and formatted for a particular display device) as well as header information, such as data indicating a delivery address, communication protocol, etc. Depending on the embodiment, a data package may comprises multiple packets of data that are separately transmitted to a display device (and reassembled at the display device) or a single block of data that is transmitted to the display device. Data packages may be formatted for transmission via any suitable communication protocol, including radio frequency, Bluetooth, universal serial bus, any of the wireless local area network (WLAN) communication standards, including the IEEE 802.11, 802.15, 802.20, 802.22 and other 802 communication protocols, and/or a proprietary communication protocol.

The term "direct wireless communication" as used herein is a broad term, and is to be given its ordinary and customary meaning to a person of ordinary skill in the art (and is not to be limited to a special or customized meaning), and furthermore refers without limitation to a data transmission that goes from one device to another device without any intermediate data processing (e.g., data manipulation). For example, direct wireless communication between a sensor electronics module and a display device occurs when the sensor information transmitted from the sensor electronics module is received by the display device without intermediate processing of the sensor information. The term is broad enough to include wireless communication that is transmitted through a router, a repeater, a telemetry receiver (e.g., configured to re-transmit the sensor information without additional algorithmic processing), and the like. The term is also broad enough to include transformation of data format (e.g., via a Bluetooth receiver) without substantive transformation of the sensor information itself.

The term "prospective algorithm(s)" as used herein is a broad term, and is to be given its ordinary and customary meaning to a person of ordinary skill in the art (and is not to be limited to a special or customized meaning), and furthermore refers without limitation to algorithms that process sensor information in real-time (e.g., continuously and/or periodically as sensor data is received from the continuous analyte sensor) and provide real-time data output (e.g., continuously and/or periodically as sensor data is processed in the sensor electronics module).

The term "retrospective algorithm(s)" as used herein is a broad term, and is to be given its ordinary and customary meaning to a person of ordinary skill in the art (and is not to be limited to a special or customized meaning), and furthermore refers without limitation to algorithms that process sensor information in retrospect, (e.g., analysis of a set of data for a time period previous to the present time period).

As employed herein, the following abbreviations apply: Eq and Eqs (equivalents); mEq (milliequivalents); M (molar); mM (millimolar) μM (micromolar); N (Normal); mol (moles); mmol (millimoles); μmol (micromoles); nmol (nanomoles); g (grams); mg (milligrams); μg (micrograms); Kg (kilograms); L (liters); mL (milliliters); dL (deciliters); μL (microliters); cm (centimeters); mm (millimeters); μm (micrometers); nm (nanometers); h and hr (hours); min. (minutes); s and sec. (seconds); ° C. (degrees Centigrade).

Overview

In some embodiments, a system is provided for continuous measurement of an analyte in a host that includes: a continuous analyte sensor configured to continuously measure a concentration of the analyte in the host and a sensor electronics module physically connected to the continuous analyte sensor during sensor use. In one embodiment, the sensor electronics module includes electronics configured to process a data stream associated with an analyte concentration measured by the continuous analyte sensor in order to generate displayable sensor information that includes raw sensor data, transformed sensor data, and/or any other sensor data, for example. The sensor electronics module may further be configured to generate displayable sensor information that is customized for respective display devices, such that different display devices may receive different displayable sensor information.

Alerts

In some advantageous embodiments, one or more alerts are associated with a sensor electronics module. For example, alerts may be defined by one or more alert conditions that indicate when a respective alert should be triggered. For example, a hypoglycemic alert may include alert conditions indicating a glucose level below a threshold. The alert conditions may also be based on transformed or analyzed sensor data, such as trending data, pattern data, and/or sensor data from multiple different sensors (e.g. an alert may be based on sensor data from both a glucose sensor and a temperature sensor). For example, a hypoglycemic alert may include alert conditions indicating a minimum required trend in the host's glucose level that must be present before triggering the alert. The term "trend," as used herein refers generally to data indicating some attribute of data that is acquired over time, e.g., such as calibrated or filtered data from a continuous glucose sensor. A trend may indicate amplitude, rate of change, acceleration, direction, etc., of data, such as sensor data, including transformed or raw sensor data.

In one embodiment, each of the alerts is associated with one or more actions that are to be performed in response to triggering of the alert. Alert actions may include, for example, activating an alarm, such as displaying information on a display of the sensor electronics module or activating an audible or vibratory alarm coupled to the sensor electronics module, and/or transmitting data to one or more display devices external to the sensor electronics module. For any delivery action that is associated with a triggered alert, one or more delivery options define the content and/or format of the data to be transmitted, the device to which the data is to be transmitted, when the data is to be transmitted, and/or a communication protocol for delivery of the data.

In one embodiment, multiple delivery actions (each having respective delivery options) may be associated with a single alert such that displayable sensor information having different content and formatting, for example, is transmitted to respective display devices in response to triggering of a single alert. For example, a mobile telephone may receive a data package including minimal displayable sensor information (that may be formatted specifically for display on the mobile telephone), while a desktop computer may receive a data package including most (or all) of the displayable sensor information that is generated by the sensor electronics module in response to triggering of a common alert. Advantageously, the sensor electronics module is not tied to a single display device, rather it is configured to communicate with a plurality of different display devices directly, systematically, simultaneously (e.g., via broadcasting), regularly, periodically, randomly, on-demand, in response to a query, based on alerts or alarms, and/or the like.

In some embodiments, clinical risk alerts are provided that include alert conditions that combine intelligent and dynamic estimative algorithms that estimate present or predicted danger with greater accuracy, more timeliness in pending danger, avoidance of false alarms, and less annoyance for the patient. In general, clinical risk alerts include dynamic and intelligent estimative algorithms based on analyte value, rate of change, acceleration, clinical risk, statistical probabilities, known physiological constraints, and/or individual physiological patterns, thereby providing more appropriate, clinically safe, and patient-friendly alarms. Co-pending U.S. Publ. No. 2007-0208246-A1, which is incorporated herein by reference in its entirety, describes some systems and methods associated with the clinical risk alerts (or alarms) described herein. In some embodiments, clinical risk alerts can be triggered for a predetermined time period to allow for the user to attend to his/her condition. Additionally, the clinical risk alerts can be de-activated when leaving a clinical risk zone so as not to annoy the patient by repeated clinical alarms (e.g., visual, audible or vibratory), when the patient's condition is improving. In some embodiments, dynamic and intelligent estimation determines a possibility of the patient avoiding clinical risk, based on the analyte concentration, the rate of change, and other aspects of the dynamic and intelligent estimative algorithms. If there is minimal or no possibility of avoiding the clinical risk, a clinical risk alert will be triggered. However, if there is a possibility of avoiding the clinical risk, the system is configured to wait a predetermined amount of time and re-analyze the possibility of avoiding the clinical risk. In some embodiments, when there is a possibility of avoiding the clinical risk, the system is further configured to provide targets, therapy recommendations, or other information that can aid the patient in proactively avoiding the clinical risk.

In some embodiments, the sensor electronics module is configured to search for one or more display devices within communication range of the sensor electronics module and to wirelessly communicate sensor information (e.g., a data package including displayable sensor information, one or more alarm conditions, and/or other alarm information) thereto. Accordingly, the display device is configured to display at least some of the sensor information and/or alarm the host (and/or care taker), wherein the alarm mechanism is located on the display device.

In some embodiments, the sensor electronics module is configured to provide one or a plurality of different alarms via the sensor electronics module and/or via transmission of a data packaging indicating an alarm should be initiated by one or a plurality of display devices (e.g., sequentially and/or simultaneously). In some embodiments, the sensor electronics module determines which of the one or more alarms to trigger based on one or more alerts that are triggered. For example, when an alert triggers that indicates severe hypoglycemia, the sensor electronics module can perform multiple actions, such as activating an alarm on the sensor electronics module, transmitting a data package to a small (key fob) indicating activation of an alarm on the display, and transmitting a data package as a text message to a care provider. As an example, a text message can appear on a small (key fob) display, cell phone, pager device, and/or the like, including displayable sensor information that indicates the host's condition (e.g., "severe hypoglycemia").

In some embodiments, the sensor electronics module is configured to wait a time period for the host to respond to a triggered alert (e.g., by pressing or selecting a snooze and/or off function and/or button on the sensor electronics module and/or a display device), after which additional alerts are triggered (e.g., in an escalating manner) until one or more alerts are responded to. In some embodiments, the sensor electronics module is configured to send control signals (e.g., a stop signal) to a medical device associated with an alarm condition (e.g., hypoglycemia), such as an insulin pump, wherein the stop alert triggers a stop of insulin delivery via the pump.

In some embodiments, the sensor electronics module is configured to directly, systematically, simultaneously (e.g., via broadcasting), regularly, periodically, randomly, on-demand, in response to a query (from the display device), based on alerts or alarms, and/or the like transmit alarm information. In some embodiments, the system further includes a repeater such that the wireless communication distance of the sensor electronics module can be increased, for example, to 10, 20, 30, 50 75, 100, 150, or 200 meters or more, wherein the repeater is configured to repeat a wireless communication from the sensor electronics module to the display device located remotely from the sensor electronics module. A repeater can be useful to families having children with diabetes. For example, to allow a parent to carry, or place in a stationary position, a display device, such as in a large house wherein the parents sleep at a distance from the child.

Display Devices

In some embodiments, the sensor electronics module is configured to search for and/or attempt wireless communication with a display device from a list of display devices. In some embodiments, the sensor electronics module is configured to search for and/or attempt wireless communication with a list of display devices in a predetermined and/or programmable order (e.g., grading and/or escalating), for example, wherein a failed attempt at communication with and/or alarming with a first display device triggers an attempt at communication with and/or alarming with a second display device, and so on. In one exemplary embodiment, the sensor electronics module is configured to search for and attempt to alarm a host or care provider sequentially using a list of display devices, such as: 1) a default display device, 2) a key fob device, 3) a cell phone (via auditory and/or visual methods, such as, text message to the host and/or care provider, voice message to the host and/or care provider, and/or 911).

Depending on the embodiment, one or more display devices that receive data packages from the sensor electronics module are "dummy displays", wherein they display the displayable sensor information received from the sensor electronics module without additional processing (e.g., prospective algorithmic processing necessary for real-time display of sensor information). In some embodiments, the displayable sensor information comprises transformed sensor data that does not require processing by the display device prior to display of the displayable sensor information. Some display devices may comprise software including display instructions (software programming comprising instructions configured to display the displayable sensor information and optionally query the sensor electronics module to obtain the displayable sensor information) configured to enable display of the displayable sensor information thereon. In some embodiments, the display device is programmed with the display instructions at the manufacturer and can include security and/or authentication to avoid plagiarism of the display device. In some embodiments, a display device is configured to display the displayable sensor information via a downloadable program (for example, a downloadable Java Script via the internet), such that any display device that supports downloading of a program (for example, any display device that supports Java applets) therefore can be configured to display displayable sensor information (e.g., mobile phones, PDAs, PCs and the like).

In some embodiments, certain display devices may be in direct wireless communication with the sensor electronics module, however intermediate network hardware, firmware, and/or software can be included within the direct wireless communication. In some embodiments, a repeater (e.g., a Bluetooth repeater) can be used to re-transmit the transmitted displayable sensor information to a location farther away than the immediate range of the telemetry module of the sensor electronics module, wherein the repeater enables direct wireless communication when substantive processing of the displayable sensor information does not occur. In some embodiments, a receiver (e.g., Bluetooth receiver) can be used to re-transmit the transmitted displayable sensor information, possibly in a different format, such as in a text message onto a TV screen, wherein the receiver enables direct wireless communication when substantive processing of the sensor information does not occur. In one embodiment, the sensor electronics module directly wirelessly transmits displayable sensor information to one or a plurality of display devices, such that the displayable sensor information transmitted from the sensor electronics module is received by the display device without intermediate processing of the displayable sensor information.

In some embodiments, one or more sensors are configured to process data through communication with a "cloud" based processing system. For example, the applications for processing the sensor data may reside in one or more servers in communication with the sensor. The applications can be queried by the sensor for processing the data and determining trend or pattern information.

In one embodiment, one or more display devices comprise built-in authentication mechanisms, wherein authentication is required for communication between the sensor electronics module and the display device. In some embodiments, to authenticate the data communication between the sensor electronics module and display devices, a challenge-response protocol, such as a password authentication is provided, where the challenge is a request for the password and the valid response is the correct password, such that pairing of the sensor electronics module with the display devices can be accomplished by the user and/or manufacturer via the password. However, any known authentication system or method useful for telemetry devices can be used with the preferred embodiments.

In some embodiments, one or more display devices are configured to query the sensor electronics module for displayable sensor information, wherein the display device acts as a master device requesting sensor information from the sensor electronics module (e.g., a slave device) on-demand, for example, in response to a query. In some embodiments, the sensor electronics module is configured for periodic, systematic, regular, and/or periodic transmission of sensor information to one or more display devices (for example, every 1, 2, 5, or 10 minutes or more). In some embodiments, the sensor electronics module is configured to transmit data packages associated with a triggered alert (e.g., triggered by one or more alert conditions). However, any combination of the above described statuses of data transmission can be implemented with any combination of paired sensor electronics module and display device(s). For example, one or more display devices can be configured for querying the sensor electronics module database and for receiving alarm information triggered by one or more alarm conditions being met. Additionally, the sensor electronics module can be configured for periodic transmission of sensor information to one or more display devices (the same or different display devices as described in the previous example), whereby a system can include display devices that function differently with regard to how they obtain sensor information.

In some embodiments, as described in more detail elsewhere herein, a display device is configured to query the data storage memory in the sensor electronics module for certain types of data content, including direct queries into a database in the sensor electronics module's memory and/or requests for configured or configurable packages of data content therefrom; namely, the data stored in the sensor electronics module is configurable, queryable, predetermined, and/or pre-packaged, based on the display device with which the sensor electronics module is communicating. In some additional or alternative embodiments, the sensor electronics module generates the displayable sensor information based on its knowledge of which display device is to receive a particular transmission. Additionally, some display devices are capable of obtaining calibration information and wirelessly transmitting the calibration information to the sensor electronics module, such as through manual entry of the calibration information, automatic delivery of the calibration information, and/or an integral reference analyte monitor incorporated into the display device. U.S. Pat. No. 7,774,145, U.S. Publ. No. 2007-0203966-A1, U.S. Publ. No. 2007-0208245-A1, and U.S. Pat. No. 7,519,408, each of which is incorporated herein by reference in its entirety, describe systems and methods for providing an integral reference analyte monitor incorporated into a display device and/or other calibration methods that can be implemented with the preferred embodiments.

In general, a plurality of display devices (e.g., a small (key fob) display device, a larger (hand-held) display device, a mobile phone, a reference analyte monitor, a drug delivery device, a medical device and a personal computer) are configured to wirelessly communicate with the sensor electronics module, wherein the one or more display devices are configured to display at least some of the displayable sensor information wirelessly communicated from the sensor electronics module, wherein displayable sensor information includes sensor data, such as raw data and/or transformed sensor data, such as analyte concentration values, rate of change information, trend information, alert information, sensor diagnostic information and/or calibration information, for example.

Small (Key Fob) Display Device

In some embodiments, one the plurality of display devices is a small (e.g., key fob) display device 14 (FIG. 1) that is configured to display at least some of the sensor information, such as an analyte concentration value and a trend arrow. In general, a key fob device is a small hardware device with a built-in authentication mechanism sized to fit on a key chain. However, any small display device 14 can be configured with the functionality as described herein with reference to the key fob device 14, including a wrist band, a hang tag, a belt, a necklace, a pendent, a piece of jewelry, an adhesive patch, a pager, an identification (ID) card, and the like, all of which are included by the phrase "small display device" and/or "key fob device" herein.

In general, the key fob device 14 includes electronics configured to receive and display displayable sensor information (and optionally configured to query the sensor electronics module for the displayable sensor information). In one embodiment, the electronics include a RAM and a program storage memory configured at least to display the sensor data received from the sensor electronics module. In some embodiments, the key fob device 14 includes an alarm configured to warn a host of a triggered alert (e.g., audio, visual and/or vibratory). In some embodiments, the key fob device 14 includes a user interface, such as an LCD 602 and one or more buttons 604 that allows a user to view data, such as a numeric value and/or an arrow, to toggle through one or more screens, to select or define one or more user parameters, to respond to (e.g., silence, snooze, turn off) an alert, and/or the like.

In some embodiments, the key fob display device has a memory (e.g., such as in a gig stick or thumb drive) that stores sensor, drug (e.g., insulin) and other medical information, enabling a memory stick-type function that allows data transfer from the sensor electronics module to another device (e.g., a PC) and/or as a data back-up location for the sensor electronics module memory (e.g., data storage memory). In some embodiments, the key fob display device is configured to be automatically readable by a network system upon entry into a hospital or other medical complex.

In some embodiments, the key fob display device includes a physical connector, such as USB port 606, to enable connection to a port (e.g., USB) on a computer, enabling the key fob to function as a data download device (e.g., from the sensor electronics module to a PC), a telemetry connector (e.g., Bluetooth adapter/connector for a PC), and/or enables configurable settings on the key fob device (e.g., via software on the PC that allows configurable parameters such as numbers, arrows, trend, alarms, font, etc.) In some embodiments, user parameters associated with the small (key fob) display device can be programmed into (and/or modified) by a display device such as a personal computer, personal digital assistant, or the like. In one embodiment, user parameters include contact information, alert/alarms settings (e.g., thresholds, sounds, volume, and/or the like), calibration information, font size, display preferences, defaults (e.g., screens), and/or the like. Alternatively, the small (key fob) display device can be configured for direct programming of user parameters. In some embodiments, wherein the small (key fob) display device comprises a telemetry module, such as Bluetooth, and a USB connector (or the like), such that the small (key fob) display device additionally functions as telemetry adapter (e.g., Bluetooth adapter) enabling direct wireless communication between the sensor electronics module and the PC, for example, wherein the PC does not include the appropriate telemetry adapter therein.

Large (Hand-Held) Display Device

In some embodiments, one the plurality of display devices is a hand-held display device 16 (FIG. 1) configured to display sensor information including an analyte concentration and a graphical representation of the analyte concentration over time. In general, the hand-held display device comprises a display 608 sufficiently large to display a graphical representation 612 of the sensor data over a time period, such as a previous 1, 3, 5, 6, 9, 12, 18, or 24-hours of sensor data. In some embodiments, the hand-held device 16 is configured to display a trend graph or other graphical representation, a numeric value, an arrow, and/or to alarm the host. U.S. Publ. No. 2005-0203360-A1, which is incorporated herein by reference in its entirety, describes and illustrates some examples of display of data on a hand-held display device. Although FIG. 1 illustrates one embodiment of a hand-held display device, the hand-held device can be any single application device or multi-application device, such as mobile phone, a palm-top computer, a PDA, portable media player (e.g., iPod, MP3 player), a blood glucose meter, an insulin pump, and/or the like.

In some embodiments, a mobile phone (or PDA) is configured to display (as described above) and/or relay sensor information, such as via a voice or text message to the host and/or the host's care provider. In some embodiments, the mobile phone further comprises an alarm configured to warn a host of a triggered alert, such as in response to receiving a data package indicating triggering of the alert. Depending on the embodiment, the data package may include displayable sensor information, such as an on-screen message, text message, and/or pre-generated graphical representation of sensor data and/or transformed sensor data, as well as an indication of an alarm, such as an auditory alarm or a vibratory alarm, that should be activated by the mobile phone.

In some embodiments, one of the display devices is a drug delivery device, such as an insulin pump and/or insulin pen, configured to display sensor information. In some embodiments, the sensor electronics module is configured to wirelessly communicate sensor diagnostic information to the drug delivery device in order to enable to the drug delivery device to consider (include in its calculations/algorithms) a quality, reliability and/or accuracy of sensor information for closed loop and/or semi-closed loop systems, which are described in more detail in U.S. Pat. No. 7,591,801, which is incorporated herein by reference in its entirety. In some alternative embodiments, the sensor electronic module is configured to wirelessly communicate with a drug delivery device that does not include a display, for example, in order to enable a closed loop and/or semi-closed loop system as described above.

In some embodiments, one of the display devices is a drug delivery device is a reference analyte monitor, such as a blood glucose meter, configured to measure a reference analyte value associated with an analyte concentration in a biological sample from the host.

Personal Computer Display Device

In some embodiments, one of the display devices is personal computer (PC) 20 (FIG. 1) configured to display sensor information. Preferably, the PC 20 has software installed, wherein the software enables display and/or performs data analysis (retrospective processing) of the historic sensor information. In some embodiments, a hardware device can be provided (not shown), wherein the hardware device (e.g., dongle/adapter) is configured to plug into a port on the PC to enable wireless communication between the sensor electronics module and the PC. In some embodiments, the PC 20 is configured to set and/or modify configurable parameters of the sensor electronics module 12 and/or small (key fob device) 14, as described in more detail elsewhere herein.

Other Display Devices

In some embodiments, one of the display devices is an on-skin display device that is splittable from, releasably attached to, and/or dockable to the sensor housing (mounting unit, sensor pod, or the like). In some embodiments, release of the on-skin display turns the sensor off; in other embodiments, the sensor housing comprises sufficient sensor electronics to maintain sensor operation even when the on-skin display is released from the sensor housing.

In some embodiments, one of the display devices is a secondary device, such as a heart rate monitor, a pedometer, a temperature sensor, a car initialization device (e.g., configured to allow or disallow the car to start and/or drive in response to at least some of the sensor information wirelessly communicated from the sensor electronics module (e.g., glucose value above a predetermined threshold)). In some alternative embodiments, one of the display devices is designed for an alternative function device (e.g., a caller id device), wherein the system is configured to communicate with and/or translate displayable sensor information to a custom protocol of the alternative device such that displayable sensor information can be displayed on the alternative function device (display of caller id device).

Exemplary Configurations

FIG. 1 is a diagram illustrating one embodiment of a continuous analyte sensor system 8 including a sensor electronics module 12. In the embodiment of FIG. 1, the system includes a continuous analyte sensor 10 physically connected to a sensor electronics module 12, which is in direct wireless communication with a plurality of different display devices 14, 16, 18, and/or 20.

In one embodiment, the sensor electronics module 12 includes electronic circuitry associated with measuring and processing the continuous analyte sensor data, including prospective algorithms associated with processing and calibration of the sensor data. The sensor electronics module 12 may be physically connected to the continuous analyte sensor 10 and can be integral with (non-releasably attached to) or releasably attachable to the continuous analyte sensor 10. The sensor electronics module 12 may include hardware, firmware, and/or software that enables measurement of levels of the analyte via a glucose sensor, such as an analyte sensor. For example, the sensor electronics module 12 can include a potentiostat, a power source for providing power to the sensor, other components useful for signal processing and data storage, and a telemetry module for transmitting data from the sensor electronics module to one or more display devices. Electronics can be affixed to a printed circuit board (PCB), or the like, and can take a variety of forms. For example, the electronics can take the form of an integrated circuit (IC), such as an Application-Specific Integrated Circuit (ASIC), a microcontroller, and/or a processor. The sensor electronics module 12 includes sensor electronics that are configured to process sensor information, such as sensor data, and generate transformed sensor data and displayable sensor information. Examples of systems and methods for processing sensor analyte data are described in more detail herein and in U.S. Pat. No. 7,310,544, 6,931, 327, 8,010,174, 8,233,959, U.S. Publ. No. 2007-0032706-A1, U.S. Publ. No. 2008-0033254-A1, U.S. Publ. No. 2005-0203360-A1, U.S. Publ. No. 2005-0154271-A1, U.S. Publ. No. 2005-0192557-A1, U.S. Publ. No. 2006-0222566-A1, U.S. Publ. No. 2007-0203966-A1, and U.S. Publ. No. 2007-0208245, each of which is incorporated herein by reference in their entirety.

Referring again to FIG. 1, a plurality of display devices (14, 16, 18, and/or 20) are configured for displaying (and/or alarming) the displayable sensor information that has been transmitted by the sensor electronics module 12 (e.g., in a customized data package that is transmitted to the display devices based on their respective preferences). For example, the display devices are configured to display the displayable sensor information as it is communicated from the sensor electronics module (e.g., in a data package that is transmitted to respective display devices), without any additional prospective processing required for calibration and real-time display of the sensor data.

In the embodiment of FIG. 1, the plurality of display devices includes a small (key fob) display device 14, such as a wrist watch, a belt, a necklace, a pendent, a piece of jewelry, an adhesive patch, a pager, a key fob, a plastic card (e.g., credit card), an identification (ID) card, and/or the like, wherein the small display device comprises a relatively small display (e.g., smaller than the large display device) and is configured to display certain types of displayable sensor information (e.g., a numerical value and an arrow, in some embodiments). In some embodiments, one of the plurality of display devices is a large (hand-held) display device 16, such as a hand-held receiver device, a palm-top computer and/or the like, wherein the large display device comprises a relatively larger display (e.g., larger than the small display device) and is configured to display a graphical representation of the continuous sensor data (e.g., including current and historic data). Other display devices can include other hand-held devices, such as a cell phone or PDA 18, an insulin delivery device, a blood glucose meter, and/or a desktop or laptop computer 20.

Because different display devices provide different user interfaces, content of the data packages (e.g., amount, format, and/or type of data to be displayed, alarms, and the like) can be customized (e.g., programmed differently by the manufacture and/or by an end user) for each particular display device. Accordingly, in the embodiment of FIG. 1, a plurality of different display devices are in direct wireless communication with the sensor electronics module (e.g., such as an on-skin sensor electronics module 12 that is physically connected to the continuous analyte sensor 10) during a sensor session to enable a plurality of different types and/or levels of display and/or functionality associated with the displayable sensor information, which is described in more detail elsewhere herein.

Continuous Sensor

In some embodiments, a glucose sensor comprises a continuous sensor, for example a subcutaneous, transdermal (e.g., transcutaneous), or intravascular device. In some embodiments, the device can analyze a plurality of intermittent blood samples. The glucose sensor can use any method of glucose-measurement, including enzymatic, chemical, physical, electrochemical, spectrophotometric, polarimetric, calorimetric, iontophoretic, radiometric, immunochemical, and the like.

A glucose sensor can use any known method, including invasive, minimally invasive, and non-invasive sensing techniques (e.g., fluorescent monitoring), to provide a data stream indicative of the concentration of glucose in a host. The data stream is typically a raw data signal, which is converted into a calibrated and/or filtered data stream that is used to provide a useful value of glucose to a user, such as a patient or a caretaker (e.g., a parent, a relative, a guardian, a teacher, a doctor, a nurse, or any other individual that has an interest in the wellbeing of the host).

A glucose sensor can be any device capable of measuring the concentration of glucose. One exemplary embodiment is described below, which utilizes an implantable glucose sensor. However, it should be understood that the devices and methods described herein can be applied to any device capable of detecting a concentration of glucose and providing an output signal that represents the concentration of glucose.

In one embodiment, the analyte sensor is an implantable glucose sensor, such as described with reference to U.S. Pat. No. 6,001,067 and U.S. Publ. No. 2005-0027463-A1. In another embodiment, the analyte sensor is a transcutaneous glucose sensor, such as described with reference to U.S. Publ. No. 2006-0020187-A1. In some alternative embodiments, an optical, non-invasive, "continuous or quasi-continuous" glucose measurement device such as described by U.S. Pat. No. 6,049,727, which is incorporated by reference herein in its entirety, can be implanted in the body for optically measuring analyte levels.

In still other embodiments, the sensor is configured to be implanted in a host vessel or extracorporeally, such as is described in U.S. Publ. No. 2007-0027385-A1, U.S. Publ. No. 2008-0119703-A1, U.S. Publ. No. 2008-0108942-A1, and U.S. Publ. No. 2007-0197890-A1, the contents of each of which is hereby incorporated by reference in its entirety. In one alternative embodiment, the continuous glucose sensor comprises a transcutaneous sensor such as described in U.S. Pat. No. 6,565,509 to Say et al., for example. In another alternative embodiment, the continuous glucose sensor comprises a subcutaneous sensor such as described with reference to U.S. Pat. No. 6,579,690 to Bonnecaze et al. or U.S. Pat. No. 6,484,046 to Say et al., for example. In another alternative embodiment, the continuous glucose sensor comprises a refillable subcutaneous sensor such as described with reference to U.S. Pat. No. 6,512,939 to Colvin et al., for example. In another alternative embodiment, the continuous glucose sensor comprises an intravascular sensor such as described with reference to U.S. Pat. No. 6,477,395 to Schulman et al., for example. In another alternative embodiment, the continuous glucose sensor comprises an intravascular sensor such as described with reference to U.S. Pat. No. 6,424,847 to Mastrototaro et al., for example.

Figure 2A:
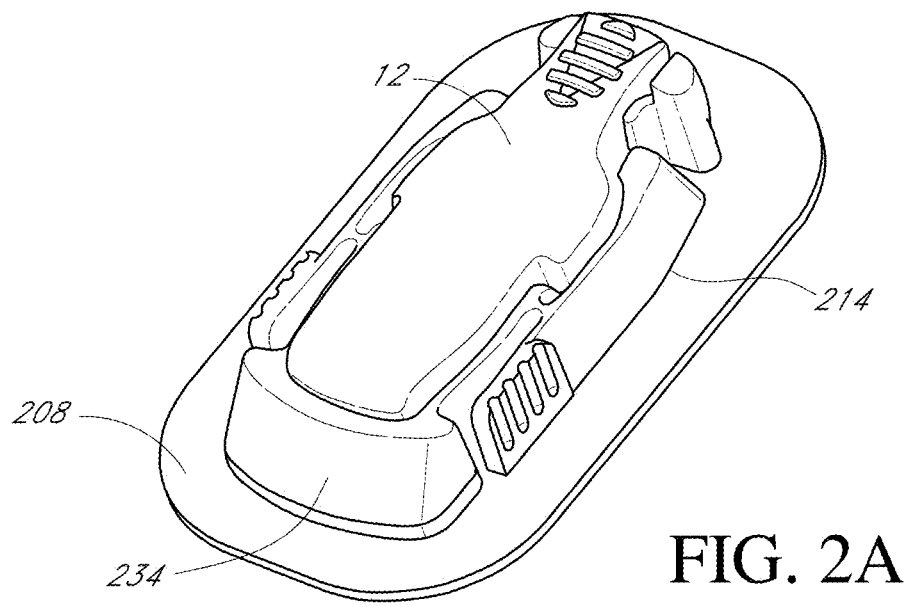
FIG. 2A is a perspective view of a sensor system including a mounting unit and sensor electronics module attached thereto according to one embodiment.
Figure 2B:
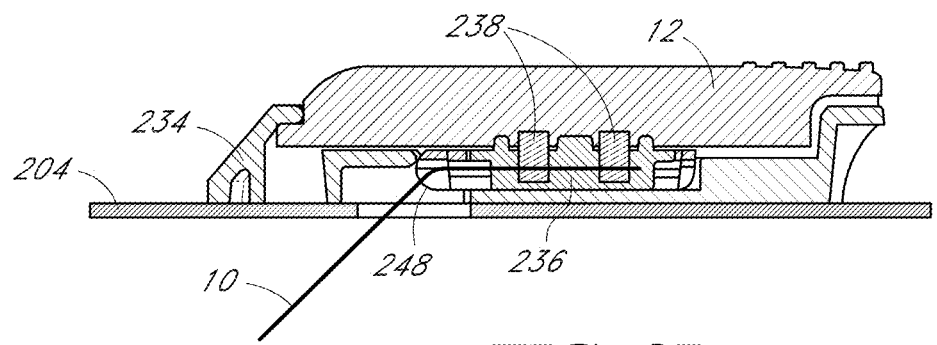
FIG. 2B is a side view of the sensor system of FIG. 2B.

FIGS. 2A and 2B are perspective and side views of a sensor system including a mounting unit 214 and sensor electronics module 12 attached thereto in one embodiment, shown in its functional position, including a mounting unit and a sensor electronics module matingly engaged therein. In some embodiments, the mounting unit 214, also referred to as a housing or sensor pod, comprises a base 234 adapted for fastening to a host's skin. The base can be formed from a variety of hard or soft materials, and can comprises a low profile for minimizing protrusion of the device from the host during use. In some embodiments, the base 234 is formed at least partially from a flexible material, which is believed to provide numerous advantages over conventional transcutaneous sensors, which, unfortunately, can suffer from motion-related artifacts associated with the host's movement when the host is using the device. The mounting unit 214 and/or sensor electronics module 12 can be located over the sensor insertion site to protect the site and/or provide a minimal footprint (utilization of surface area of the host's skin).

In some embodiments, a detachable connection between the mounting unit 214 and sensor electronics module 12 is provided, which enables improved manufacturability, namely, the relatively inexpensive mounting unit 214 can be disposed of when replacing the sensor system after its usable life, while the relatively more expensive sensor electronics module 12 can be reusable with multiple sensor systems. In some embodiments, the sensor electronics module 12 is configured with signal processing (programming), for example, configured to filter, calibrate and/or other algorithms useful for calibration and/or display of sensor information. However, an integral (non-detachable) sensor electronics module can be configured.

In some embodiments, the contacts 238 are mounted on or in a subassembly hereinafter referred to as a contact subassembly 236 configured to fit within the base 234 of the mounting unit 214 and a hinge 248 that allows the contact subassembly 236 to pivot between a first position (for insertion) and a second position (for use) relative to the mounting unit 214. The term "hinge" as used herein is a broad term and is used in its ordinary sense, including, without limitation, to refer to any of a variety of pivoting, articulating, and/or hinging mechanisms, such as an adhesive hinge, a sliding joint, and the like; the term hinge does not necessarily imply a fulcrum or fixed point about which the articulation occurs. In some embodiments, the contacts 238 are formed from a conductive elastomeric material, such as a carbon black elastomer, through which the sensor 10 extends.

In certain embodiments, the mounting unit 214 is provided with an adhesive pad 208, disposed on the mounting unit's back surface and includes a releasable backing layer. Thus, removing the backing layer and pressing the base portion 234 of the mounting unit onto the host's skin adheres the mounting unit 214 to the host's skin. Additionally or alternatively, an adhesive pad can be placed over some or all of the sensor system after sensor insertion is complete to ensure adhesion, and optionally to ensure an airtight seal or watertight seal around the wound exit-site (or sensor insertion site) (not shown). Appropriate adhesive pads can be chosen and designed to stretch, elongate, conform to, and/or aerate the region (e.g., host's skin). The embodiments described with reference to FIGS. 2A and 2B are described in more detail with reference to U.S. Pat. No. 7,310,544, which is incorporated herein by reference in its entirety. Configurations and arrangements can provide water resistant, waterproof, and/or hermetically sealed properties associated with the mounting unit/sensor electronics module embodiments described herein.

Various methods and devices that are suitable for use in conjunction with aspects of some embodiments are disclosed in U.S. Publ. No. 2009-0240120-A1, which is incorporated herein by reference in its entirety.

Use of Standardized Data Communication Protocols

Figure 3:
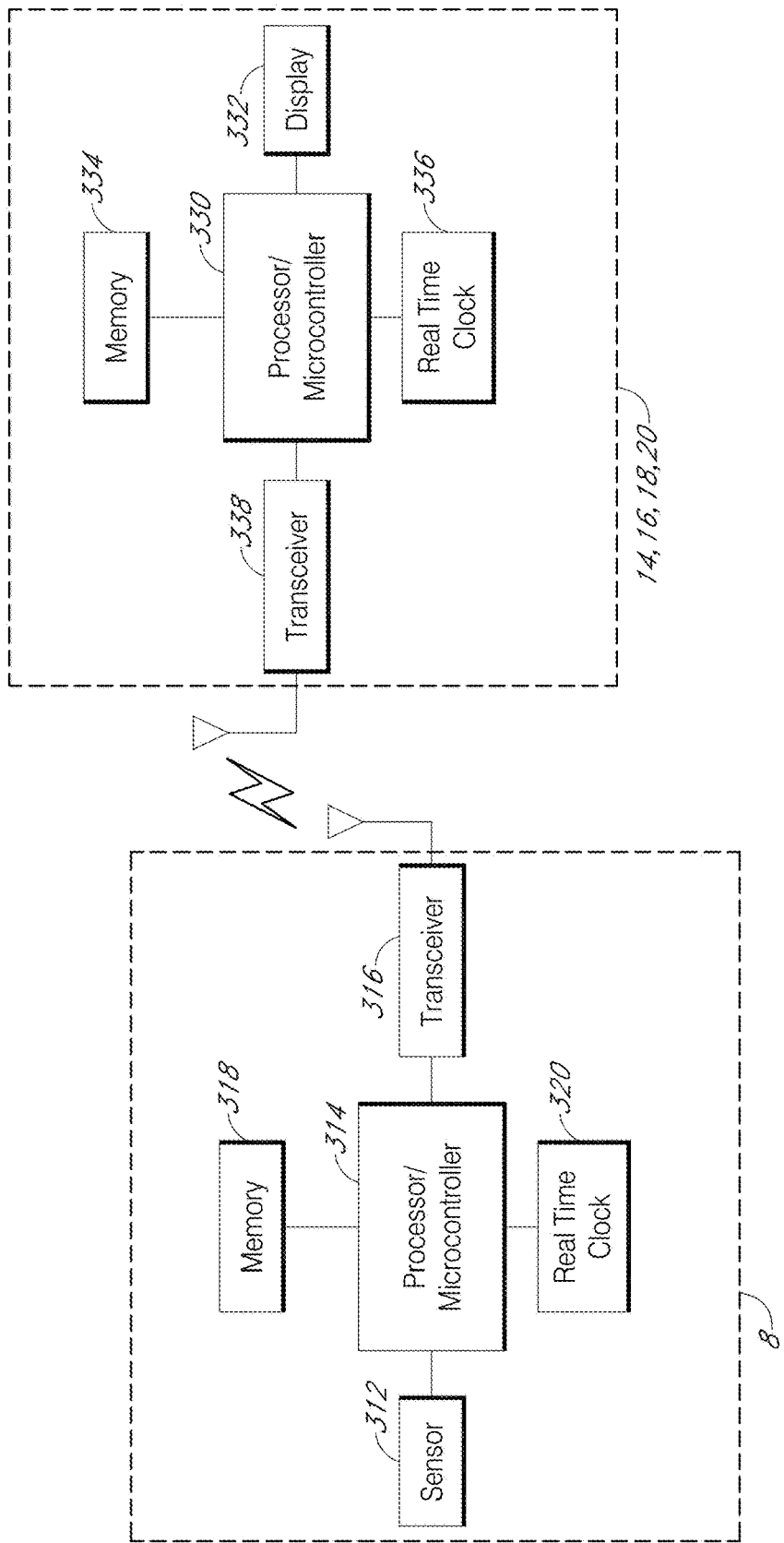
FIG. 3 is an exemplary block diagram illustrating various elements of one embodiment of a continuous analyte sensor system and display device.

FIG. 3 is an exemplary block diagram illustrating various elements of one embodiment of a continuous analyte sensor system 8 and display device 14, 16, 18, 20. The sensor system 8 may include a sensor 312 (also designated 10 in FIG. 1) coupled to a processor 314 (part of item 12 in FIG. 1) for processing and managing sensor data. The processor may be further coupled to a transceiver 316 (part of item 12 in FIG. 1) for sending sensor data and receiving requests and commands from an external device, such as the display device 14, 16, 18, 20, which is used to display or otherwise provide the sensor data to a user. The sensor system 8 may further include a memory 318 (part of item 12 in FIG. 1) and a real time clock 320 (part of item 12 in FIG. 1) for storing and tracking sensor data. Communication protocols and associated modulation schemes such as Bluetooth, Zigbee™, or ANT™ for example may be used to transmit and receive data between the sensor system 8 and the display device 14, 16, 18, 20.

The display device 14, 16, 18, 20 may be used for alerting and providing sensor information to a user, and may include a processor 330 for processing and managing sensor data. The display device 14, 16, 18, 20 may include a display 332, a memory 334, and a real time clock 336 for displaying, storing and tracking sensor data respectively. The display device 14, 16, 18, 20 may further include a transceiver 338 for receiving sensor data and for sending requests, instructions, and data to the sensor system 8. The transceiver 338 may further employ the communication protocols described above including, but not limited to, radio frequency, Bluetooth, BTLE, Zigbee™, ANT™, etc.

In some embodiments, when a standardized communication protocol is used such as Bluetooth or ANT, commercially available transceiver circuits may be utilized that incorporate processing circuitry to handle low level data communication functions such as the management of data encoding, transmission frequencies, handshake protocols, and the like. In these embodiments, the processor 314, 330 does not need to manage these activities, but rather provides desired data values for transmission, and manages high level functions such as power up or down, set a rate at which messages are transmitted, and the like. Instructions and data values for performing these high level functions can be provided to the transceiver circuits via a data bus and transfer protocol established by the manufacturer of the transceiver circuit.

The analyte sensor system 8 gathers analyte data that it periodically sends to the display device 14, 16, 18, 20. Rather than having the transmission and receiving circuitry continuously communicating, the analyte sensor system 8 and display device 14, 16, 18, 20 periodically establish a communication channel between them. Thus, sensor system 8 can communicate via wireless transmission (e.g., ANT+, low power Bluetooth, etc.) with display device 14, 16, 18, 20 (e.g., a hand-held computing device) at predetermined time intervals. In some embodiments, the duration of the predetermined time interval can be selected to be long enough so that the sensor system 8 does not consume too much power by transmitting data more frequently than needed, yet frequent enough to provide substantially real-time sensor information (e.g., measured glucose values) to the display device 14, 16, 18, 20 for output (e.g., display) to a user. The predetermined time interval may be every five minutes, for example. It will be appreciated that this schedule can be varied to be any desired time interval between data transfer activity. Those times when the communication channel is established and sensor data is being transmitted may be referred to as sensor packet transmission sessions.

In between these data transfer procedures, the transceiver 316 of the analyte sensor system 8 can be powered down or in a sleep mode to conserve battery life. To establish a communication channel, the analyte sensor system 8 may send one or more message beacons every five minutes. Each message beacon may be considered an invitation for a display device 14, 16, 18, 20 to establish a communication channel with the sensor system 8. During initial system set up, the display device 14, 16, 18, 20 may listen continuously until such a message beacon is received. When the beacon is successfully received, the display device 14, 16, 18, 20 can acknowledge the reception to establish communication between the devices. When the desired data communication is complete, the channel can be broken, and the transceiver 316 of the analyte sensing system 8 (and possibly the transceiver 338 of the display device 14, 16, 18, as well) can be powered down. After a five minute period, the transceivers 316, 338 can be powered up again substantially simultaneously, and establish a new communication channel using the same process to exchange any new data. This process may continue, with new communication channels being established at the pre-determined intervals. To allow for some loss of synchronization between the two devices in between transmissions, the analyte sensor system 8 may be configured to send a series of message beacons in a window of time around the scheduled transmission time (e.g., 8 message beacons per second for 4 seconds). Any one of the message beacons can be used to initiate the establishment of a new communication channel when it is received by the display device 14, 16, 18, 20.

Pattern Recognition

The process of detecting patterns based on raw sensor data according to some embodiments will be described with reference to FIG. 4. The term "pattern" as applied to glucose data measurements and used herein refers generally to repeated relationships between glucose data and some additional variable. The additional variable is often times an occurrence of an action or condition, but can be a non-occurrence of an action or condition, where an action can be eating or exercising for example, and a condition can be the value of a physiological parameter such as body temperature, or the like. A "pattern" in glucose data exists when similar glucose values tend to be associated with similar times, events, or conditions. In some embodiments described herein, patterns are detected and the user is made aware of their existence in a user friendly way that has not been heretofore available. A pattern may indicate a recurring event based on factors such as time of day, overcorrection of events by a user, and/or user activity, as will be discussed in greater detail below.

Figure 4:
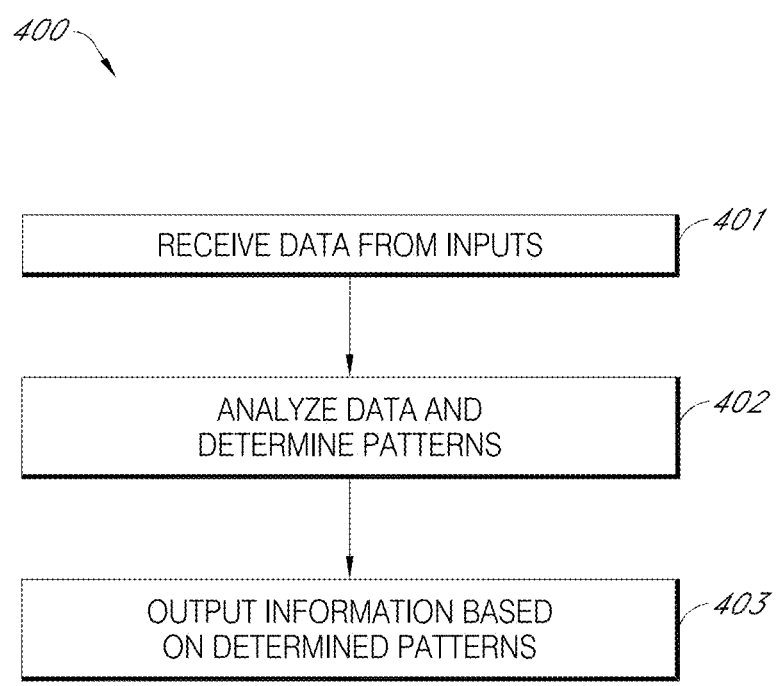
FIG. 4 illustrates a flowchart of a method of detecting patterns according to some embodiments.

FIG. 4 illustrates a flowchart of a method 400 of detecting patterns according to some embodiments. The method 400 includes receiving data from inputs as represented by block 401. The inputs provided may include, for example, data from a continuous glucose monitor (CGM data). The CGM data may be both real-time and historical data over a period of time. For example, the data may include historical data from a period covering a four week interval of monitored analyte detection levels. Additionally, or alternatively, the inputs can also include a variety of other inputs relevant to monitored analyte, such as food intake (e.g. time, amount of carbohydrates, other food related information), exercise, time of day, awake/sleep timer intervals, medications ingested, etc. Inputs may also be entered by a user or can be received from external devices (e.g., mobile phone, personal computer, dedicated CGM receiver, etc.) or derived from analysis of sensor data.

The method 400 may proceed by analyzing the input data for patterns as represented by block 402. For example, patterns can be recognized based on predefined criteria or a set of rules defined in a data analysis application. Additionally, the predefined criteria or rules may be variable and adjustable based on user input. For example, some types of patterns and criteria defining patterns can be selected, turned off and on, and/or modified by a user, a user's physician, a user's guardian, etc.

Some examples of the types of relationships that can be considered a pattern include hypoglycemic events by time of day. Generally, these patterns may be identified in situations where the user tends to have low glucose concentrations around the same time in the day. Another type of pattern which may be identified is a "rebound high" situation. For example, a rebound high may be defined as a situation where a user overcorrects a hypoglycemic event by overly increasing glucose intake, thereby going into a hyperglycemic event or near hyperglycemic event. These events may be detected based on a predefined set of criteria or rules, as will be discussed in greater detail below with reference to FIGS. 5A-5E, and identified as patterns.

Patterns that may be detected include, but are not limited to, a hyperglycemic pattern, hypoglycemic pattern, patterns associated with a time of day or week, a weighted scoring for different patterns based on frequency, sequence, and severity. Patterns may also be based on a custom sensitivity of a user, a transition from a hypoglycemic to hyperglycemic pattern, an amount of time spent in a severe event, and a combination of glucose change and time information. Detected patterns may also be patterns of high variability of glucose data. Further, a pattern may be based on a combination of previous pattern data and a currently detected situation, whereby the combined information generates a predictive alert.

The method 400 may proceed by outputting information based on the determined patterns as represented by block 403. For example, the output can include a real-time analysis of the inputs and determined patterns or may be a retrospective analysis of the data. The output may be provided by a device which is external to the sensor device, such as display device 14, 16, 18 or 20 discussed, for example, with respect to FIG. 1 above. The output may include a detailed report of the determined pattern information and possible corrective actions for the user. The output may also include alerts in the form of text message, audible alert, or the like.

Pattern Detection

As discussed above, pattern detection may be based on a number of factors. In the following discussion, pattern detection will be discussed with reference to detection of patterns based on time of day and rebound highs. However, one of ordinary skill in the art will recognize that pattern detection is not limited to these two types of patterns. Rather, these patterns serve as examples for the following description of some aspects of the disclosed embodiments.

For purposes of the following discussion, a "hypoglycemic episode" is a period of time with at least some relatively low glucose concentration measurements. A "hypoglycemic event" is a hypoglycemic episode that is determined to have clinical significance based on one or more characteristics of the episode such as duration or lowest measured values. A "hypoglycemic pattern" is a set of hypoglycemic events that have a relationship to one another, such as tending to be related in a time, action, or condition. For the purposes of pattern detection, several alternative definitions for a hypoglycemic event are possible. Prior to defining hypoglycemic events, it is relevant to examine the characteristics that are indicative of a hypoglycemic event which have clinical significance. Events of clinical significance include falling to a very low glucose level, even where the dip in glucose level occurs only for a short amount of time. Further, depending on the predefined threshold level, a glucose level which remains below the threshold level, even for a long period of time, may not be considered a clinically relevant event. For example, if such a pattern fails to repeat over a period of several days, it may indicate that the user has reasonable control of the glucose level, and no corrective action may be necessary. Additionally, a glucose level which remains substantially below a first threshold level, while not reaching what one would consider dangerous levels, for substantially long periods may indicate a need for corrective action.

The above described glucose pattern detection methods will be described in greater detail with reference to FIGS. 5A-5E below. FIGS. 5A-5E illustrate example graphs of glucose levels over a time period according to some embodiments. For example, the graphs of FIGS. 5A-5E plot estimated glucose values (EGV) over several hours. As used herein an estimated glucose value (EGV) means a glucose value estimated by a glucose monitoring system. The glucose monitoring systems described herein are typically continuous glucose monitoring systems, but the disclosed embodiment are not limited to just continuous glucose monitoring systems. Also, an estimated glucose value can be a raw data value, calibrated data value, filtered data value or the like. Returning to FIGS. 5A-5E, for the purposes of discussion, two threshold levels for evaluating the EGV values are assumed. These thresholds include a first threshold value TH1 and a second threshold TH2 which is lower than the first threshold TH1. For example, TH2 may be a low EGV value, such as about 55 and TH1 may correspond to a higher threshold such as an EVG value of about 80.

With reference to FIGS. 5A-5E, analysis of what may be considered a "hypoglycemic event" will be discussed. Based on this analysis, a definition of terms that that are helpful in specifying a clinically relevant hypoglycemic event may be developed.

For example, the definition of the start point and end point of an episode may be defined with reference to FIGS. 5A-5E. The start of an episode may be considered to occur when the EGV value falls below the first threshold TH1 for the first time. The end of an episode may be considered to occur when the EGV has been come back up to a normal level. However, the end of an episode may not necessarily correspond to the time at which the EGV value reaches a level above the first threshold value TH1. As will be discussed below, there can be a few choices for deciding when the episode has ended.

These choices include, for example, a time at which the EGV has been above TH1 for more than a certain period of time (e.g. about 45 minutes). This may be referred to as "sufficient time" end point determination. Additionally or alternatively, the end of an episode may be defined as the time at which the EGV reaches a certain high value. This can be defined as a point at which the EGV reaches a value of TH1+D1 for some predetermined offset value D1. This may be referred to as "sufficient value" end point determination.

Further, as another example, the end of an episode may be determined relative to a nadir value. As one example, a nadir value may be calculated by computing, at a target point, the average EGV using an interval (e.g. 30 minute window of data) around the target point. The calculation may be performed at every point of an EGV graph. The nadir can be defined as the first point in the episode where the average is the lowest. The end of an episode may be determined if the EGV rises by more than a predetermined value D2 from a calculated nadir value while also being above the first threshold value TH1. This may be referred to as "nadir offset" end point determination.

The latter two criteria, namely, the sufficient time end point determination and the nadir offset end point determination criteria, are based on the assumption that if the EGV rises sufficiently, then it is likely that the user took some action which resulted in the increase of EGV. Therefore, it may be concluded that any subsequent low is due to a different cause and corresponds to a different event.

Qualifying an Episode as an "Event"

The above definition of an episode is a general one and it is possible that not all such episodes are clinically significant. The following discussion focuses on detecting episodes that are clinically significant.

First, however, a definition of "average difference" in an episode is provided. The average difference may be defined as the average value of a period in an episode which identifies how far the EGV has been below the threshold value of TH1 on average during the episode. More precisely, the average difference (AD) may be defined by Equation 1 below:

$$AD = (\Sigma TH1 - EGV(P))/X \qquad \text{Eq. (1)}$$

where P corresponds to the subset of points that include all points during the episode that are below the first threshold value TH1, and X corresponds to the total number of points in the subset P.

The following description identifies those episodes that may be of clinical value, and may be identified as a hypoglycemic event. According to a first example, with reference to FIG. 5A, the EGV value falls below the first threshold TH1 but remains above the second threshold TH2. Since the EGV remains near the first threshold value TH1, the average difference AD is relatively small. A set of predetermined average difference thresholds $AD_{TH1}$ and $AD_{TH2}$ may be defined for determining whether a calculated average difference value for a given episode qualifies as a hypoglycemic even. The first average difference threshold $AD_{TH1}$ may be greater than $AD_{TH2}$. In addition, For example, $AD_{TH1}$ may be equal to a value of 15 and $AD_{TH2}$ may be equal to a value of 10. In addition, a first time interval $TP_1$ may be predefined for comparison with a time at which the EGV remains below the first threshold value TH1. For example, $TP_1$ may be set to a value of 10 hours, but is not limited thereto.

If the average difference AD of an episode is more than $AD_{TH2}$ (e.g. 10) and the total time that the EGV is below TH1 is more than the time period $TP_1$, then the episode may be considered a hypoglycemic event. Also, in one implementation, if the average difference AD is more than the first average difference threshold $AD_{TH1}$ (e.g. 15), then the episode may be considered a hypoglycemic event regardless of the total time the EGV is below TH1. That is, in the latter case, the total time that an EGV is below TH1 may be disregarded because the average difference AD is so large. However, in another implementation, a total time the EVG remains below the first threshold value TH1 may be a factor in determining whether or not an episode is considered a hypoglycemic event when the average difference AD is more than the first average difference $AD_{TH1}$. For example, an episode may be considered a hypoglycemic event if the average difference AD is more than the first average difference threshold $AD_{TH1}$ (e.g. 15) and the EVG remains below the first threshold value TH1 and/or second threshold value TH2 for more than a predetermined threshold amount of time $TP_2$, which may be less than $TP_1$.

Figure 5A:
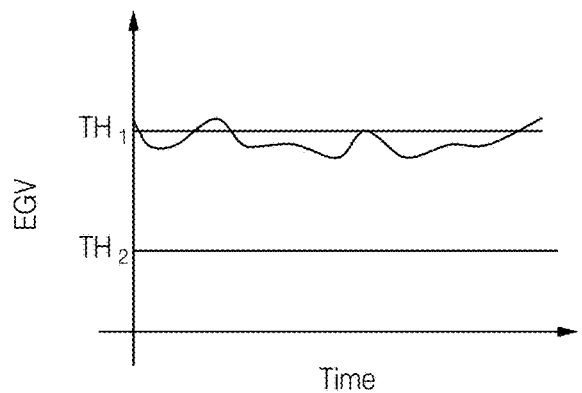
FIGS. 5A-5E illustrate example graphs of glucose levels over a time period according to some embodiments.

As a non-limiting example with reference to FIG. 5A, the average difference AD may correspond to a value of 5, while the period of time that the EGV value remains below the first threshold value TH1 may be equal to about 1 hour. In this example, even though the time period of FIG. 5A may be long, the episode of FIG. 5A is not classified as a hypoglycemic event since the average difference AD is low. That is, since the EGV remains near the first threshold TH1, from a clinical perspective, no corrective action may be necessary by the user.

Figure 5B:
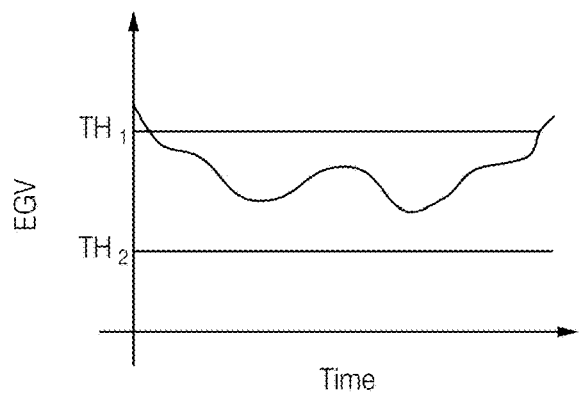

As a non-limiting example with reference to FIG. 5B, the average difference AD may correspond to a value of about 12, and the time period that the EGV is below TH1 may be equal to about 2 hours. As a result, in this example the episode of FIG. 5B may be classified as a hypoglycemic event since the average difference AD is greater than $AD_{TH2}$ and the time period is greater than $TP_1$.

Figure 5C:
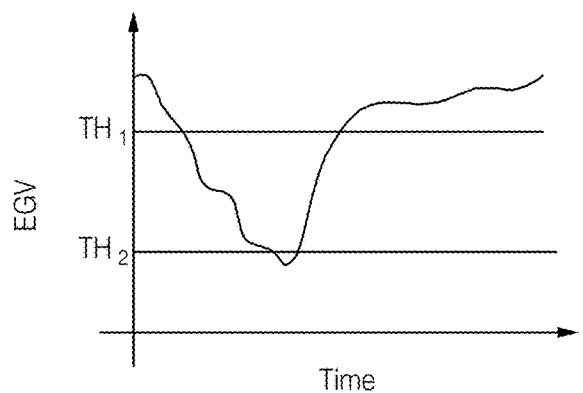

According to another non-limiting example, with reference to FIG. 5C, if the EGV falls below TH2 even for a very short period of time, then the episode may be classified as a hypoglycemic event. In this case the average difference may be disregarded.

Figure 5D:
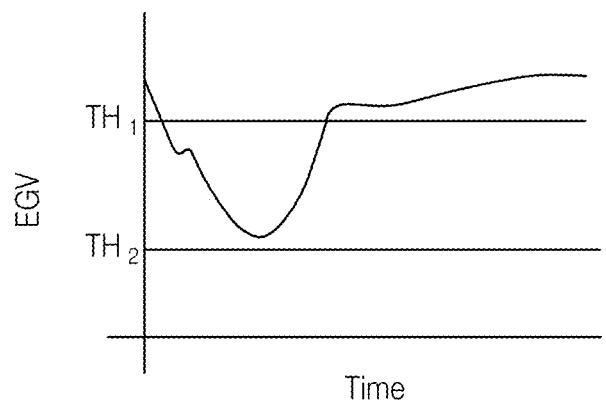

As a non-limiting example with reference to FIG. 5D, the average difference AD may be equal to a high value (e.g. about 20) and the time period that the EGV is below the first threshold TH1 may be relatively short (e.g. about 20 minutes). As a result, the episode may be classified as a hypoglycemic event since the average difference AD is greater than $AD_{TH1}$, even though the time that the EGV is below TH1 is less than $TP_1$.

Equation 1 above defines the average difference AD as a simple sum of differences TH1−EGV over a subset of points below TH1. According to some embodiments, the average difference may be amplified by using a power of individual differences rather than the simple difference calculation of Equation 1 above. Further, one of ordinary skill in the art will recognize that another function may be used to calculate the average difference AD. For example, a function which maps the difference to a weight value and bases the detection criterion on the average weight may be used.

In calculating the differences, the following choices may also be considered: first, an average over all the points of the episode, assuming a zero value for the difference at points where EGV is above $TP_1$; second, an average over only those points where the EGV was below $TP_1$.

Segment in an Episode

The concept of a segment in an episode may also be used in analyzing whether an episode may qualify as an event. Since an episode may have many points that are close to TH1 (or even above TH1), identifying parts of the episode that are significant may be desirable. A segment may be defined as a portion of an episode that corresponds to the most clinically significant data. For example, a segment may be defined as a set of consecutive points in an episode where the EGV is below TH1. Further, if within the set of such points, the difference (TH1−EGV) is less than (TH1−TH2)*0.1, then such points may be excluded from the segment.

When the average difference is computed, the average difference over each of the segments may be used and the maximum of the average difference values may be used to characterize an episode.

Figure 5E:
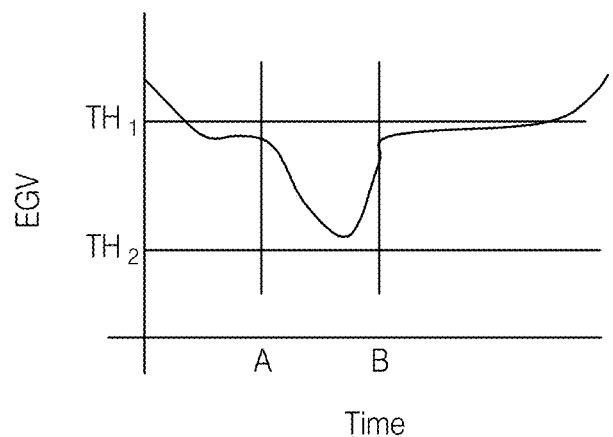

To illustrate the concept of a segment, an example will now be described with reference to FIG. 5E. Here, a segment is defined as the portion between time point A and the time point B as identified by the vertical lines in FIG. 5E. The segment bounded by lines A and B in this example corresponds to the portion of the episode where the difference (TH1−EGV) is less than (TH1−TH2)*0.1. As illustrated, the segment can be considered to include the most severe portion of the episode and disregard the data points where the EGV is close to the first threshold value TH1. As a result, the analysis of the episode may focus on the most clinically relevant data points. The episode may then qualify as an event if the segment portions of the episode qualify the episode as an event using, for example, any of the event qualifying conditions discussed above.

In the foregoing description, one of ordinary skill in the art will recognize that the number of threshold values is not limited to two threshold values as discussed above with respect to FIGS. 5A-5E. Rather, any number of threshold values TH may be defined for analyzing the data. Further, the number of average difference values AD and time periods TP may also include any number of predefined values. One of ordinary skill in the art will recognize that the above number of thresholds, number of time periods, and predetermined values for each threshold and time period are illustrative in nature and are used for ease of description of some aspects of the disclosure.

Further, any of the above described threshold values and time periods are variables that may be user configurable (e.g. by manufacturer, patients, health care providers, guardians, etc.). These include, for example, the first time period $TP_1$, first threshold value TH1, the second threshold value TH2, the first average difference value $AD_{TH1}$, and the second average difference value $AD_{TH2}$.

Distance Between Two Events

The distance, or the difference in time of modal day, between two events may also present clinically important data. There can be several definitions for the distance. For example, the distance may be defined as the distance between events H1 and H2 as the time span between the mid-points of events H1 and H2, or the time span between the closest points of H1 and H2. Using the latter definition, if the two events H1 and H2 are overlapping, then the distance may be defined as zero. If the events do not overlap, the distance may be defined as the time between the end of one event H1 and the beginning of the other event H2.

The distance may also be defined using the nadirs in H1 and H2. With the concept of a segment defined above, a particular time in an event may be at the midpoint of the deepest segment in the event. The distance between H1 and H2 may then be defined as the time span between the mid-points of the deepest segments in H1 and H2.

Repetitive Pattern Identification

Given a time interval TS, a pattern may be defined as a set S of events such that the distance between any two events in the set S is less than a time interval TS. Further, in some embodiments, no two events from the same day may be selected for inclusion in the set. In some embodiments, if H1 and H2 are two events such that the actual time difference between the two events H1 and H2 (not the modal day time difference) is less than 12 hours, then the events are not added to set of patterns S.

With these baselines, once TS and the number of events needed to recognize a pattern of events is specified, all the events may be scanned to identify repetitive patterns. This initial grouping may then provide a few candidate sets for patterns. These candidate sets may then be subsequently filtered for identifying patterns to output to the user.

For example, a set of events A, B, C, D, E, and F may occur on different days such that the events are each one hour apart on respective days. Further assuming TS is 2 hours and the number of events required for a pattern is three, the following sets of potential candidates may result: {A, B, C}, {B, C, D}, {C, D, E}, and {D, E, F}. From these initial sets, the sets which should be identified as patterns may be selected.

One or more of the following filters may be applied for selecting the final patterns or reducing the number of patterns prior to selecting final patterns from candidate sets:

1. Selecting the earliest set: Here, the sets may be sorted based on the earliest modal time of an event in each set. The earliest set is selected and all the events included the earliest set are deleted from the remaining candidate sets. The filter then iteratively proceeds in a likewise fashion with the next earliest remaining candidate set until every remaining candidate set has been selected. Note that a candidate set that no longer qualifies as a set under the predefined rules may be eliminated.
2. Prioritized by time of day: Using this filter, a certain priority can be assigned to the candidate sets based on the time of day. For example, the modal day can be divided into eight intervals of three hours each. Each interval is assigned a weight or score. Based on the assigned weight or score, the candidate sets may be prioritized by the weight or score of the events in the pattern, such as a sum, an average, a median or the like of the weights or scores in a candidate set. The highest priority set is then selected, and the events included in the selected set are deleted from the remaining sets. The next highest priority set may then be selected based on the assigned weights of the events remaining in its set, and all events in the currently selected set that are also present in other candidate sets are eliminated. The process may be iteratively performed until all candidate sets are processed in this fashion. Note that a candidate set that no longer qualifies as a set under the predefined rules may be eliminated.
3. Prioritized by type of events: Another filter may assign a weight or score to each event based on the severity of the event. For example, a deep event may be assigned a high weight or score. For example, an event based on the average difference may be assigned a weight that is proportional to the average difference. Additionally, or alternatively, the weight or score may also take into account the duration of the event. The candidate sets get prioritized by summing, averaging or taking the median value of the assigned weights or scores events in each set. These priorities may then be used to sort the candidate sets and eliminate candidate sets as discussed in filters 1 and 2, above.

In some embodiments, each of the above filters are iteratively applied (e.g., filter 1, then filter 2 and finally filter 3) until either a predetermined threshold amount or fewer number of pattern sets remain or each of the filters have been completely applied. If more than a predetermined threshold number of pattern sets remain after applying all of the filters, then a threshold number of pattern sets can be selected as a final set based on a priority, such as a priority by time or priority based on type of event.

Pattern Analysis by Event Detection

The previous sections define and outline exemplary methods for detecting patterns of events, with much of the description describing hypoglycemic events for illustrative purposes. This section further elaborates on an implementation on a computing device to detect patterns based on the above-described methods. The process will be explained with reference to FIG. 6.

Figure 6:
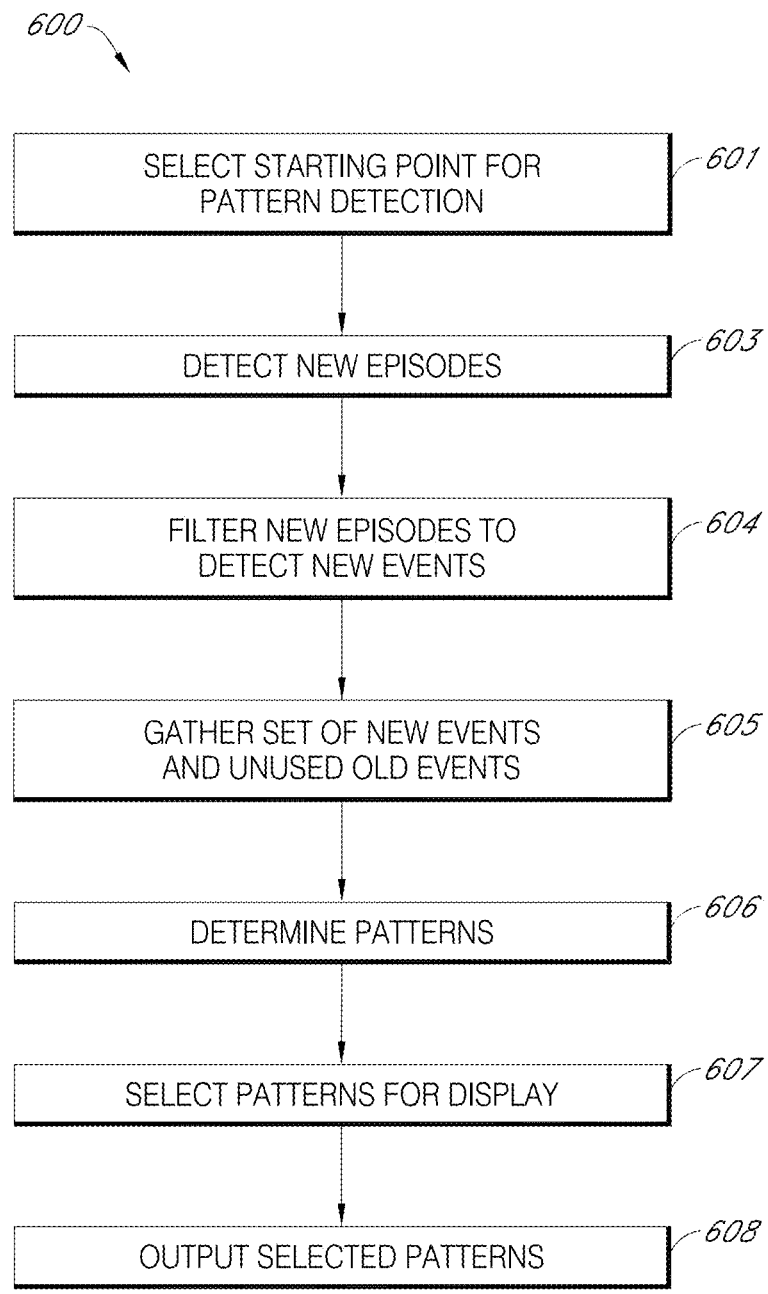
FIG. 6 illustrates a flowchart of a pattern detection method according to some embodiments.

FIG. 6 illustrates a flowchart of a pattern detection process 600 according to some embodiments. The various tasks performed in connection with process 600 may be performed by hardware, software, firmware, or any combination thereof incorporated into one or more of computing devices, such as one or more of sensor system 8 and display devices 14, 16, 18 and 20. It should be appreciated that process 600 may include any number of additional or alternative tasks. The tasks shown in FIG. 6 need not be performed in the illustrated order, and process 600 may be incorporated into a more comprehensive procedure or process having additional functionality not described in detail herein. For illustrative purposes, the following description of process 600 may refer to elements mentioned above in connection with FIGS. 1-5.

The pattern detection process 600 may be performed based on user request, or automatically. For automatic pattern detection, the process may be performed based on any number of predetermined or user defined variables. For example, according to some embodiments, the process 600 is performed automatically (without user interaction triggering the process) when one or more of the following conditions have been satisfied: (i) it has been at least one day since the process was last performed, (ii) no alerts are pending at this point, and (iii) the glucose monitoring system is currently between sensor packet transmission sessions (e.g., between sensor system 8 and display device 14, 16, 18 20). Additionally or alternatively, a restriction that the process 600 is only performed at a particular time of the day (e.g., at night time), or that that at least a certain number of days' worth of data (e.g., 7 days of data) is stored for analysis may be applied. Any of these restrictions may be user configurable (e.g., allow or disallow the restriction) depending upon user preference. In some embodiments, a user can configure the restrictions using user interface of display device 14, 16, 18, or 20 discussed above with reference to FIG. 1.

There may be additional optimizations provided while performing the pattern detection process 600 based on automatic triggering. For example, based on the performance of the process 600, the process may be performed in several installments over a period of time. Further, when the process is performed upon user request, a display to the user of status of the analysis or other information may occur while the data is being processed.

As illustrated in FIG. 6, the process 600 begins by selecting a starting point (or total timeframe) of data to be analyzed in block 601. The start point may correspond to the earliest point where EGV data exists or is available. For example, this time may be as old as one month from the time that the process begins, or even older, depending on the amount of stored data. The start time may also be set to optimize efficiency, and reduce the analysis of excessive data, by setting the start time to a time later than the earliest point where EVG data exists, such as one week, two weeks, three weeks, one month, two months, six months, one year or other time period, when EGV data to be analyzed is available.

If the process 600 has previously run, the start time may be set based on the oldest episode or event used in a prior iteration of the process. For example, if during the last iteration of the process, there are any episodes or events that were detected but not fully processed, the starting point of the oldest such episode or event may be used as the starting point. If there are no unprocessed episodes or events, the time that the process was run last may be set as the starting point.

The process proceeds to block 603, where new episodes are detected. Episodes may be detected as discussed above, such as with respect to FIGS. 5A-5E. As discussed above, new episodes may be detected by scanning the EGV records and using predefined criteria to detect the starting and ending of episodes. For example, an episode may be determined to have started when the EGV falls below TH1 and stays low for at least 15 minutes (e.g. three data points at five minute intervals). Because the first data point in the data being analyzed may be part of an episode under the definitions for an episode being used, the time of the available EVG data point may be considered as the start time of an episode. An episode may be considered to end when the EGV remains above TH1 for at least 45 minutes, or when the EGV reaches TH1+40 mg/dL.

At block 604, the detected episodes are filtered based on their characteristics to arrive at a set of events. As discussed above, only the events that are clinically relevant for identifying patterns are used for pattern detection. According to one example identifying hypoglycemic episodes, a value of average difference thresholds $AD_{TH1}$ and $AD_{TH2}$ may be set for comparison with an average difference AD of the episode. $AD_{TH2}$ may defined as (TH1−TH2)*0.33 and $AD_{TH1}$ may defined to be (TH1−TH2)*0.66. If, in an episode, the EGV reaches TH2 the episode is characterized as a hypoglycemic event. If, in an episode, there is at least one segment where the average difference is greater than $AD_{TH2}$ and the segment is longer than a predetermine time period (e.g. 40 minutes), then the episode may be characterized as hypoglycemic event. If in an episode, there is at least one segment where the average difference is greater than $AD_{TH1}$, then the episode may be characterized as a hypoglycemic event.

At block 605, all available events to be analyzed are identified and grouped. In one implementation, an event is determined to be available if it was not previously identified as part of a pattern, even if the event was previously identified as an event during a prior iteration of process 600. Thus, both "old" and new events may be considered.

In some implementations, once all available events are gathered, sets of events may be formed and patterns determined based on the sets of events at block 606. Events may be grouped to form one or more sets of events based any qualifying criteria discussed herein.

In one implementation, each set of events may be based on a distance between events. The distance based on segments may be used to define the distance between two events. For example, the distance may be the time span between the mid-points of the deepest segment in each event. The distances may then be used to determine the events that are close to each other. Since the expected number of hypoglycemic events is generally small, this determination may be performed by iteratively identifying all events that are within a predefined distance of each event.

For example, if an event A is between 11 PM and 6 AM, then any event that is within a 4 hour window of event A will be included in the set for event A as long as the event is within 11 PM and 6 AM. The window of time may be variable based on the time of the event to be analyzed. For example, for an event A occurring between 6 AM and 11 PM, only those events within predetermined window of time, such as 2 hours, of event A may be included in the pattern set around event A. A set that has more than a predetermined number of member events (e.g., 2, 3, 4 or more events in a set) may be considered a pattern.

In some implementations, process 600 can identify and delete duplicate pattern sets that may have been formed in the previous step. For instance, given sets {A, B, C} and {B, A, C}, then the latter set may be deleted.

Based on the remaining pattern sets, patterns are selected for display in step 607. It should be appreciated that there are a myriad of approaches that can be implemented to select patterns for display, outputting or further processing. One approach can be to simply select all patterns. Another approach is to select all patterns if the total number of patterns is less than a predetermined threshold number, and filter the patterns using one of the filters discussed herein, for example, until less than the predetermined threshold number remain. A further approach is to select only patterns that satisfy certain predetermined conditions, such as patterns falling within a particular time of day, patterns that follow a particular occurrence (e.g., a meal, exercise or medication administration) or strength of a pattern based on a strength metric (e.g., using a weighting or scoring of events in a pattern).

In some implementations, the patterns which are selected may be based on particular preferences indicated by user. In this way, a user can define how many patterns the user wants to view, the strength or weakness of patterns to view, patterns occurring at particular times of day or after particular occurrences, and the like.

To illustrate, in one implementation, priorities for the remaining sets are determined and pattern sets filtered based on the priorities. The priorities may be assigned according to the time of the events, severity of the events or some other clinical relevance criterion, as discussed elsewhere herein. For example, a hypoglycemic event between 11 PM and 6 AM may be given a priority of 2. A hypoglycemic event that crosses TH2 or with average difference greater than $AD_{TH1}$ may be given an additional priority of 1. Further, an event that occurred within a predetermined amount of time, such as within the past day, may be given an additional priority of 1. The priority of an entire pattern set may be defined as the sum of the priorities of all the evens within the pattern set.

A predetermined number of the highest priority pattern sets for display to the user may be selected. If there are more than one pattern sets that have the same priority, then the pattern set having the earliest event may be selected. Alternatively, the set having the most recent event may be selected. In accordance with some embodiments, once an event is selected for a pattern set that is shown to the user, it is taken out of the pool of events that can be used for later pattern detection in a subsequent iteration of process 600. That is, the event is no longer available for selection in step 605 in a subsequent iteration of process 600.

At block 608, the selected patterns are outputted for display or further processing. For example, the patterns may be displayed on a user interface, such as one of the user interfaces described in FIGS. 9-11. In some implementations, alerts can be triggered based on the selected patterns instead of or in addition to displaying the selected patterns. And is some implementations, the selected patterns are processed further to modify some other process, such as a medication administration routine (e.g., insulin administration routine) and the like. Further, the selected patterns may be logged or stored in memory of the system for subsequent access or display to a user.

In accordance with some embodiments, after events are identified as discussed above in step 604, patterns may be detected at step 606 by sorting the identified events in increasing order of a time of day (hour, minute, second of the time of day) associated with the event. The time of day can be any way of associating a time of day with an event discussed herein, including start time of the event, end time of the event, mid-point time of the event, time corresponding to a nadir point of the event, and the like. Once sorted by time of day, the events may be scanned in order of the first event to the last event. At each event, all other events that are within a predetermined amount of time (e.g., 2 hours) may be added together to form an event group that defines a pattern. In this way, a plurality of patterns may be identified from a corresponding plurality of event groups. Information related to all or some of the patterns can then be outputted to a user or another computing device for further processing. In one embodiment, information associated with each pattern is displayed on a user interface. The information can include the times associated with one or more members of the event group forming the pattern, number of members in each group, an indication of clinical relevance of one or more of the patterns, glucose value associated with each member of an event group, an average or mean glucose value of the members in an event group, and the like. Further, in some embodiments, the patterns can be analyzed using clinical relevance criteria and outputted by ranking the patterns from most clinically relevant to least clinically relevant.

Exemplary Pattern Reporting User Interface

Figure 10:
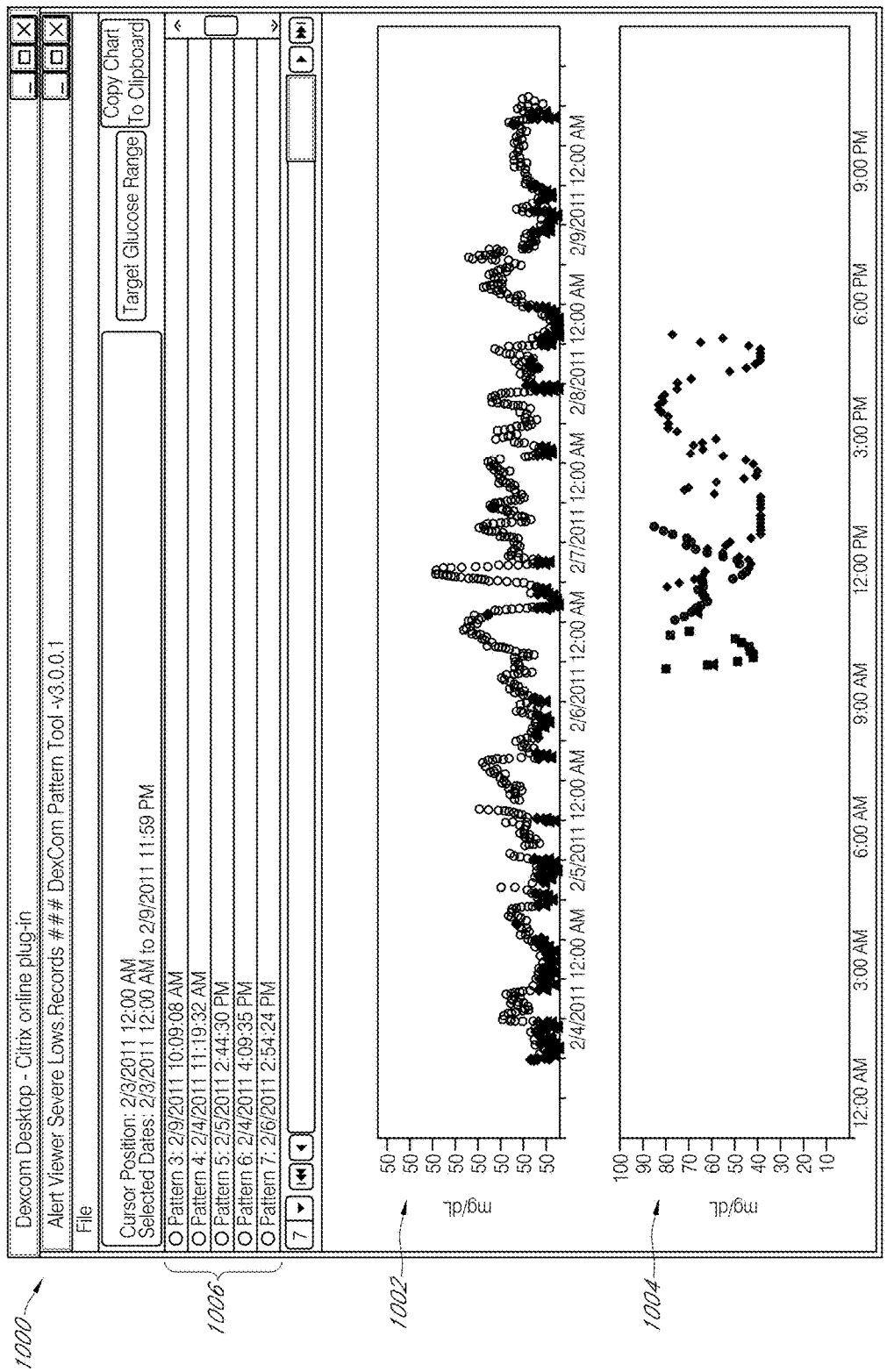
FIG. 10 illustrates an example of a user interface for displaying pattern results according to some embodiments.

A user interface 1000 displaying a report that includes a chart 1002 of glucose data points over a six day period and a chart 1004 of individual events that were determined to form a pattern is illustrated in FIG. 10. In the chart 1004, the data points of each event in a pattern are indicated by the same symbol so that the behavior of each event in a group can be visualized. Further, the user interface 1000 provides a menu 1006 listing a plurality of patterns identified in the glucose data being analyzed. The patterns in the list can correspond to patterns selected using process 600, discussed above, for example. Each pattern can be selected by a user using, for example, a pointing device of user interface 1000. The selected pattern may then be displayed in chart 1004. This way, a user can view the glucose data points associated with each event that forms the selected pattern.

In some embodiments, the threshold values and time periods discussed herein are initially set by a manufacturer, but can be modified by a user using, for example, one of the display devices 14, 16, 18 or 20 discussed above with respect to FIG. 1.

Pattern Analysis by Aggregating EGV by Time of Day

According to some embodiments, another approach for detecting patterns in glucose data (e.g., EGVs) over a period of time is to aggregate the glucose values by time of the day. According to some embodiments, the method may include dividing the 24 hours in the day into epochs, each epoch spanning a predetermined interval of time, such as a 1, 5, 10, 15 or 20 minute interval. The EGVs for a given epoch from all days over a predetermined range are aggregated to derive a value for the particular epoch. If the aggregated value for the epoch shows that the EGV for that epoch exceeds a predetermined threshold (e.g., falls below a predetermined value), the epoch may be flagged as a match for pattern analysis purposes.

An epoch may be chosen to have a duration equal to the periodicity of the sampled data or as small or as large as the granularity desired for detection/reporting of pattern occurrences. If the sampled values have a periodicity much smaller than the epoch duration chosen, then the sampled data can be averaged over the epoch duration as a single value or, alternatively, the mean value of the sampled data over the epoch duration can be used as the value of the epoch.

Multiple contiguous epochs may be chosen to represent the desired duration/span to detect patterns. According to some embodiments, all the epochs that span an entire day may be chosen and then, if desired, a filter may be applied on the timestamps of the sampled values to limit which epochs are used in occurrence pattern detection analysis.

Epochs may also associate (or contain) the sample values that match the pattern and that match the epochs time period.

According to some aspects, the aggregate method may be used to detect patterns of low or high glucose occurring around the same time of day. Further, patterns of rapidly falling or rising changes in glucose around the same time of day may be detected.

In some implementations, epochs can be scored to facilitate detection of particular patterns. As mentioned above, a 24 hour period of a modal day may be divided into equal intervals (e.g. 5 minutes intervals). Each such interval is defined as an epoch. For an analysis of EGV data over N days, for every epoch T, a function Score (T) is defined as follows:

$$\text{Score } (T) = \left( \sum_{0-N} TH1 - EGV(T) \right) \quad \text{Eq. (2)}$$

where TH1 corresponds to a predetermined threshold. In some embodiments, the value of TH1 can be defined so values that fall above the predetermined threshold are given a score of zero. In this manner, all EGVs that are above the TH1 threshold are given the same weight (i.e. 0), thereby emphasizing EGVs that fall below the threshold TH1. Scores for each epoch interval are computed. For example, for a 5 minute interval, scores for all the 288 epochs are calculated over N days. Assuming a TH1 of 70 and N=7, for example, and the epoch to be analyzed is for a time period between 10:15 AM and 10:20 AM the following values for EGV may be detected: EGV (Day 1)=65, EGV (Day 2)=72, EGV (Day 3)=68, EGV (Day 4)=69, EGV (Day 5)=71, EGV (Day 6)=64, and EGV (Day 7)=66. The epoch score for this time interval is then calculated as:

Score (T)=5+0+2+1+0+6+4=18

In the above example, a summation of the simple differences between the threshold TH1 and EGVs are used in defining the score above. However, a function of the EGV may be used instead. For example, each EGV can be assigned a weight, and the sum or mean of the weights may then be used to calculate the score of the epoch.

Epochs may be flagged as a match based on their scores. For example, given a predetermined threshold score D, an epoch T may be flagged as a matching epoch if Score (T)>D. As discussed above, the simple difference value of Equation 2 above is not the exclusive way for defining a score. Accordingly, a match may also be based on other methods depending upon how a score is defined.

In some embodiments, a criterion that can be used for identifying matches is the number of days that contribute to the score at a given epoch. For example, while performing a seven day data analysis, if an epoch includes two days for which the EGV was very low then it may be considered a match. However, if an epoch had an EGV that was closer to TH1, then it will be considered a match only if a majority of days (e.g. 5 days) contributed to that epoch.

Patterns may be identified by scanning all the epochs for a modal day starting at, for example, the beginning of a day (e.g., at time 00:00). At any point of time, the scanner can be in one of two states: "In event" or "Out of event". The scan may start in an "Out of event" state and as soon as the first epoch is encountered that is flagged as a match, the scan may then enter the "In event" state. In some implementations, the scan then transitions to an "Out of event" state only after the scan counts a predetermined number of epochs (e.g. nine epochs) that are not a match, or if a predetermined number of continuous epochs (e.g., 3) are not a match). Should epochs that fall on the end of a group of "In event" epochs not be a match, the "in event" state can be moved back to the last flagged epoch. Once all the epochs are scanned, any group of consecutive epochs that are "In event" may form one pattern.

It is appreciated that there may be patterns that start very late in one day and cross over to the beginning of the next day. To account for such patterns, the same data may be juxtaposed twice when the scanning is performed on the data to account for patterns spanning over more than one day.

Pattern Calculator Using Data Aggregation

In some embodiments, a pattern calculator, or pattern detector, may be used to aggregate data in a set of epochs to detect patterns in the data that match a pattern definition. The glucose data can be weighted according to a weighted assignment map or function, or can be the actual glucose concentration value of the data point. The pattern calculator result can be a set of patterns detected. Each pattern can be a sequence of one or more epochs that contain contributing values that meet pattern bound criteria and pattern threshold criteria.

Figure 7:
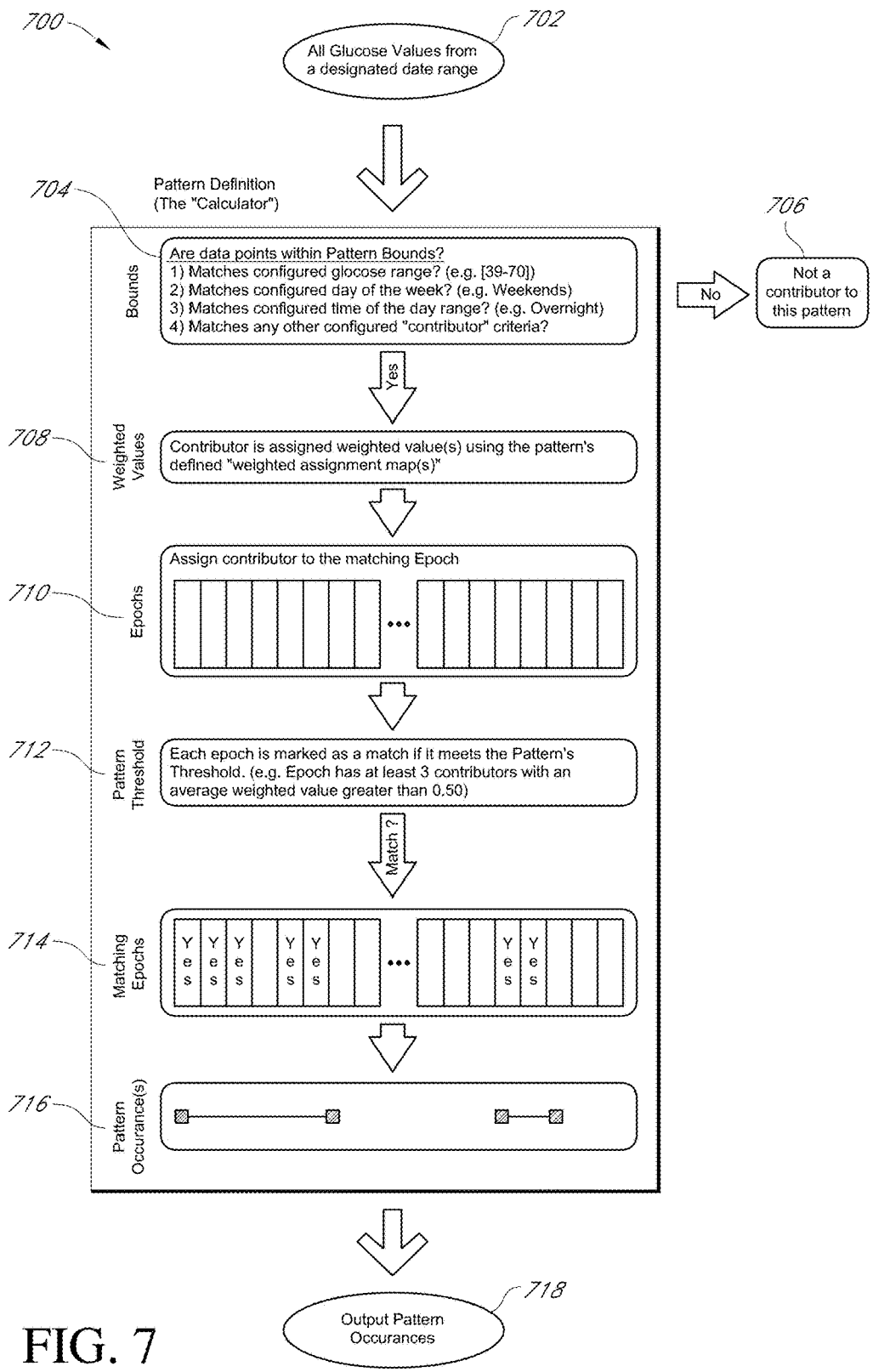
FIG. 7 illustrates a flowchart of a pattern detection method according to some embodiments.

FIG. 7 illustrates a process 700 for pattern detection using weighted epochs in accordance with some embodiments. The following algorithm may also be used to detect a pattern in a host's glucose concentration over time. The various tasks performed in connection with process 700 may be performed by hardware, software, firmware, or any combination thereof incorporated into one or more of computing devices, such as one or more of sensor system 8 and display devices 14, 16, 18 and 20. It should be appreciated that process 700 may include any number of additional or alternative tasks. The tasks shown in FIG. 7 need not be performed in the illustrated order, and process 700 may be incorporated into a more comprehensive procedure or process having additional functionality not described in detail herein. For illustrative purposes, the following description of process 700 may refer to elements mentioned above in connection with FIGS. 1-6.

At step 702, process 700 obtains glucose data for a designated date range. In some embodiments, the glucose data includes sampled data generated by sensor 10 that has been processed (e.g., filtered, averaged, and the like) and calibrated. In addition to glucose concentration values (e.g., EGV), the glucose data can include information associated with the glucose data, such as the time when a glucose concentration value was present in a subject. This time may be a measurement time, although there may be a time lag between a measurement time and the associated time that a given concentration is present in a target area of the subject. For example, there may be a time lag between a measurement of a subcutaneous glucose concentration of a subject and a blood glucose concentration (target area) of the subject.

The glucose sensor data can be stored in computer memory of a system implementing process 700. The designated date range can be all glucose data available to the system (e.g., stored in memory of the system) implementing process 700 or a portion of the available data. For example, the glucose data can be all glucose data stored in the system spanning the past week, month, several months or year.

At step 704, process 700 applies bounds or filters to the glucose data to determine which data points may be considered contributors to the pattern detection. The bounds or filters may be defined by any number of criteria used to determine if a data point is a contributor to a pattern. For example, a data point can be determined to be a contributor using one or more of the following criteria: (i) a value range criteria defined by upper and/or lower bounds (e.g. below a value of 70 or within a range of 70 to 39), wherein a data point's value can satisfy the value range criteria if the data point's value falls within the upper and/or lower bounds, for example; (ii) a time range criteria defined by starting and/or ending times in a day (e.g. 4 AM to 10 AM), wherein a data point's value does not satisfy this criteria if the data point correlates to a time (e.g., was measured at a time or is determined to indicate a user's glucose concentration at a time) that falls outside of the time range criteria; (iii) a day of the week criteria defined by a subset of days of the week to be analyzed (e.g. Monday through Friday or Saturday and Sunday), wherein a data point does not satisfy this criteria if the data point is correlates to a day of the week that falls outside of the day of the week criteria. Any other criteria can be applied in combination with or separately from any of the examples provided above. For example, the filter may analyze only data points that correlate to a time that falls within a time frame (e.g., 3 hours) of the occurrence of a particular event when information is available indicating when the event has occurred. An occurrence of event can be a time when a user exercised, consumed a meal, administered insulin or other medication, slept or the like.

In some embodiments, a data point is considered to be a contributor only if the data point satisfies all of the criteria applied in step 704. In other embodiments, a data point need not satisfy all criteria to be considered a contributor. For example, a data point can be considered a contributor if it satisfies criteria associated with the occurrence of one event (e.g., consumption of a meal), but does not satisfy criteria associated with the occurrence of a different event (e.g., exercise).

Data points not considered to be contributors are discarded from process 700 at step 706.

Data points considered to be contributors in step 704 are then assigned weighted values in step 708. In some embodiments, each glucose value of the contributor data points has a corresponding weighted value as defined by a weighted assignment function or map. Accordingly, each contributor can be assigned a weighted value as defined by a weighted assignment function or map (also referred to herein as "mapping a weighted value to a contributor data point"). In some embodiments, the weighted assignment function or map can be embodied electronically in a lookup table.

Exemplary weighted assignment maps are illustrated in FIGS. 8A-8D. In FIGS. 8A-8D, the x-axis is a range of glucose values and the y-axis are corresponding assigned weighted values. The range of glucose values along the x-axis need only encompass the range of glucose values of value criteria applied in step 704, should a value criteria be applied in the bounds step 704, because values outside of the value criteria range should not be considered contributors and hence not be considered in the weighted assignment step 708 of process 700. In some implementations, the weighted values are scaled from 0 to about 1, where a higher weight is given to values considered to be more clinically relevant. However, it is appreciated that there are a myriad of different ways to assign weighted values.

While FIGS. 8A-8D illustrate weighted maps in column chart format, it is understood that the weighted maps can be in other formats, such as a line chart format. Regardless of the format of a weighted assignment map, a data point determined to be a contributor in step 704 can be assigned the weighted value associated with the glucose concentration value as defined in the weighted assignment map. It should also be appreciated that a mathematical function can be used to describe a desired weights to corresponding values, and such a mathematical function can be used instead of a map.

Figure 8A:
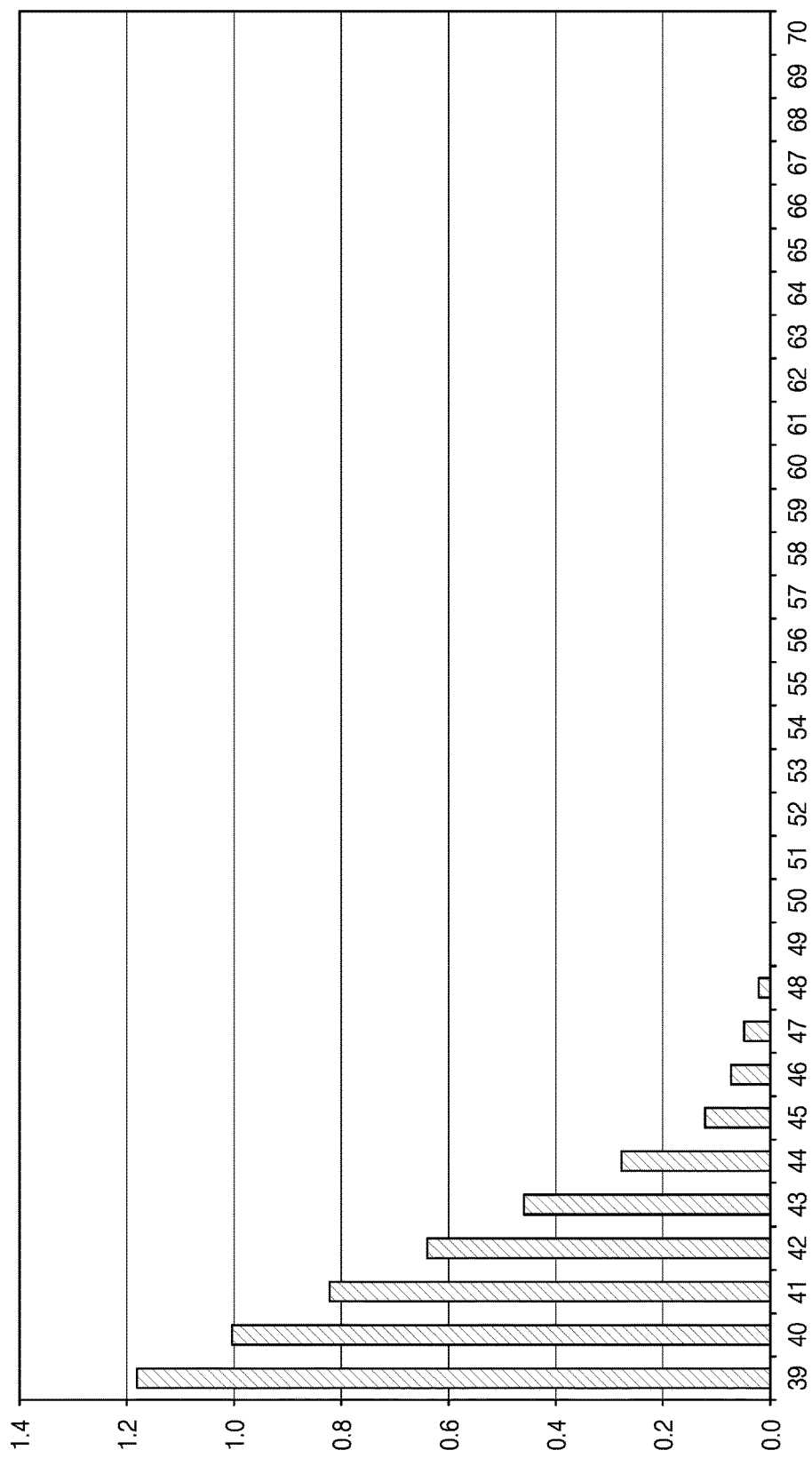
FIGS. 8A-8D illustrate plots of weighted assignment maps according to some embodiments.

FIG. 8A illustrates a weighted assignment map which is designed to be sensitive to severe hypoglycemic events. As illustrated, the map exhibits an exponential chart of the weighted glucose values, where lower glucose values are assigned exponentially higher weighted values than the higher glucose values. Indeed, values 50 and above in the map of FIG. 8A are assigned a weighted value of 0.

Figure 8B:
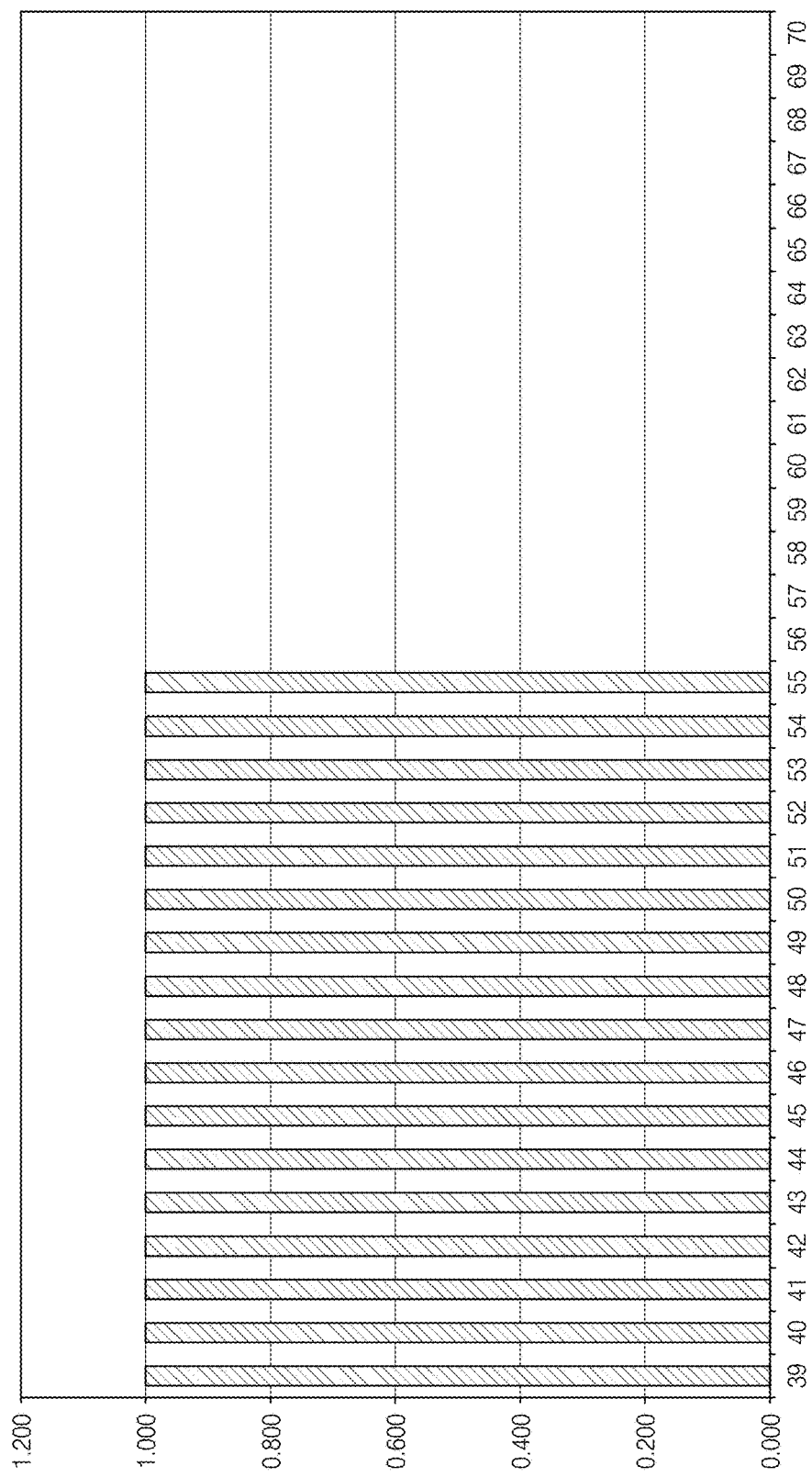

FIG. 8B is an exemplary weighted map according to an all or nothing approach. In FIG. 7B, all values that are below a glucose value of 55 are given a weight of 1, while any glucose values above a value of 55 are given a 0 or weight.

Figure 8C:
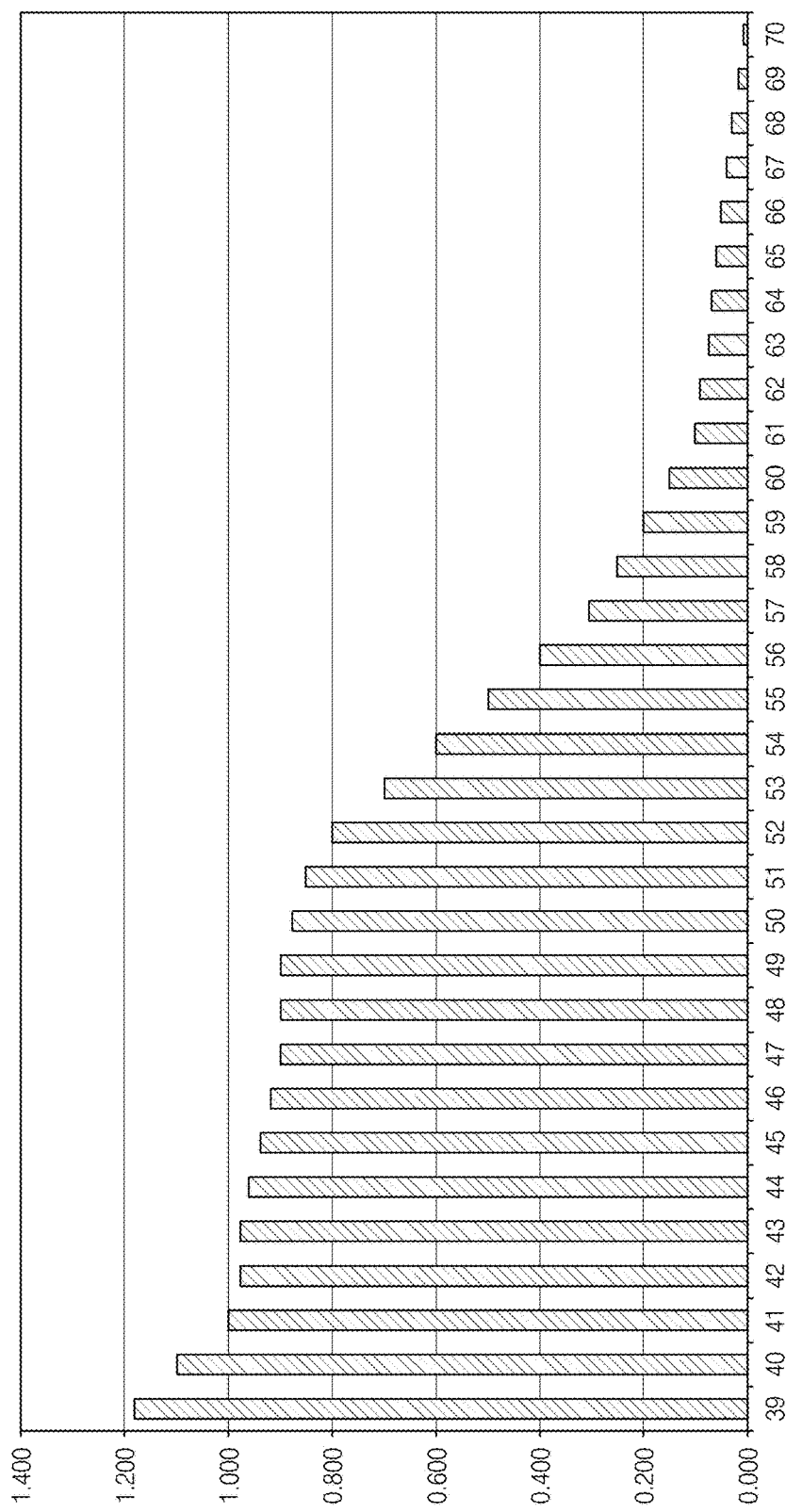

FIG. 8C is a weighted assignment map designed to have a non-liner polynomial approximation of clinical importance. The polynomial function may be predefined to identify glucose data of clinical importance. In the example of FIG. 8C, data points having values in the range of about 60 to 70 are assigned low weighted values to indicate that those values have relatively low clinical importance—albeit still some clinical importance. Data points are assigned increasingly higher weighted values along the range of about 60 to 50 to indicate that glucose concentration changes in this range are clinically important. That is, for example, a glucose value of 60 is notably, clinically different than a glucose value of 50. Further, data points having a value from about 50 to 39 are assigned large weighted values, although the values change relatively little across this range. This reflects a presumption that while these data values are determined to be of high clinical importance, the clinical relevance across this range is relatively the same.

Figure 8D:
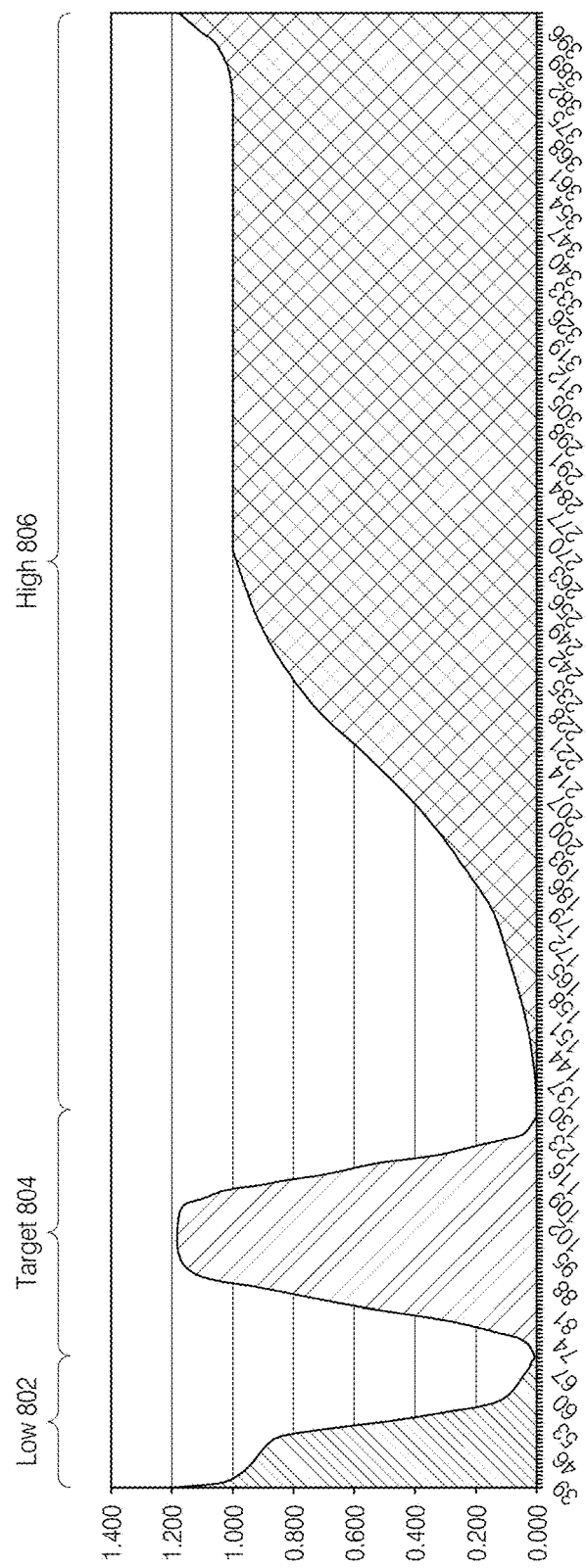

FIG. 8D illustrates a combination of three exemplary weighted assignment maps: a Low 802, Target 804, and High 806 map. The combined map 8D has an x-axis that ranges from 39 to 401 to illustrate that some embodiments can recognize patterns across a wide spectrum of glucose data, not just in low glucose ranges. Although maps 802, 804 and 806 could be used together in process 700, it should be understood that the exemplary process 700 would not be able to distinguish between data points that contribute to the respective low, target and high patterns. Instead, it is intended that process 700 be repeated using each map 802, 804 and 806 separately so that separate low, target and high patterns can be identified.

Further to FIG. 7, process 700 continues with assigning each contributor to a corresponding epoch in step 710. As discussed above, an epoch spans a predetermined amount of time of a day, such as a 5, 10, 20 or 30 minute interval of time. While the interval of each epoch can correspond to the sample interval of the glucose data being applied in process 700, it is appreciated that the epoch interval need not be limited by the sample interval.

As an illustrative, a non-limiting example of process 700, a contributor data point that is representative of a host's glucose concentration at 10:27 a.m. (as indicated by its timestamp, for example) would be assigned to an epoch that spans that time, such as an epoch spanning from 10:25 a.m. to 10:30 a.m. in the example of epochs spanning 5 minute intervals. In addition, all other contributor data points representative of a host's glucose concentration measured between 10:25 a.m. to 10:30 a.m. are assigned to that same epoch.

Thus, step 710 can be said to effectively group contributors according to times of the day being analyzed.

Next, in step 712, pattern thresholds can be applied to the epochs. Pattern thresholds can include one or more of the following: a threshold minimum number of contributors in an epoch, a threshold average weighted value of the contributors in the epoch, a threshold medium weighted value of the contributors in the epoch, a threshold sum of the weighted values of the contributors in the epoch, a threshold average difference of the weighted values of the contributors in the epoch, a threshold standard deviation value of the weighted values of the contributors in the epoch, and a threshold correlation value. The pattern thresholds can also be defined in terms of percentages, such that the pattern thresholds are defined based on the bounds applied in step 704. For example, should the bounds applied in step 704 of process 700 include criteria of data points spanning one week, a pattern threshold of 55% of the time can correspond to a minimum threshold of 4 contributors.

In step 714, process 700 matches epochs based on the pattern thresholds applied at step 712. In some embodiments, an epoch is determined to be a match only if all of the pattern thresholds are satisfied. In other embodiments, all pattern thresholds need not be satisfied for an epoch to be considered a match; for example only one or some number less than all of a plurality of pattern thresholds need be satisfied.

As an illustrative example of step 714, pattern thresholds can be defined as a minimum of three contributors in an epoch with the average value of the contributors in the epoch exceeding 0.50. In such an example, an epoch would be determined to be a match if it has three or more contributors and the average weighted value of the contributors in that epoch exceeds 0.50.

Process 700 can then identify pattern occurrences in step 716. A variety of ways can be used to identify a pattern. In some implementations, each matching epoch can be considered a pattern. In some implementations, a pattern is identified when there is a predetermined minimum number of contiguous matching epochs; for example, two or more contiguous matching epochs. In some implementations, a pattern does not need to have a strictly contiguous set of epochs. Instead, a predetermined number of non-matching epochs or a ratio of matching to non-matching epochs may be allowed within a pattern or before pattern is determined to end. In some implementations, a first threshold number (e.g., two, three, or more) contiguous epochs starts a pattern and the pattern is determined to end only after a second threshold number (which can be the same of different from the first threshold number) contiguous non-matching epochs are identified. Some implementations apply a combination of any of the above criteria for determining a pattern.

Step 718 outputs information associated with the identified pattern(s). For example, start and end times of an identified pattern may be reported to a user as the assigned starting and ending times of the first and last epoch in the pattern sequence. Attributes or properties of a pattern can also be outputted. The attributes or properties can be defined by any calculation or statistic related to the contributors in the occurrence. These calculations may be performed on the sampled values and/or weighted values of the contributors and then be used to compare or describe the resulting patterns.

Further, information associated with the patterns can be outputted to a user interface of a computing device, such as one or more of devices 14, 16, 18 and 20 of FIG. 1, in the form of alerts or reports. Information associated with the identified patterns can also be outputted to a medication administration device that can use the pattern information to form or modify a medication administration routine. For example, pattern information can be sent to an insulin pump controller that forms or modifies an insulin administration routine based on the pattern information, which can include administering more or less insulin during certain times of the day.

While the above described example of process 700 assigns weighted values to contributor data points at step 708, in some embodiments, contributor data points are not weighted, but rather retain their glucose value. Pattern thresholds at step 712 can then be defined based on glucose values rather than weighted values.

Based on the above described aggregation process 700, a significant reduction in complexity can be achieved by allowing each value to have a weighted contribution before being excluded from analysis and thus allowing multiple contributors to have a significant aggregate value where any single value may not have been previously considered significant on its own. Consideration of which values are near in time to each other may also be delayed until after all values have contributed. The resulting weighted aggregation can be more easily interpreted when displayed to a user and can be more easily scanned for occurrences above a desired threshold for a pattern match.

Furthermore, based on the above methods, the strength of a glucose value's contribution to a pattern may be reduced to a simple weighted numeric assignment. The weighted assignment map can be tuned specifically to match clinical relevance as determined by trained professionals or desired by a user, and where the map can support a complex non-linear curve that more closely matches clinical relevance and/or user specific factors and preferences. Different weighted assignment maps can be chosen for different glucose ranges to match each range's unique and different clinical needs. Weighted assignment maps can be scaled or amplified to increase or decrease their sensitivity to detecting a particular pattern.

According to some embodiments, the aggregate contribution of glucose values within an epoch of time is easily displayed and can be easily compared or ranked with other epochs. This concept of condensed volume of information can be more understandably presented to users.

Further, the above methods may eliminate the need to define or detect individual episodes within a single day when the goal is only to detect coincidental patterns of glucose over time (e.g. multiple days). However, the techniques described above can also be used to detect individual episodes, e.g. a single day pattern of glucose values. Some potential advantages can be realized when using the weighted values to determine inclusion in the episode and using the accumulated values as a volume when determining an episode's rank or importance.

Example User Interface for Reporting and Displaying Patterns

In some embodiments, a user interface of secondary display device 14, 16, 18, 20 may be used to configure and modify settings of process 700 and output results of process 700. For instance, not only can a user view results of the patterns detected using process 700 in a convenient fashion, but the user can use the user interface to select or modify bound criteria, select of modify weighted assignment map(s) and select or modify pattern thresholds.

Figure 9:
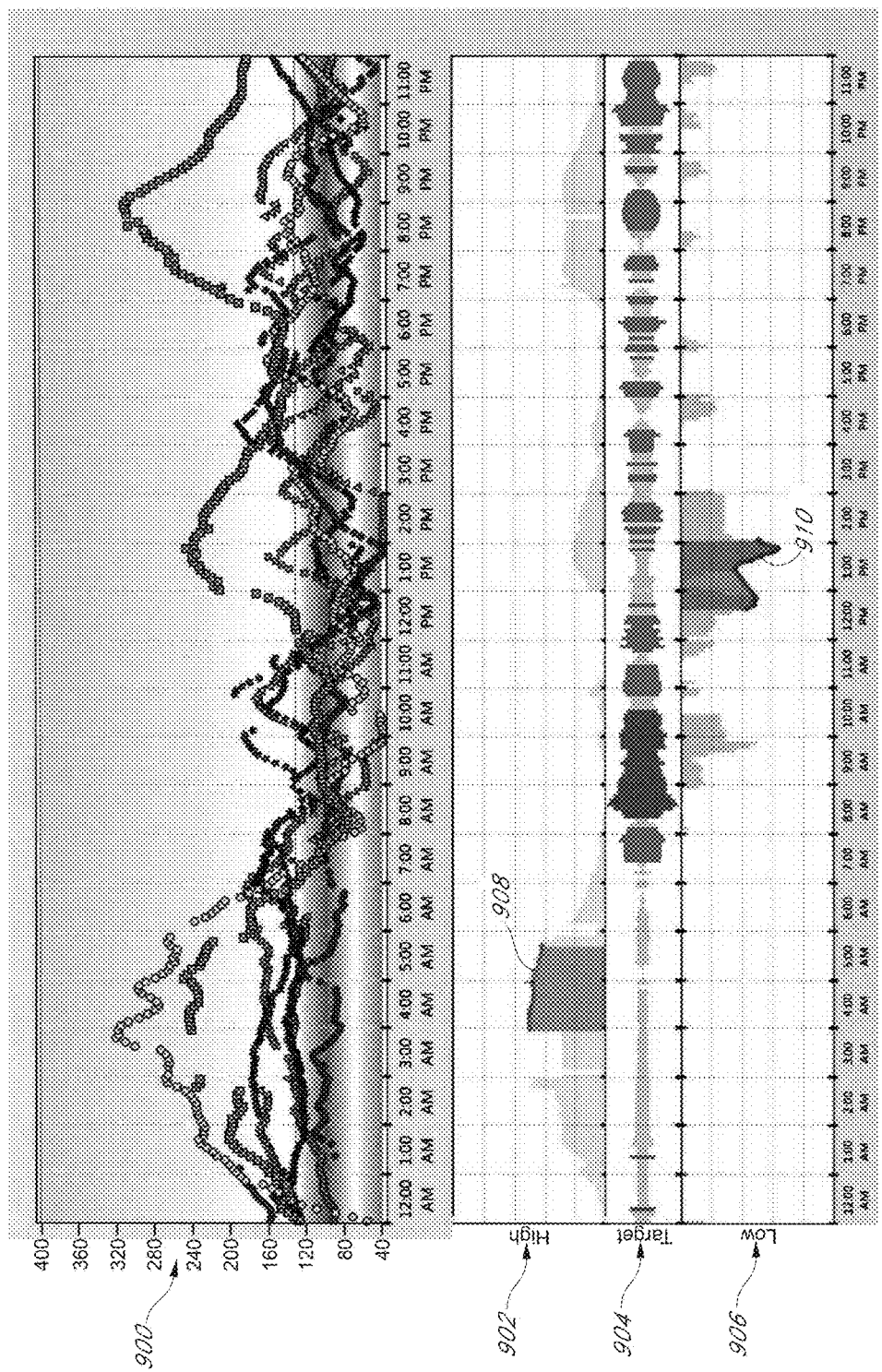
FIG. 9 illustrates another example of a weighted mapping of glucose values according to some embodiments.

FIG. 9 illustrates an example of a modal day chart 900 and different weighted aggregation charts 902, 904 and 906 that can be displayed on a user interface according to some embodiments.

The modal day chart 900 and weighted aggregation charts 902, 904 and 906 each superimpose a plurality of days (seven days shown in FIG. 9) of glucose value measurements onto a single modal day 24 hour period with the same times of day aligned for each of the days of the charts. The modal day chart 900 illustrates traces of seven different days of glucose monitoring measurements, each data point in a trace indicative of a host's glucose concentration at that time. Charts 902, 904 and 906 illustrate aggregated data and patterns based on the three different weighted assignment maps of FIG. 8D. Chart 902 is associated with the High assignment map 806, chart 904 is associated with the Target assignment map 804 and chart 906 is associated with the Low assignment map 802.

In some embodiments, each epoch may be plotted in a bar graph format, where the length of each bar represents the weighted sum of the contributors (aggregation) at a given time. In some implementations, other statistical algorithms can be applied to the contributors instead of a summation, such as averaging, applying a mean, determining a variation, and the like, with the result of the statistical analysis being displayed in chart 902, 904 or 906.

Charts 902, 904 and 906 of FIG. 9 illustrate the aggregated weighted contributors in bar graph form. The length of the bar graphs can indicate a relative strength of the contributors at the respective times of day. For example, chart 902 illustrates that a user's glucose concentration tends to be relatively high around 2:40 to 3:00 a.m., chart 904 illustrates that a user's blood glucose concentration tends to fall within a target range from about 7:30 a.m. to 10:40 a.m., although the glucose concentration can be relatively low from 9:00 a.m. to 10:20 a.m. as illustrated in chart 906. Further, a user's blood glucose concentration tends to be relatively low from about 12:00 p.m. to 3:00 p.m.

Charts 902 and 906 also highlight detected patterns 908 and 910. The patterns may be detected using process 700, for example. The patterns 908 and 910 are illustrated as darker sections of the bar graphs, with lines outlining a border of the bars falling within the pattern. In this manner, the user interface of FIG. 9 highlights the detected patterns in the charts 902, 904 and 906.

In some implementations, the bars in charts 902, 904, 906 may be displayed as sedimentary layers where each day's contributors are stacked on top of each other in a different color. In this way, a user can visually discriminate the contributions to the bars by day.

Using Response Curves to Improve CGM

A response curve detection method may be performed in accordance with some embodiments. Specifically, the detection of the start of a significant event may be performed by monitoring a user's EGV over time. This may also include finding a plateau of the event to indicate when the event is over, and how to cope with some amount of fluctuation/noise that would still be considered part of the event.

Similar to a rate of change calculation, a computer device, such as one or more of devices 8, 14, 16, 18, 20 of FIG. 1, may calculate the current response curve. The computer device may have a response curve alert letting the user know that an event or response is taking too long to stabilize. The computer device may display the last few response curves, displaying start time, delta duration, delta EGV, and EGV rate. The patient may use the response curve results to make decisions about how to alter their medication, food intake, or behavior for the next event. For example, the curve may indicate to the user that certain behaviors, e.g. exercise or caloric intake, trigger a particular response. As a result, the user may alter their behavior based on the indicated pattern information. In addition, the user may provide as input details regarding the behavior which may be analyzed and displayed alongside the detected patterns. For example, the user may provide the number of calories consumed, the type of food consumed, and/or the type of activity performed by the user at various time periods in a day. These inputs may be used for pattern analysis and indicate patterns in EGV levels to the user based on the user's behavior.

Further, the computer device may prompt the user to enter an event whenever the computing system detects a significant response curve. For example, following a period of exercise, the user's EGV levels may fall below a particular threshold or may exhibit a particular response curve which is detected by the computing system. The user may be prompted to enter the activity performed and time of day information in order to analyze and detect pattern data.

The response curves (and entered event data) can be displayed on charts and graphs to aid users in quickly identifying areas of responses that need better control. For example, the computing system could use the onset of response curves to automatically detect pre/post meal times and automatically calculate pre/post meal statistics. The user may then make long term decisions, rather than reactionary decisions, regarding correction of EGV levels based on the statistics and detected pattern data.

A computing system may maintain state information regarding pattern analysis process iterations. For example, the information may include a list of events that have been detected, including the start time and end time of each event. Further, the state information may include the patterns that were selected for display, including a list of events that make up the pattern. The state information may also include a pattern analysis log, which includes the time the analysis was performed, and the time at which next analysis should start. For example, the time at which the next analysis should start may correspond to the start time of an episode that did not end by the time the last iteration was performed.

Embodiments discussed herein may assist in training a user to make better decisions within a few hours of a prior problem. Rather than constantly requiring the user to enter event data, embodiments discussed herein may allow a user to focus on entering information about problem areas that need more attention as opposed to needing to enter a myriad of information. Further, embodiments discussed herein may use response curves to create a more accurate analysis of times of the day instead of only using fixed times throughout the day.

It is further believed that some embodiments can improve diabetes management, improve trend detection, improve glucose control, reduce hyperglycemic and hypoglycemic events, improve information for the user to take action upon in a more timely matter, and improve a patient's recognition of patterns.

Applying response curves may also introduce retrospective information over a longer time frame than rate of change information alone and may be more quantitative than a trend line.

Further Implementations of User Interface for Displaying Results of Pattern Detection As discussed herein, a user interface may be provided to allow a user to access and define parameters for pattern detection and analysis. The user interface can be incorporated into a graphical user interface of one or more of devices 14, 16, 18, or 20 of FIG. 1, for example.

In some implementations, the graphical user interface may enable a user to change the parameters for any of the pattern detection processes described herein. The following is a non-exclusive list of example parameters that the user can change: threshold values (e.g. TH1, TH2, TP1) discussed with reference to FIG. 6; and bounds criteria, weighted assignment maps, pattern thresholds, and pattern occurrence criteria (discussed with reference to FIG. 7).

In some implementations, the graphical user interface may allow a user to initiate the pattern analysis at any point in time and select when the pattern analysis will be run.

In some implementations, the graphical user interface may allow a user to view a list of patterns that have been found so far. For example, the list may display the last five patterns that have been found. Each item in the list may show, for example, the following information: ID of the pattern (for example, each pattern may be coded with a pattern number and may be displayed as Pnn, where nn corresponds to the ID number of the pattern); and the dates over which the pattern spans: For example: Mar. 21, 2011 to Apr. 5, 2011; the time of day where the pattern was found (for example: 2:00 AM to 5:00 AM).

In some implementations, the graphical user interface may allow a user to access a view that displays the trend of the first day in the pattern (e.g. a 6 hour graph around the pattern). The user interface may also include user-selectable up and down buttons to scroll to the next and previous day. This view of the interface may also have a window displaying trend graphs from all days, overlapped.

When the pattern analysis method runs automatically and finds a pattern, the user interface my trigger a notification to the user. When the user acknowledges the notification, the list of patterns may be displayed with the latest pattern highlighted. The user can then press select the highlighted pattern and view further details about the selected pattern. The menu showing the list of patterns may also have a menu item to transition the device such that the trend screen is displayed to the user.

The user interface can also include a menu for selecting a pattern analysis profile from a plurality of user selectable pattern analysis profiles. Each pattern analysis profile can define the values of some or all of the thresholds and time periods used for pattern detection and/or weighted algorithms (e.g., weighted algorithm maps) depending upon the pattern analysis method being used. Each profile can also be associated with detection of particular pattern characteristics, such as identifying a particular type of episode (e.g., hypoglycemic or hyperglycemic episode), a sensitivity associated with considering an event an episode for pattern analysis, and time periods for analyzing data (e.g., particular times of the data, such as morning, day, evening or night). As an example, one exemplary profile can be associated with settings that have a high sensitivity for determining hypoglycemic patterns in the morning, and another exemplary profile can be associated with a low sensitivity for determining hypoglycemic events during the day. A profile associated with a high sensitivity for detecting hypoglycemic events may define some or all of the thresholds with higher values and/or time periods between episodes with lower values than a different profile associated with a lower sensitivity so to be more likely to consider an event a hypoglycemic episode and a plurality of episodes a pattern to alert a user.

In some implementations, a user can use the user interface to turn on or off a hypoglycemia reoccurrence risk alert that, when turned on, triggers an alert if it is determined that there is a risk of the host reoccurring into hypoglycemia within a predetermined time of having already detected a hypoglycemia event or episode. The hypoglycemic event can be characterized by any of the manners discussed herein or can simply be characterized as the user's glucose concentration falling below a threshold, such as 55 mg/dL. The predetermined amount of time can be user configurable and can be 48 hours, for example. In some embodiments, the hypoglycemia risk alert can be triggered regardless as to whether the rate of change of the host's glucose concentration is falling and regardless as to whether the user has another alert set to trigger an alarm at a low glucose concentration level. In some embodiments, the hypoglycemia reoccurrence risk alert includes highlighting a portion of a trend graph displayed on the user interface that corresponds to the predetermined amount of time after the detected severe hypoglycemia event. Although not wishing to be bound by theory, it is believed that a person with diabetes is at risk for recurring hypoglycemia within 48 hours of a severe hypoglycemic event and, thus, the hypoglycemia reoccurrence risk alert can notify a user of this risk.

Figure 11:
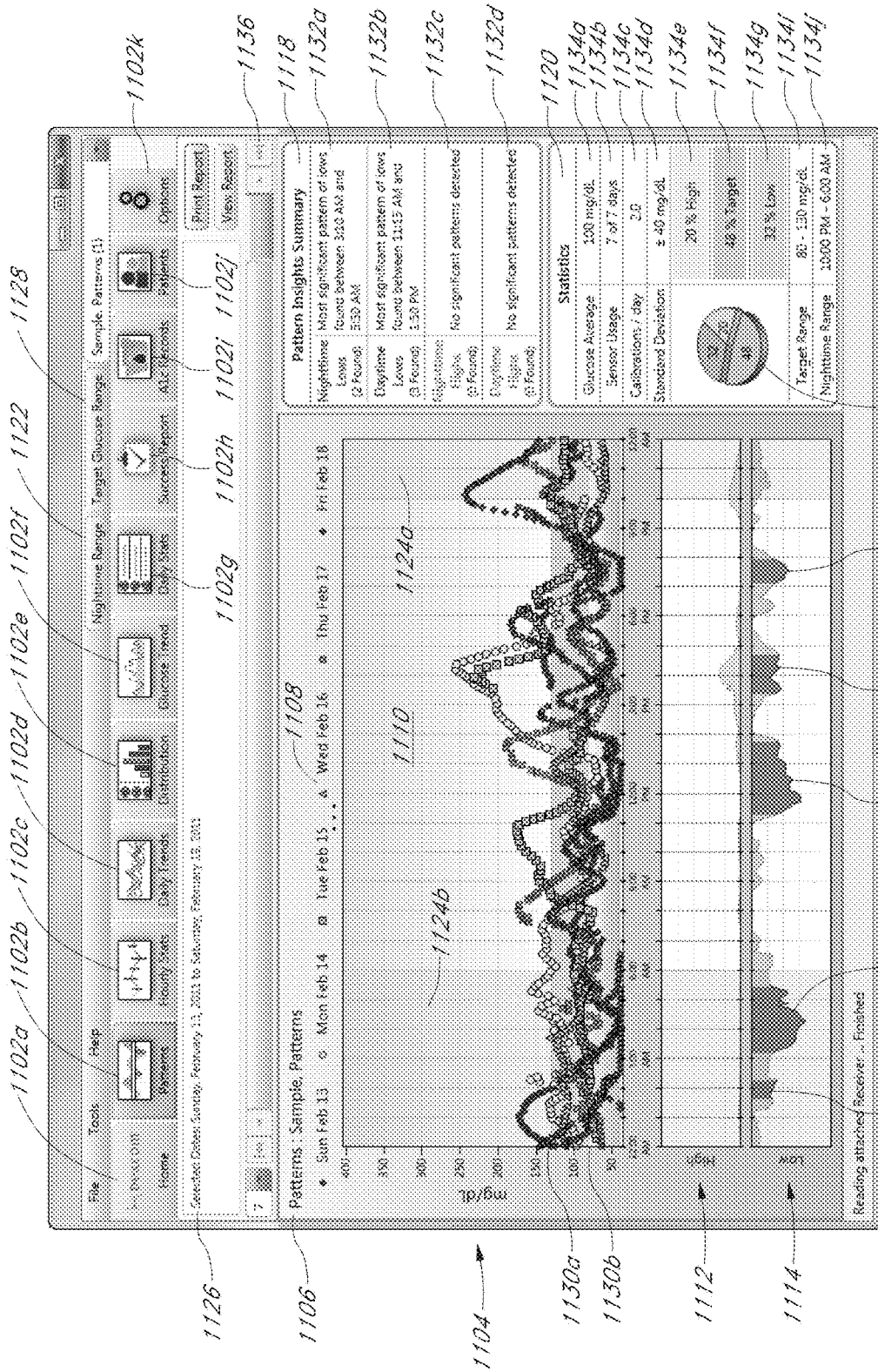
FIG. 11 illustrates another graphical user interface for displaying pattern results according to some embodiments.

A graphical user interface 1100 is illustrated in FIG. 11 in accordance with one implementation. The user interface 1100 can be implemented on a display of one or more of devices 14, 16, 18, or 20 of FIG. 1, for example. That is, user interface 1100 can be embodied as instructions stored in computer memory and executed by one or more computer processors of device 14, 16, 18, or 20 to cause display of the graphical user interface on the display device.

As illustrated in FIG. 11, graphical user interface 1100 includes a plurality of tabs 1102a-1102k. A user can select one of tabs 1102a-1102k to cause user interface 1100 to switch to a view corresponding to the tab. The tabs 1102a-1102k of user interface 1100 include a home tab 1102a, a pattern tab 1102b, a hourly stats tab 1102c, a daily trends tab 1102d, and distribution tab 1102e, a glucose trend tab 1102f, a daily stats tab 1102g, and success report tab 1102h an A1c records tab 1102i, a patients tab 1102j and an options tab 1102k. User interface 1100 in FIG. 11 illustrates the view corresponding to the patterns tab 1102. The patterns tab 1002 is selected in FIG. 11.

User interface 1100 includes a pattern chart 1104. In this implementation, the pattern chart 1104 includes a modal day trend chart 1110 section showing day over day estimated glucose value (EGV) trend lines, a high (above target) pattern plot chart 1112 section that highlights significant pattern ranges (none shown in FIG. 11), and a low (below target) pattern plot chart 1114 section with highlighted significant pattern ranges 1116a-1116e, a pattern insights summary table 1118 and a statistics table 1120. The model day trend chart 1110, high pattern plot chart 1112 and low pattern plot chart 1114 can be implemented as discussed above with respect to FIG. 7 and FIG. 9. Further, as illustrated in FIG. 11, the model day trend chart 1110, high pattern plot chart 1112 and low pattern plot chart 1114 each have the same x-axis scale, which can facilitate comparing the data shown in each of the charts.

Pattern chart 1104 includes a title 1106 and a legend 1108 located at the top of the chart. The title 1106 can be a textual description describing a type or types of patterns to be detected in the pattern plot chart 1112. The legend 1108 include markers associated with each different EGV trace in the model day chart 1110, where each marker can be differentiated from the markers making up the other traces by color and/or shape. Further, the legend 1108 can indicate the day and date associated with each of the markers.

Graphical user interface 1100 also includes a user selectable nighttime time range button 1122. In some implementations, each patient can have a specific range of time that indicates times of day when it is considered nighttime, such as 10 PM to 6 AM as illustrated in FIG. 11, although any other range can be used instead. Graphical user interface 1100 displays the currently defined nighttime time range for the patient as vertical light grey strip lines 1124a and 1124b that coincide with the start and end of the times, respectively, of the nighttime range. The strip lines 1124a and 1124b can be shown on the model day chart 1110 and both pattern charts 1112 and 1114.

Selecting the nighttime range button 1122 can initiate a time of day range editor window to be displayed on graphical user interface 1100. This editor window can allow the user to change the nighttime range. Changing to the patient's nighttime range can cause user interface 1100 to automatically update to reflect the change in nighttime range, such as changing the strip lines 1124a and 1124b to reflect the change and any insights related to the nighttime range reflected in pattern insight summary 1118 and statistics summary 1120.

Graphical user interface 1100 can also include a display setting text box 1126 that displays a timeframe (i.e. the range of dates and/or times of patient data) presently being analyzed and displayed using the user interface. In some implementations, text box 1126 can also include an indication if the patient data is blinded.

Graphical user interface 1100 also includes a user selectable target glucose range button 1128. In some implementation, the target glucose range defines a range of glucose values in which a patient desires to maintain his or her glucose concentration. A glucose concentration above the target range can be considered a "high," and a glucose concentration below the target range can be considered a "low." Graphical user interface 1100 can display a high line 1130a and a low line 1130b on the model chart 1110 representing the high of the target range and the low of the target range, respectively. The sections of model chart 1110 separated by the high line 1130a and low line 1130b can be distinctively displayed from one another, such as each section having a different shading or color. In one implementation, the section of the model chart 1110 above the high line 1130a is a yellow color, the section between lines 1130a and 1130b is a green color and the section below line 1130b is a red color. These colors associated with high, target and low sections can also be used in other parts of graphical user interface 1100 that relate to respective high, target or low glucose values. For example, the text "Night time Low" insight in pattern insight summary 1118 can be also displayed in a red color because it relates to a low glucose value as defined by the target glucose range.

Selecting the target glucose range button 1128 can cause a target glucose range editor window to be displayed (e.g., a pop up window) on graphical user interface 1100. This editor window can allow the user to select of modify the target glucose range. Changing to the patient's target glucose range can cause user interface 1100 to automatically update to reflect the change in target glucose range, such as changing the lines 1130a and 1130b to reflect the target range change, any insights and statistics in pattern summary 1118 and statistics 1120 determined based on how the target range is defined.

As discussed above, graphical user interface 1100 can indicate if the user is in a blinded mode (e.g., user interface 1100 can display "Blinded" in the text box 1126). If the user is in a blinded mode, then graphical user interface 1100 does not display certain information in accordance with some implementations, such any view showing a user's actual EGV values. In one implementation, when in the blinded mode, graphical user interface still displays the Sensor Usage, Calibrations/day, Target Range, and Nighttime Range in the Statistics table 1120, but does not display one or more of the model chart 1110, pattern charts 112 and 1114, and Glucose Average in the statistics table 1120.

The high and low pattern plot charts 1112 and 1114 can be implemented in any manner described above with respect to FIGS. 7-9. To further describe use of high and low pattern plot charts 1112 and 1114, the following illustrates some exemplary implementations.

The high and low pattern plot charts 1112 and 1114 can display a line graph across all 288 of the 5 minute intervals of a day. Each 5 minute interval's plotted value can be the sum of all the EGV contributions that were above/below the target range limits in that interval and where the contribution amount is a weighted value as function of how far away from the target limits the EGV value was. In one implementation, the further away from target, the larger the weighted contribution value is for that EGV in that interval, but other weighted functions can be used, such as any of the weight maps or functions described above.

The high and low pattern plot charts 1112 and 1114 can be useful to highlight significant time ranges where a set of intervals have exceeded thresholds for both frequency (n out of m days) and severity (the average of weighted contributions). In some implementations, a significant set of intervals is defined as having at least 3 intervals (15 minutes) and coalesce with an adjoining significant interval if less than 9 intervals (45 minutes) away. An interval can also be defined in any of the manners discussed herein with reference to defining a segment or pattern.

FIG. 11 illustrates significant time ranges 1116a-1116e in the Low pattern chart 1114. No significant time ranges were identified in the High pattern chart 1112. Accordingly, a user can discern that they may want to try to modify his or her behavior to better hypoglycemic control.

In some implementations, the detection of significant time ranges on the high and low pattern plot charts 1112 and 1114 have increased sensitivity (i.e. a lower threshold on the average of weighted contributions) during the nighttime range, which can be defined using nighttime range button 1122, as discussed above.

In some implementations of user interface 1100, the detection of significant time ranges on the high and low pattern plot charts 1112 and 1114 is automatically disabled if the current number of days viewed is only one or two days. That is, in some implementations, at least three possible days of contributing EGV values are needed for the frequency threshold to be considered.

In some implementations, the y-axis scale of the high and low pattern plot charts 1112 and 1114 can be adaptive and relative to the timeframe of data chosen to be analyzed and displayed. The scale can be adjusted to be approximately 80% of the maximum possible sum of weighted glucose contribution values.

The pattern summary table 1118 of user interface 1100 can indicate a total number of significant patterns and a description (e.g., time range) of one or more of the most significant patterns. The patterns can be grouped by four categories: Nighttime Lows 1132a, Daytime Lows 1132b, Nighttime Highs 1132c, and Daytime Highs 1132d. The most significant pattern in each of the four groups can be determined by a volume; that is, a total sum of all contributed values within the pattern interval. A pattern can be considered in a nighttime group if the patterns start time or nadir point is in the patient's defined nighttime range, and, conversely, a pattern can be considered in a daytime group if the pattern's start time or nadir point is in the patient's defined nighttime range.

In some implementations, when hovering a computer cursor (e.g., the pointer controlled by a computer mouse) or finger, in the case of user interface 1100 having touch-sensitive screen capabilities, over one of the rows 1132a-1132d of the pattern summary table 1118, the user interface 1100 can highlight the time interval corresponding to the selected pattern using, for example, a shaded vertical strip extending across each of the charts 1104, 1112, and 1114 (not shown).

The statistics table 1120 can display a variety of statistical values based on data falling within the selected timeframe being viewed on user interface 1100. The statistics table 1120 can include: a glucose average 1134a (i.e. the mean of all glucose values found in the currently selected days being viewed); sensor usage 1134b (e.g. determined based on the number of days that contain at least one glucose value out of the number of days currently selected); calibrations per day 1134c (e.g., determined based on the total number of meter values found in the currently selected days divided by the sensor usage days); standard deviation 1134d (e.g., the standard deviation based on all of the glucose values found in the currently selected days being viewed); percentage of high values 1134e (e.g., determined based on the percentage of glucose values above the patient's defined target range); percentage of low values 1134f (e.g., determined based on the percentage of glucose values below the patient's defined target range found in the currently selected days being viewed); percentage target 1134g (e.g., determined based on the percentage of glucose values within (or equal to) the patient's defined target range found in the currently selected days being viewed); High/Low/Target pie chart 1134h representative of the percentage of high, low and target values; the currently defined patient's target glucose range 1134i (defined using target glucose range button 1128, for example); and the currently defined patient's nighttime range 1134j (defined using nighttime range button 1122, for example).

Graphical user interface 1100 also allows a user to select the timeframe of data to be analyzed and displayed on graphical user interface 1100. In some implementations, a user can select a timeframe in the range of 1 to 15 days, 1 to 18-28 days, 1 to 30 days, 1 to 60 days and 1 to 90 days.

To facilitate user selection and modification of the timeframe, the user interface 1100 includes a date slider control 1136. The date slider control 1136 can be used for choosing the timeframe of displayed information in any of the different views associated with tabs 1102a-1102j.

Figure 12:
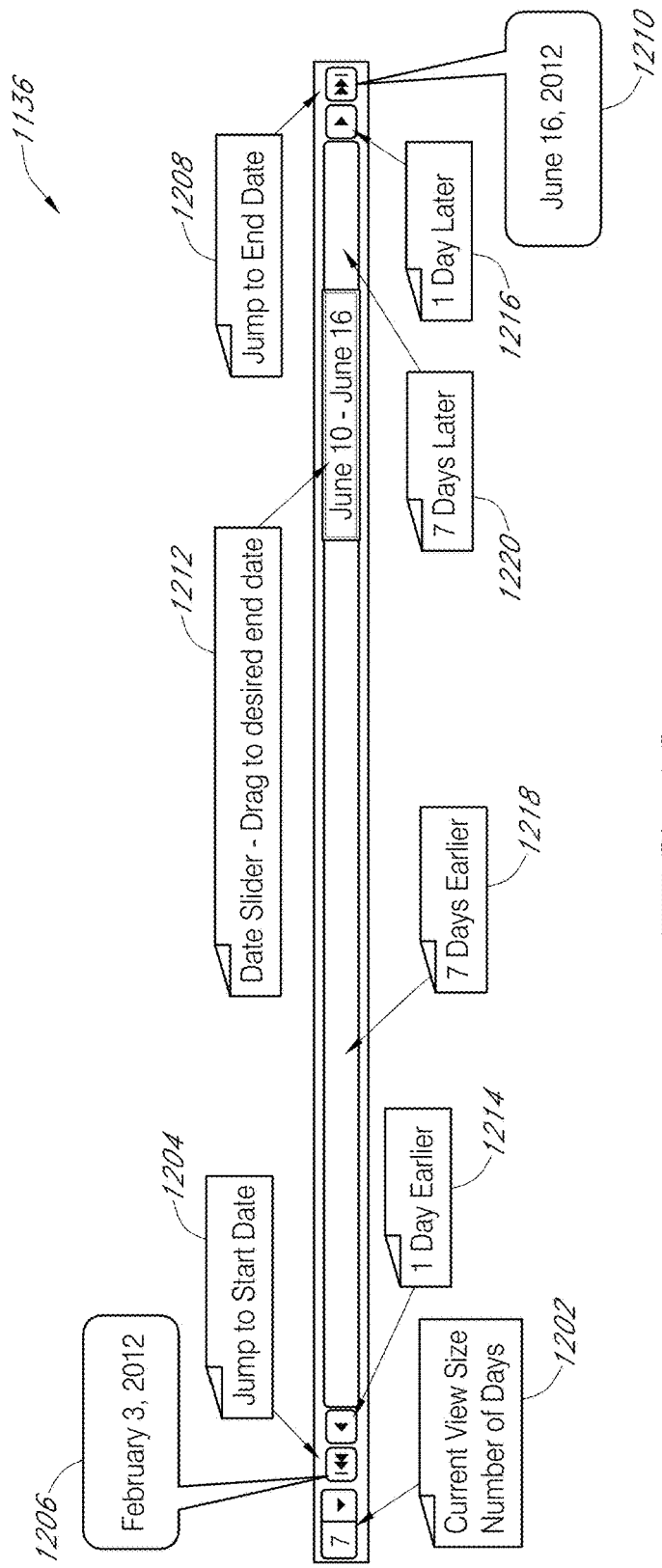
FIG. 12 relates to a date slider control for selecting a date timeframe according to some embodiments

In implementation of the date slider control 1136 is described further with respect to FIG. 12. Date slider control 1136 includes a user-selectable size control button 1202 to choose the number of days to display (i.e. the number of days in the timeframe). A user can select this section of the slider 1136 to cause a drop down menu to be displayed for a user to select a number of days desired to be used in the timeframe. The size control button 1202 can also display the current number of days in the current timeframe. In some implementations, the number of days is always "whole" days from 12:00 am to midnight.

Date slider control 1136 also includes start date button 1204. When a user selects the start date button 1204, the timeframe jumps to the first date of available data to be used with user interface 1100 (e.g., first date of data stored on device 16, 16, 18 or 20 implementing user interface 1100). Further, slider control 1136 can indicate to the user the first date of available data by hovering over the start date button 1204, which causes display of a tool tip 1206 popup that indicates the date of the first data available.

Date slider control 1136 also includes end date button 1208. When a user selects the end date button 1208, the timeframe jumps to the last date of available data to be used with user interface 1100 (e.g., last date of data stored on device 16, 16, 18 or 20 implementing user interface 1100). Further, slider control 1136 can indicate to the user the last date of available data by hovering over the end date button 1208, which displays a tool tip 1210 popup that indicates the date of the last data available.

Date slider control 1136 includes a slider bar 1212 that a user can drag horizontally to modify the date selection timeframe. Dragging the slider bar 1212 in a right-hand direction (i.e. toward the start date button 1204) causes the timeframe to increment back in time from a current date selection, and dragging the slider bar in a left-hand direction (i.e. toward the end date button 1208) causes the timeframe to increment forward in time from a current date selection. Slider bar 1212 also displays the currently selected date range (start to end, inclusive) of the timeframe. To illustrate, a currently selected time frame can be seven dates spanning from June 10 to June 16. Sliding the bar 1121 in a left-hand direction causes the timeframe to increment back in time, such as to June 3-June 9. Note that in this implementation, the number of days in a timeframe remains constant unless the view size 1202 is modified. Thus, the number of days in the timeframe remains the same as the slider is dragged.

Date slider control 1136 includes day earlier button 1214 and day later button 1216, which increments the timeframe one day forward or one day later, respectively, when selected.

Date slider control 1136 can also allow a user to increment n number of days forward or backward by selecting portions 1218 and 1220 of slider control 1136 located before and after the slider bar 1212, respectively. The number n can correspond to the number of days selected in size control button 1202. To illustrate, if the number of days selected in the size control 1202 is seven days, then selecting portion 1218 of slider control 1136 causes the slider bar 1212 to slide toward the start date button 1204 and cause the timeframe (both start and end date) to increment back in time seven days.

In accordance with some embodiments, a user can use a device (e.g., display device 14, 16, 18, 20) to implement one or more of the pattern detection techniques described herein to identify and display patterns useful for a user to monitor so to manage a chronic disease, such as diabetes. For example, the pattern analysis methods described herein can be tailored to detect hyperglycemic and/or hypoglycemic patterns occurring at particular times of the day or on particular days of the week. Patterns can be scored or weighted to identify patterns based on frequency, sequence and severity, including time spent in severe episodes. Alerts can also be triggered based on previous patterns analysis and current data indicating that the current data is following a similar enough pattern as the past identified patterns. Devices disclosed herein can also be used to input a comment regarding what a user did in response to an alert triggered in response to detection of a pattern.

While the disclosure has been illustrated and described in detail in the drawings and foregoing description, such illustration and description are to be considered illustrative or exemplary and not restrictive. The disclosure is not limited to the disclosed embodiments. Variations to the disclosed embodiments can be understood and effected by those skilled in the art in practicing the claimed disclosure, from a study of the drawings, the disclosure and the appended claims.

All references cited herein are incorporated herein by reference in their entirety. To the extent publications and patents or patent applications incorporated by reference contradict the disclosure contained in the specification, the specification is intended to supersede and/or take precedence over any such contradictory material.

Unless otherwise defined, all terms (including technical and scientific terms) are to be given their ordinary and customary meaning to a person of ordinary skill in the art, and are not to be limited to a special or customized meaning unless expressly so defined herein. It should be noted that the use of particular terminology when describing certain features or aspects of the disclosure should not be taken to imply that the terminology is being re-defined herein to be restricted to include any specific characteristics of the features or aspects of the disclosure with which that terminology is associated. Terms and phrases used in this application, and variations thereof, especially in the appended claims, unless otherwise expressly stated, should be construed as open ended as opposed to limiting. As examples of the foregoing, the term 'including' should be read to mean 'including, without limitation,' 'including but not limited to,' or the like; the term 'comprising' as used herein is synonymous with 'including,' 'containing,' or 'characterized by,' and is inclusive or open-ended and does not exclude additional, unrecited elements or method steps; the term 'having' should be interpreted as 'having at least;' the term 'includes' should be interpreted as 'includes but is not limited to;' the term 'example' is used to provide exemplary instances of the item in discussion, not an exhaustive or limiting list thereof; adjectives such as 'known', 'normal', 'standard', and terms of similar meaning should not be construed as limiting the item described to a given time period or to an item available as of a given time, but instead should be read to encompass known, normal, or standard technologies that may be available or known now or at any time in the future; and use of terms like 'preferably,' 'preferred,' 'desired,' or 'desirable,' and words of similar meaning should not be understood as implying that certain features are critical, essential, or even important to the structure or function of the invention, but instead as merely intended to highlight alternative or additional features that may or may not be utilized in a particular embodiment of the invention. Likewise, a group of items linked with the conjunction 'and' should not be read as requiring that each and every one of those items be present in the grouping, but rather should be read as 'and/or' unless expressly stated otherwise. Similarly, a group of items linked with the conjunction 'or' should not be read as requiring mutual exclusivity among that group, but rather should be read as 'and/or' unless expressly stated otherwise.

Where a range of values is provided, it is understood that the upper and lower limit, and each intervening value between the upper and lower limit of the range is encompassed within the embodiments.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. The indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. Any reference signs in the claims should not be construed as limiting the scope.

It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

All numbers expressing quantities of ingredients, reaction conditions, and so forth used in the specification are to be understood as being modified in all instances by the term 'about.' Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

It will be appreciated that, for clarity purposes, the above description has described embodiments with reference to different functional units. However, it will be apparent that any suitable distribution of functionality between different functional units may be used without detracting from the invention. For example, functionality illustrated to be performed by separate computing devices may be performed by the same computing device. Likewise, functionality illustrated to be performed by a single computing device may be distributed amongst several computing devices. Hence, references to specific functional units are only to be seen as references to suitable means for providing the described functionality, rather than indicative of a strict logical or physical structure or organization.

Furthermore, although the foregoing has been described in some detail by way of illustrations and examples for purposes of clarity and understanding, it is apparent to those skilled in the art that certain changes and modifications may be practiced. Therefore, the description and examples should not be construed as limiting the scope of the invention to the specific embodiments and examples described herein, but rather to also cover all modification and alternatives coming with the true scope and spirit of the invention.

What is claimed is:

1. A computer-implemented method for identifying patterns in continuous analyte data of a patient user monitored by a continuous analyte monitoring system comprising a continuous analyte sensor device to generate the continuous analyte data in communication with a computing device including a memory to store the generated continuous analyte data and a processor module to process the continuous analyte data according to the computer-implemented method, the computer-implemented method comprising:
    obtaining analyte data points falling within a designated date range, wherein an analyte data point includes an analyte value and a corresponding time value;
    applying one of more filters to the analyte data points to generate contributor data points;
    weighting each contributor data point of the generated contributor data points based on the contributor data point's analyte value;
    assigning each weighted contributor data point to a corresponding epoch according to the time value associated with the weighted contributor data point;
    applying at least one pattern threshold to an epoch to determine a match of whether the weighted contributor data point or weighted contributor data points assigned to the epoch meet the at least one pattern threshold, wherein the applying includes assigning a flag to the epoch when a match is determined;
    determining one or more pattern occurrences by scanning the epochs for flags, wherein the determined one or more pattern occurrences are indicative of repeated patterns of the patient user's monitored analyte levels; and
    outputting information representative of the determined one or more pattern occurrences, wherein the outputted pattern information is transmitted to an insulin pump controller based on an automatic trigger to control insulin administration based on the pattern information.

2. The method of claim 1, wherein the designated date range is at least three days.

3. The method of claim 1, wherein the one or more filters comprises filters selected from the group consisting of:
    (i) an analyte value filter that filters out analyte data points that have an analyte concentration value falling outside of a predetermined analyte level or range of analyte values;
    (ii) a time range filter that filters out analyte data points measurements that falls outside of a time of day range;
    (iii) a day of the week filter that filters out analyte data points measured one or more predetermined days of the week; and
    (iv) an event filter that filters out data points that do not fall within a predetermined amount of time from an occurrence of an event.

4. The method of claim 3, wherein the event is an event selected from the group consisting of exercise, a meal, sleep and administration of a medication.

5. The method of claim 4, further comprising receiving user input indicative of the event using a user interface.

6. The method of claim 1, wherein weighting each contributor data point is based on a predetermined weight assignment map or mathematical assignment function.

7. The method of claim 1, wherein weighting each contributor data point comprises assigning a weighted value to each contributor data point, wherein the assigned weighted value is smaller if the analyte value is less clinically significant than if the analyte value is more clinically significant.

8. The method of claim 7, wherein the assignment of weighted values is non-linear based on the analyte value.

9. The method of claim 1, wherein each epoch spans a determined time of day and wherein each contributor data point is added to the epoch that spans the corresponding time of day.

10. The method of claim 1, wherein the pattern thresholds comprise thresholds selected from the group consisting of:
a threshold minimum number of contributor data points in an epoch;
a threshold average weighted value of the contributor data points in an epoch;
a threshold medium weighted value of the contributor data points in the epoch;
a threshold sum of the weighted values of the contributor data points in the epoch;
a threshold average difference of the weighted values of the contributor data points in the epoch;
a threshold standard deviation value of the weighted values of the contributor data points in the epoch; and
a threshold correlation value.

11. The method of claim 10, wherein at least one of the thresholds is defined in terms of a percentage.

12. The method of claim 1, wherein an epoch is flagged when at least some of the one or more thresholds are satisfied.

13. The method of claim 1, wherein determining the one or more pattern occurrences comprises determining a start and an end of a pattern.

14. The method of claim 13, wherein determining the start and the end of the pattern is determined based on identifying a predetermined minimum number of contiguous matching epochs or a predetermined ratio of contiguous matching to non-matching epochs.

15. The method of claim 13, wherein the start of the pattern is determined based on identifying a first threshold number of contiguous matching epochs and the end of the pattern is determined based on identifying a second threshold number non-matching epochs.

16. The method of claim 13, wherein the outputted information comprises the start time and the end time associated with when a repeated pattern of the patient user's monitored analyte levels occurred.

17. The method of claim 1, wherein determining the one or more pattern occurrences is based on the frequency of matching epochs and the weighted values of the matching epochs.

18. The method of claim 1, wherein the outputted information comprises a triggering alert notifying the patient user of the one or more patterns occurrences.

19. The method of claim 1, wherein the outputted information is processed further to form or modify a medication administration routine.

20. A method for augmenting the performance of a continuous analyte monitoring system by identifying repeated patterns in continuous analyte data of a patient user monitored by the continuous analyte monitoring system, in which the continuous analyte monitoring system comprises a continuous analyte sensor device to generate the continuous analyte data in communication with a computing device including a memory to store the generated continuous analyte data and a processor module to process the continuous analyte data to identify the repeated patterns, the method comprising:
(a) detecting, by the continuous analyte sensor device, analyte levels of the patient user over a designated time range to form a continuous analyte data set;
(b) processing, by the computing device, the continuous analyte data set to identify repeated patterns in the detected analyte values over the designated time range, the processing including:
  (i) obtaining analyte data points of the continuous analyte data set falling within a designated time range, wherein an analyte data point includes an analyte value and a corresponding time value,
  (ii) applying one of more filters to the analyte data points to generate contributor data points,
  (iii) weighting each contributor data point of the generated contributor data points based on the contributor data point's analyte value,
  (iv) assigning each weighted contributor data point to a corresponding epoch according to the time value associated with the weighted contributor data point,
  (v) applying at least one pattern threshold to an epoch to determine a match of whether the weighted contributor data point or weighted contributor data points assigned to the epoch meet the at least one pattern threshold, wherein the applying includes assigning a flag to the epoch when a match is determined, and
  (vi) determining one or more pattern occurrences in the continuous analyte data set by scanning the epochs for flags, wherein the determined one or more pattern occurrences are indicative of one or more repeated patterns of the patient user's monitored analyte levels; and
(c) producing, by the computing device, an output based on the determined one or more patterns occurrences, and controlling insulin administration of an insulin pump controller based on an automatic trigger in response to the output.

21. A method for augmenting the performance of a continuous analyte monitoring system by identifying repeated patterns in continuous analyte data of a patient user monitored by the continuous analyte monitoring system, in which the continuous analyte monitoring system comprises a continuous analyte sensor device to generate the continuous analyte data in communication with a computing device including a memory to store the generated continuous analyte data and a processor module to process the continuous analyte data to identify the repeated patterns, the method comprising:
(a) detecting, by the continuous analyte sensor device, analyte levels of the patient user over a designated time range to form a continuous analyte data set;
(b) processing, by the computing device, the continuous analyte data set to identify repeated patterns in the detected analyte values over the designated time range, the processing including:
  (i) obtaining analyte data points of the continuous analyte data set falling within a designated time range, wherein an analyte data point includes an analyte value and a corresponding time value, (ii) applying one of more filters to the analyte data points to generate contributor data points,
(iii) weighting each contributor data point of the generated contributor data points based on the contributor data point's analyte value,
(iv) assigning each weighted contributor data point to a corresponding epoch according to the time value associated with the weighted contributor data point,
(v) applying at least one pattern threshold to an epoch to determine a match of whether the weighted contributor data point or weighted contributor data points assigned to the epoch meet the at least one pattern threshold, wherein the applying includes assigning a flag to the epoch when a match is determined, and
(vi) determining one or more pattern occurrences in the continuous analyte data set by scanning the epochs for flags, wherein the determined one or more pattern occurrences are indicative of one or more repeated patterns of the patient user's monitored analyte levels; and
(c) controlling medication administration of a medication administration device based on an automatic trigger based on the determined one or more pattern occurrences, wherein execution of the produced output causes the medication administration device to increase or decrease a dose amount of a medication to treat a medical condition associated with the monitored analyte, or cease administration of the medication.

* * * * *

UNITED STATES PATENT AND TRADEMARK OFFICE
CERTIFICATE OF CORRECTION

| | |
|---|---|
| PATENT NO. | : 10,349,871 B2 |
| APPLICATION NO. | : 13/566678 |
| DATED | : July 16, 2019 |
| INVENTOR(S) | : Phil Mayou |

It is certified that error appears in the above-identified patent and that said Letters Patent is hereby corrected as shown below:

In the Drawings

In sheet 8 of 16, Figure 7, reference numeral 704, Line 2, delete "glocose" and insert -- glucose --, therefor.

In sheet 8 of 16, Figure 7, reference numeral 716, Line 2, delete "Occurance(s)" and insert -- Occurrence(s) --, therefor.

In sheet 8 of 16, Figure 7, reference numeral 718, Line 2, delete "Occurances" and insert -- Occurrences --, therefor.

In the Specification

In Column 9, Line 43, delete "andrenostenedione;" and insert -- androstenedione; --, therefor.

In Column 9, Line 59, delete "diptheria" and insert -- diphtheria --, therefor.

In Column 9, Line 66, delete "perioxidase;" and insert -- peroxidase; --, therefor.

In Column 10, Line 12, delete "duodenalisa," and insert -- duodenalis, --, therefor.

In Column 10, Line 20, delete "Trepenoma pallidium," and insert -- Treponema pallidum, --, therefor.

In Column 10, Line 21, delete "stomatis" and insert -- stomatitis --, therefor.

In Column 10, Lines 41-42, delete "(barbituates," and insert -- (barbiturates, --, therefor.

In Column 29, Line 6, delete "18, as" and insert -- 18, 20 as --, therefor.

Signed and Sealed this
Twenty-ninth Day of October, 2019

Andrei Iancu
*Director of the United States Patent and Trademark Office*

In Column 31, Line 29, delete "that that" and insert -- that --, therefor.

In Column 36, Line 21, delete "that that" and insert -- that --, therefor.